US012678173B2

(12) United States Patent
Khan et al.

(10) Patent No.: US 12,678,173 B2
(45) Date of Patent: Jul. 14, 2026

(54) APPARATUS, SYSTEM, AND METHOD FOR OSTEOTOMIES

(71) Applicant: Treace Medical Concepts, Inc., Ponte Vedra, FL (US)

(72) Inventors: Andrew C. Khan, Clermont, FL (US); Adam D. Perler, St. Petersburg, FL (US); James Q. Spitler, Winter Garden, FL (US)

(73) Assignee: Treace Medical Concepts, Inc., Ponte Vedra, FL (US)

( * ) Notice: Subject to any disclaimer, the term of this patent is extended or adjusted under 35 U.S.C. 154(b) by 134 days.

(21) Appl. No.: 18/422,933

(22) Filed: Jan. 25, 2024

(65) Prior Publication Data

US 2024/0252180 A1     Aug. 1, 2024

Related U.S. Application Data

(60) Provisional application No. 63/482,197, filed on Jan. 30, 2023, provisional application No. 63/482,038, filed on Jan. 28, 2023.

(51) Int. Cl.
*A61B 17/15* (2006.01)
*A61B 17/17* (2006.01)
(Continued)

(52) U.S. Cl.
CPC ........ *A61B 17/151* (2013.01); *A61B 17/1775* (2016.11); *A61B 17/56* (2013.01);
(Continued)

(58) Field of Classification Search
CPC . A61B 17/151; A61B 17/56; A61B 2017/564; A61B 2017/565; A61B 17/1775
See application file for complete search history.

(56) References Cited

U.S. PATENT DOCUMENTS 3,664,022 A     5/1972  Small
4,069,824 A     1/1978  Weinstock
(Continued)

FOREIGN PATENT DOCUMENTS

AU     2009227957 B2     7/2014
AU     2009222469 B2     2/2015
(Continued)

OTHER PUBLICATIONS

Decarbo et al., "The Weil Osteotomy: A Refresher," Techniques in Foot and Ankle Surgery, vol. 13, No. 4, Dec. 2014, pp. 191-198.
(Continued)

*Primary Examiner* — Samuel S Hanna
(74) *Attorney, Agent, or Firm* — Fredrikson & Byron, P.A.

(57)     ABSTRACT

An apparatus, system, and method are disclosed for remediating a condition present in a patient. In certain implementations, the device may include a body having a proximal side, a distal side, a medial side, a lateral side, an inferior side, and a superior side. In addition, the device may include a window that extends from one side of the body to an opposite side of the body, the window configured to enable a user to view an anatomical reference when the apparatus is in use. The device may include a reference feature guide coupled to the body, the reference feature guide configured to guide a user in providing one or more reference features.

13 Claims, 23 Drawing Sheets

(51) Int. Cl.

| | |
|---|---|
| *A61B 17/56* | (2006.01) |
| *A61B 34/10* | (2016.01) |
| *A61B 90/00* | (2016.01) |
| *A61B 17/00* | (2006.01) |

(52) U.S. Cl.
CPC .............. *A61B 34/10* (2016.02); *A61B 90/08* (2016.02); *A61B 2017/00902* (2013.01); *A61B 2017/564* (2013.01); *A61B 2034/105* (2016.02); *A61B 2034/108* (2016.02); *A61B 2090/0807* (2016.02)

(56) References Cited

U.S. PATENT DOCUMENTS

| | | | |
|---|---|---|---|
| 4,159,716 | A | 7/1979 | Borchers |
| 4,187,840 | A | 2/1980 | Watanabe |
| 4,335,715 | A | 6/1982 | Kirkley |
| 4,338,927 | A | 7/1982 | Volkov et al. |
| 4,349,018 | A | 9/1982 | Chambers |
| 4,409,973 | A | 10/1983 | Neufeld |
| 4,436,684 | A | 3/1984 | White |
| 4,440,168 | A | 4/1984 | Warren |
| 4,509,511 | A | 4/1985 | Neufeld |
| 4,565,191 | A | 1/1986 | Slocum |
| 4,570,624 | A | 2/1986 | Wu |
| 4,628,919 | A | 12/1986 | Clyburn |
| 4,736,737 | A | 4/1988 | Fargie et al. |
| 4,750,481 | A | 6/1988 | Reese |
| 4,754,746 | A | 7/1988 | Cox |
| 4,757,810 | A | 7/1988 | Reese |
| 4,839,822 | A | 6/1989 | Dormond et al. |
| 4,895,141 | A | 1/1990 | Koeneman et al. |
| 4,959,066 | A | 9/1990 | Dunn et al. |
| 4,978,347 | A | 12/1990 | Ilizarov |
| 4,988,349 | A | 1/1991 | Pennig |
| 4,995,875 | A | 2/1991 | Coes |
| 5,049,149 | A | 9/1991 | Schmidt |
| 5,053,039 | A | 10/1991 | Hofmann et al. |
| 5,112,334 | A | 5/1992 | Alchermes et al. |
| 5,147,364 | A | 9/1992 | Comparetto |
| 5,171,244 | A | 12/1992 | Caspari et al. |
| 5,176,685 | A | 1/1993 | Rayhack |
| 5,207,676 | A | 5/1993 | Canadell et al. |
| 5,254,119 | A | 10/1993 | Schreiber |
| 5,312,412 | A | 5/1994 | Whipple |
| 5,358,504 | A | 10/1994 | Paley et al. |
| 5,364,402 | A | 11/1994 | Mumme et al. |
| 5,374,271 | A | 12/1994 | Hwang |
| 5,417,694 | A | 5/1995 | Marik et al. |
| 5,449,360 | A | 9/1995 | Schreiber |
| 5,470,335 | A | 11/1995 | Du Toit |
| 5,490,854 | A | 2/1996 | Fisher et al. |
| 5,529,075 | A | 6/1996 | Clark |
| 5,540,695 | A | 7/1996 | Levy |
| 5,578,038 | A | 11/1996 | Slocum |
| 5,586,564 | A | 12/1996 | Barrett et al. |
| 5,601,565 | A | 2/1997 | Huebner |
| 5,613,969 | A | 3/1997 | Jenkins, Jr. |
| 5,620,442 | A | 4/1997 | Bailey et al. |
| 5,643,270 | A | 7/1997 | Combs |
| 5,662,656 | A | 9/1997 | White |
| 5,667,510 | A | 9/1997 | Combs |
| H1706 | H | 1/1998 | Mason |
| 5,722,978 | A | 3/1998 | Jenkins, Jr. |
| 5,749,875 | A | 5/1998 | Puddu |
| 5,779,709 | A | 7/1998 | Harris, Jr. et al. |
| 5,788,695 | A | 8/1998 | Richardson |
| 5,803,924 | A | 9/1998 | Oni et al. |
| 5,810,822 | A | 9/1998 | Mortier |
| 5,836,950 | A | 11/1998 | Hansson |
| 5,839,438 | A | 11/1998 | Graettinger et al. |
| 5,843,085 | A | 12/1998 | Graser |
| 5,893,553 | A | 4/1999 | Pinkous |
| 5,911,724 | A | 6/1999 | Wehrli |
| 5,935,128 | A | 8/1999 | Carter et al. |
| 5,941,877 | A | 8/1999 | Viegas et al. |
| 5,951,556 | A | 9/1999 | Faccioli et al. |
| 5,957,927 | A | 9/1999 | Magee et al. |
| 5,980,526 | A | 11/1999 | Johnson et al. |
| 5,984,931 | A | 11/1999 | Greenfield |
| 6,007,535 | A | 12/1999 | Rayhack et al. |
| 6,030,391 | A | 2/2000 | Brainard et al. |
| 6,162,223 | A | 12/2000 | Orsak et al. |
| 6,171,309 | B1 | 1/2001 | Huebner |
| 6,203,545 | B1 | 3/2001 | Stoffella |
| 6,248,109 | B1 | 6/2001 | Stoffella |
| 6,391,031 | B1 | 5/2002 | Toomey |
| 6,416,465 | B2 | 7/2002 | Brau |
| 6,478,799 | B1 | 11/2002 | Williamson |
| 6,511,481 | B2 | 1/2003 | Von Hoffmann et al. |
| 6,676,662 | B1 | 1/2004 | Bagga et al. |
| 6,712,824 | B2 | 3/2004 | Millard et al. |
| 6,719,773 | B1 | 4/2004 | Boucher et al. |
| 6,743,233 | B1 | 6/2004 | Baldwin et al. |
| 6,755,838 | B2 | 6/2004 | Trnka |
| 6,780,190 | B2 | 8/2004 | Maroney |
| 6,796,986 | B2 | 9/2004 | Duffner |
| 6,859,661 | B2 | 2/2005 | Tuke |
| 6,944,518 | B2 | 9/2005 | Roose |
| 6,964,645 | B1 | 11/2005 | Smits |
| 7,033,361 | B2 | 4/2006 | Collazo |
| 7,097,647 | B2 | 8/2006 | Segler |
| 7,153,310 | B2 | 12/2006 | Ralph et al. |
| 7,182,766 | B1 | 2/2007 | Mogul |
| 7,241,298 | B2 | 7/2007 | Nemec et al. |
| 7,282,054 | B2 | 10/2007 | Steffensmeier et al. |
| 7,351,203 | B2 | 4/2008 | Jelliffe et al. |
| 7,377,924 | B2 | 5/2008 | Raistrick et al. |
| 7,465,303 | B2 | 12/2008 | Riccione et al. |
| 7,473,255 | B2 | 1/2009 | Mcgarity et al. |
| 7,540,874 | B2 | 6/2009 | Trumble et al. |
| 7,572,258 | B2 | 8/2009 | Stiernborg |
| 7,641,660 | B2 | 1/2010 | Lakin et al. |
| D610,257 | S | 2/2010 | Horton |
| 7,670,345 | B2 | 3/2010 | Plassky et al. |
| 7,686,811 | B2 | 3/2010 | Byrd et al. |
| 7,691,108 | B2 | 4/2010 | Lavallee |
| 7,763,026 | B2 | 7/2010 | Egger et al. |
| 7,789,885 | B2 | 9/2010 | Metzger |
| D629,900 | S | 12/2010 | Fisher |
| 7,875,058 | B2 | 1/2011 | Holmes, Jr. |
| 7,972,338 | B2 | 7/2011 | O'Brien |
| 7,983,777 | B2 | 7/2011 | Melton et al. |
| D646,389 | S | 10/2011 | Claypool et al. |
| 8,057,473 | B2 | 11/2011 | Orsak et al. |
| 8,057,478 | B2 | 11/2011 | Kuczynski et al. |
| D651,315 | S | 12/2011 | Bertoni et al. |
| D651,316 | S | 12/2011 | May et al. |
| 8,080,010 | B2 | 12/2011 | Schulz et al. |
| 8,080,045 | B2 | 12/2011 | Wotton |
| 8,114,087 | B2 | 2/2012 | Long et al. |
| 8,123,753 | B2 | 2/2012 | Poncet |
| 8,147,530 | B2 | 4/2012 | Strnad et al. |
| 8,167,918 | B2 | 5/2012 | Strnad et al. |
| 8,172,848 | B2 | 5/2012 | Tomko et al. |
| 8,187,280 | B2 | 5/2012 | May et al. |
| 8,192,441 | B2 | 6/2012 | Collazo |
| 8,197,487 | B2 | 6/2012 | Poncet et al. |
| 8,206,153 | B2 | 6/2012 | Suttin et al. |
| 8,231,623 | B1 | 7/2012 | Jordan |
| 8,231,663 | B2 | 7/2012 | Kay et al. |
| 8,246,561 | B1 | 8/2012 | Agee et al. |
| 8,246,680 | B2 | 8/2012 | Betz et al. |
| D666,721 | S | 9/2012 | Wright et al. |
| 8,262,664 | B2 | 9/2012 | Justin et al. |
| 8,262,665 | B2 | 9/2012 | Massoud |
| 8,277,455 | B2 | 10/2012 | Couture et al. |
| 8,282,644 | B2 | 10/2012 | Edwards |
| 8,282,645 | B2 | 10/2012 | Lawrence et al. |
| 8,287,541 | B2 | 10/2012 | Nelson et al. |
| 8,292,966 | B2 | 10/2012 | Morton |
| 8,303,596 | B2 | 11/2012 | Plaky et al. |
| 8,323,281 | B2 | 12/2012 | Hotchkiss et al. |
| 8,323,289 | B2 | 12/2012 | Re |

(56) References Cited

U.S. PATENT DOCUMENTS

| | | | |
|---|---|---|---|
| 8,357,111 B2 | 1/2013 | Caillouette et al. |
| 8,377,105 B2 | 2/2013 | Bscher |
| 8,388,690 B2 | 3/2013 | Singhatat et al. |
| D679,395 S | 4/2013 | Wright et al. |
| 8,435,246 B2 | 5/2013 | Fisher et al. |
| 8,475,462 B2 | 7/2013 | Thomas et al. |
| 8,484,001 B2 | 7/2013 | Glozman et al. |
| 8,518,045 B2 | 8/2013 | Szanto |
| 8,523,870 B2 | 9/2013 | Green et al. |
| 8,529,568 B2 | 9/2013 | Bouadi |
| 8,532,807 B2 | 9/2013 | Metzger |
| 8,551,106 B2 | 10/2013 | Harrold |
| D694,884 S | 12/2013 | Mooradian et al. |
| D695,402 S | 12/2013 | Dacosta et al. |
| 8,641,721 B2 | 2/2014 | Aram et al. |
| 8,652,142 B2 | 2/2014 | Geissler |
| 8,657,820 B2 | 2/2014 | Kubiak et al. |
| D701,303 S | 3/2014 | Cook |
| 8,663,234 B2 | 3/2014 | Grimm et al. |
| 8,668,700 B2 | 3/2014 | Catanzarite et al. |
| 8,685,030 B2 | 4/2014 | Gtte et al. |
| 8,696,719 B2 | 4/2014 | Lofthouse et al. |
| 8,702,686 B2 | 4/2014 | Geebelen et al. |
| 8,702,712 B2 | 4/2014 | Jordan et al. |
| 8,715,289 B2 | 5/2014 | Smith |
| 8,715,363 B2 | 5/2014 | Ratron et al. |
| 8,728,084 B2 | 5/2014 | Berelsman et al. |
| 8,758,354 B2 | 6/2014 | Habegger et al. |
| 8,777,948 B2 | 7/2014 | Bernsteiner |
| 8,784,457 B2 | 7/2014 | Graham |
| 8,795,286 B2 | 8/2014 | Sand et al. |
| 8,808,298 B2 | 8/2014 | Raub et al. |
| 8,808,301 B1 | 8/2014 | Nofsinger |
| 8,808,302 B2 | 8/2014 | Roose et al. |
| 8,828,012 B2 | 9/2014 | May et al. |
| 8,838,263 B2 | 9/2014 | Sivak et al. |
| 8,858,602 B2 | 10/2014 | Weiner et al. |
| 8,864,773 B2 | 10/2014 | Paul et al. |
| 8,882,778 B2 | 11/2014 | Ranft |
| 8,882,816 B2 | 11/2014 | Kartalian et al. |
| 8,892,235 B2 | 11/2014 | Choi et al. |
| 8,898,043 B2 | 11/2014 | Ashby et al. |
| D720,456 S | 12/2014 | Dacosta et al. |
| 8,900,247 B2 | 12/2014 | Tseng et al. |
| 8,911,444 B2 | 12/2014 | Bailey |
| 8,920,428 B2 | 12/2014 | Zakaria et al. |
| 8,926,612 B2 | 1/2015 | Graham |
| 8,932,299 B2 | 1/2015 | Bono et al. |
| 8,939,982 B2 | 1/2015 | Chellaoui |
| 8,939,984 B2 | 1/2015 | Budoff |
| 8,945,132 B2 | 2/2015 | Play et al. |
| 8,965,075 B2 | 2/2015 | Arnaud et al. |
| 8,974,460 B2 | 3/2015 | De La Fuente et al. |
| 8,979,856 B2 | 3/2015 | Catanzarite et al. |
| 8,992,531 B2 | 3/2015 | Chow et al. |
| 8,992,532 B2 | 3/2015 | Wong |
| 8,998,903 B2 | 4/2015 | Price et al. |
| 8,998,904 B2 | 4/2015 | Zeetser et al. |
| 8,998,907 B2 | 4/2015 | Myers |
| 8,998,909 B2 | 4/2015 | Gillman et al. |
| 9,005,207 B2 | 4/2015 | Dodds et al. |
| 9,011,451 B2 | 4/2015 | Long et al. |
| 9,011,452 B2 | 4/2015 | Iannotti et al. |
| 9,011,456 B2 | 4/2015 | Ranawat et al. |
| 9,014,835 B2 | 4/2015 | Azernikov et al. |
| 9,017,329 B2 | 4/2015 | Tyber et al. |
| 9,017,336 B2 | 4/2015 | Park et al. |
| 9,023,052 B2 | 5/2015 | Lietz et al. |
| 9,044,250 B2 | 6/2015 | Olsen et al. |
| 9,060,788 B2 | 6/2015 | Bollinger |
| 9,060,822 B2 | 6/2015 | Wright et al. |
| 9,089,376 B2 | 7/2015 | Medoff et al. |
| 9,101,421 B2 | 8/2015 | Blacklidge |
| 9,107,715 B2 | 8/2015 | Blitz et al. |
| 9,113,915 B2 | 8/2015 | Thomas et al. |
| 9,113,957 B2 | 8/2015 | Axelson, Jr. et al. |
| 9,138,237 B2 | 9/2015 | Meade et al. |
| 9,138,332 B2 | 9/2015 | Harris et al. |
| D740,424 S | 10/2015 | Dacosta et al. |
| 9,173,665 B2 | 11/2015 | Couture |
| 9,173,691 B2 | 11/2015 | Orbay et al. |
| 9,186,154 B2 | 11/2015 | Li |
| 9,186,160 B1 | 11/2015 | Song |
| 9,198,678 B2 | 12/2015 | Frey et al. |
| 9,204,897 B2 | 12/2015 | Jones et al. |
| 9,211,128 B2 | 12/2015 | Gillman et al. |
| 9,220,509 B2 | 12/2015 | Boyer et al. |
| 9,220,518 B2 | 12/2015 | Neal et al. |
| 9,220,519 B2 | 12/2015 | Kaneyama et al. |
| 9,220,551 B2 | 12/2015 | Waizenegger |
| 9,232,951 B2 | 1/2016 | Johannaber |
| 9,232,955 B2 | 1/2016 | Bonin, Jr. et al. |
| 9,254,155 B2 | 2/2016 | Iannotti et al. |
| 9,295,497 B2 | 3/2016 | Schoenefeld et al. |
| 9,301,768 B2 | 4/2016 | Buza et al. |
| 9,301,783 B2 | 4/2016 | Gerold et al. |
| 9,308,006 B2 | 4/2016 | Martin et al. |
| 9,308,037 B2 | 4/2016 | Richter et al. |
| 9,320,609 B2 | 4/2016 | Schon et al. |
| 9,345,497 B2 | 5/2016 | Gonzalvez et al. |
| 9,351,738 B2 | 5/2016 | Aram et al. |
| 9,351,743 B2 | 5/2016 | Kehres et al. |
| 9,370,380 B2 | 6/2016 | Riccione |
| 9,375,220 B2 | 6/2016 | Horan et al. |
| 9,402,636 B2 | 8/2016 | Collazo |
| 9,402,640 B2 | 8/2016 | Reynolds et al. |
| 9,408,641 B2 | 8/2016 | Zhang et al. |
| 9,414,846 B2 | 8/2016 | Gillman et al. |
| 9,414,847 B2 | 8/2016 | Kurtz |
| 9,414,877 B2 | 8/2016 | Helenbolt et al. |
| 9,421,021 B2 | 8/2016 | Keppler |
| 9,427,240 B2 | 8/2016 | Von Zabern et al. |
| D765,844 S | 9/2016 | Dacosta |
| D766,434 S | 9/2016 | Dacosta |
| D766,437 S | 9/2016 | Dacosta |
| D766,438 S | 9/2016 | Dacosta |
| D766,439 S | 9/2016 | Dacosta |
| 9,433,452 B2 | 9/2016 | Weiner et al. |
| 9,445,823 B2 | 9/2016 | Harris et al. |
| 9,452,050 B2 | 9/2016 | Miles et al. |
| 9,456,902 B2 | 10/2016 | Hacking et al. |
| 9,463,034 B2 | 10/2016 | Wong et al. |
| 9,492,182 B2 | 11/2016 | Keefer |
| 9,517,145 B2 | 12/2016 | Meridew et al. |
| 9,522,023 B2 | 12/2016 | Haddad et al. |
| 9,526,514 B2 | 12/2016 | Kelley et al. |
| 9,545,276 B2 | 1/2017 | Buchanan et al. |
| 9,561,041 B2 | 2/2017 | Snider et al. |
| 9,566,103 B2 | 2/2017 | Mayer |
| 9,579,106 B2 | 2/2017 | Lo et al. |
| 9,579,107 B2 | 2/2017 | Schoenefeld |
| 9,579,112 B2 | 2/2017 | Catanzarite et al. |
| 9,592,084 B2 | 3/2017 | Grant |
| 9,603,605 B2 | 3/2017 | Collazo |
| 9,603,640 B2 | 3/2017 | Palmer et al. |
| 9,622,820 B2 | 4/2017 | Baloch et al. |
| 9,629,726 B2 | 4/2017 | Reiley et al. |
| 9,652,889 B2 | 5/2017 | Young et al. |
| 9,662,220 B2 | 5/2017 | Warburton |
| 9,668,746 B2 | 6/2017 | Lee et al. |
| 9,675,471 B2 | 6/2017 | Bojarski et al. |
| 9,687,261 B2 | 6/2017 | Serbousek et al. |
| 9,693,787 B2 | 7/2017 | Ammann et al. |
| 9,693,878 B2 | 7/2017 | Kunz et al. |
| 9,700,433 B2 | 7/2017 | Myers |
| 9,713,484 B2 | 7/2017 | Sammarco |
| 9,737,311 B2 | 8/2017 | Lavallee et al. |
| 9,737,367 B2 | 8/2017 | Steines et al. |
| 9,750,538 B2 | 9/2017 | Soffiatti et al. |
| 9,785,747 B2 | 10/2017 | Geebelen |
| 9,788,958 B2 | 10/2017 | Melamed et al. |
| 9,788,975 B2 | 10/2017 | Li |
| 9,795,392 B2 | 10/2017 | Zajac |
| 9,795,394 B2 | 10/2017 | Bonutti |

(56) References Cited

U.S. PATENT DOCUMENTS

| | | | |
|---|---|---|---|
| 9,814,474 | B2 | 11/2017 | Montoya et al. |
| 9,820,868 | B2 | 11/2017 | Witt et al. |
| 9,826,981 | B2 | 11/2017 | Schoenefeld et al. |
| 9,839,438 | B2 | 12/2017 | Eash |
| 9,848,929 | B2 | 12/2017 | Dacosta et al. |
| 9,849,019 | B2 | 12/2017 | Miller et al. |
| 9,877,754 | B2 | 1/2018 | Patel et al. |
| 9,883,954 | B1 | 2/2018 | Murphy |
| 9,888,931 | B2 | 2/2018 | Bake |
| 9,888,950 | B2 | 2/2018 | Perez et al. |
| 9,918,658 | B2 | 3/2018 | Mccaulley et al. |
| 9,918,769 | B2 | 3/2018 | Provencher et al. |
| 9,925,049 | B2 | 3/2018 | Goldstein et al. |
| 9,925,068 | B2 | 3/2018 | Bays et al. |
| 9,956,089 | B2 | 5/2018 | Kelman et al. |
| 9,968,456 | B2 | 5/2018 | Song |
| 9,980,760 | B2 | 5/2018 | Dacosta et al. |
| 9,987,092 | B2 | 6/2018 | Hladio et al. |
| 9,990,765 | B2 | 6/2018 | Ju et al. |
| 9,993,256 | B2 | 6/2018 | Lipman et al. |
| 10,002,227 | B2 | 6/2018 | Netravali et al. |
| 10,004,516 | B2 | 6/2018 | Johannaber |
| 10,010,431 | B2 | 7/2018 | Eraly et al. |
| 10,016,177 | B2 | 7/2018 | Aram et al. |
| 10,022,170 | B2 | 7/2018 | Leemrijse et al. |
| 10,028,756 | B2 | 7/2018 | Liu |
| 10,034,753 | B2 | 7/2018 | Dressler et al. |
| 10,052,114 | B2 | 8/2018 | Keppler et al. |
| 10,055,536 | B2 | 8/2018 | Maes et al. |
| 10,058,335 | B2 | 8/2018 | Lee et al. |
| 10,089,413 | B2 | 10/2018 | Wirx-Speetjens et al. |
| 10,098,761 | B2 | 10/2018 | Sherman et al. |
| 10,105,145 | B2 | 10/2018 | Lavallee |
| 10,123,807 | B2 | 11/2018 | Geebelen |
| 10,130,378 | B2 | 11/2018 | Bryan |
| 10,149,722 | B2 | 12/2018 | Aram et al. |
| 10,159,480 | B2 | 12/2018 | Tuten |
| 10,159,499 | B2 | 12/2018 | Dacosta et al. |
| 10,159,512 | B2 | 12/2018 | Robinson |
| 10,201,357 | B2 | 2/2019 | Aram et al. |
| 10,206,692 | B2 | 2/2019 | Sanders |
| 10,217,530 | B2 | 2/2019 | Couture et al. |
| 10,219,812 | B2 | 3/2019 | Torrie et al. |
| 10,226,292 | B2 | 3/2019 | Lundquist et al. |
| 10,231,745 | B2 | 3/2019 | Geebelen et al. |
| 10,238,382 | B2 | 3/2019 | Terrill et al. |
| 10,251,654 | B2 | 4/2019 | Fritzinger |
| 10,251,690 | B2 | 4/2019 | Katrana et al. |
| 10,262,084 | B2 | 4/2019 | Lavallee et al. |
| 10,265,080 | B2 | 4/2019 | Hughes et al. |
| 10,271,886 | B2 | 4/2019 | Abiven |
| 10,278,713 | B2 | 5/2019 | Richter et al. |
| 10,282,488 | B2 | 5/2019 | Eash |
| 10,286,197 | B2 | 5/2019 | Pouliot et al. |
| 10,325,065 | B2 | 6/2019 | Li et al. |
| 10,327,829 | B2 | 6/2019 | Dacosta et al. |
| 10,342,529 | B2 | 7/2019 | Fallin et al. |
| 10,350,022 | B2 | 7/2019 | Jansen et al. |
| 10,357,261 | B2 | 7/2019 | Kugler et al. |
| 10,357,299 | B2 | 7/2019 | Weiner et al. |
| 10,363,052 | B2 | 7/2019 | Park et al. |
| 10,398,510 | B2 | 9/2019 | Goto |
| 10,420,613 | B2 | 9/2019 | Azevedo Da Silva et al. |
| 10,456,205 | B2 | 10/2019 | Meridew et al. |
| 10,512,470 | B1 | 12/2019 | Bays et al. |
| 10,524,808 | B1 | 1/2020 | Hissong et al. |
| 10,524,845 | B2 | 1/2020 | Orsak et al. |
| 10,537,392 | B2 | 1/2020 | Millahn et al. |
| 10,543,100 | B2 | 1/2020 | Couture et al. |
| 10,548,667 | B2 | 2/2020 | Flett et al. |
| 10,548,668 | B2 | 2/2020 | Furrer et al. |
| 10,582,969 | B2 | 3/2020 | Couture et al. |
| 10,610,241 | B2 | 4/2020 | Wagner et al. |
| 10,631,878 | B2 | 4/2020 | Fritzinger |
| 10,631,902 | B2 | 4/2020 | Weiner et al. |
| 10,653,432 | B2 | 5/2020 | Luttrell et al. |
| 10,653,464 | B2 | 5/2020 | Hill et al. |
| 10,653,467 | B2 | 5/2020 | Brumfield et al. |
| 10,675,096 | B2 | 6/2020 | Utz et al. |
| 10,682,147 | B2 | 6/2020 | Grant et al. |
| 10,709,567 | B2 | 7/2020 | Welker et al. |
| 10,716,581 | B2 | 7/2020 | Fritzinger et al. |
| 10,722,309 | B2 | 7/2020 | Gillman |
| 10,722,310 | B2 | 7/2020 | Luby |
| 10,779,867 | B2 | 9/2020 | Penzimer et al. |
| 10,779,890 | B2 | 9/2020 | Weir |
| 10,786,291 | B2 | 9/2020 | Weiner et al. |
| 10,792,081 | B2 | 10/2020 | Weiner et al. |
| 10,806,469 | B2 | 10/2020 | Fiechter et al. |
| 10,849,665 | B2 | 12/2020 | Singh et al. |
| 10,849,670 | B2 | 12/2020 | Santrock et al. |
| 10,856,891 | B2 | 12/2020 | Rhodes et al. |
| 10,856,925 | B1 | 12/2020 | Pontell |
| 10,869,722 | B2 | 12/2020 | Caldwell et al. |
| 10,874,408 | B2 | 12/2020 | Couture |
| 10,881,416 | B2 | 1/2021 | Couture et al. |
| 10,881,417 | B2 | 1/2021 | Mahfouz |
| 10,888,340 | B2 | 1/2021 | Awtrey et al. |
| 10,905,444 | B2 | 2/2021 | Siccardi et al. |
| 10,912,574 | B2 | 2/2021 | Kim et al. |
| 10,925,622 | B2 | 2/2021 | Kehres et al. |
| 10,939,926 | B2 | 3/2021 | Kam et al. |
| 10,939,939 | B1 | 3/2021 | Gil et al. |
| 10,973,529 | B2 | 4/2021 | Lavallee et al. |
| 11,000,327 | B2 | 5/2021 | Schlotterback et al. |
| 11,020,128 | B2 | 6/2021 | Guilloux et al. |
| 11,033,336 | B2 | 6/2021 | Bohl |
| 11,065,011 | B2 | 7/2021 | Bake et al. |
| 11,074,688 | B2 | 7/2021 | Chabin et al. |
| 11,090,069 | B2 | 8/2021 | Park |
| 11,090,161 | B2 | 8/2021 | Hodorek |
| 11,112,770 | B2 | 9/2021 | Roh et al. |
| 11,116,518 | B2 | 9/2021 | Hafez |
| 11,129,625 | B2 | 9/2021 | Song et al. |
| 11,129,678 | B2 | 9/2021 | Park |
| 11,154,362 | B2 | 10/2021 | Kim et al. |
| 11,158,047 | B2 | 10/2021 | Shah |
| 11,160,567 | B2 | 11/2021 | Fallin et al. |
| 11,160,568 | B1 | 11/2021 | Park |
| 11,166,732 | B2 | 11/2021 | Maxson et al. |
| 11,172,945 | B1 | 11/2021 | Lian |
| 11,179,165 | B2 | 11/2021 | Schoenefeld |
| 11,179,168 | B2 | 11/2021 | Dacosta et al. |
| 11,207,134 | B2 | 12/2021 | Hafez |
| 11,213,305 | B2 | 1/2022 | Tannotti et al. |
| 11,213,406 | B2 | 1/2022 | Rodriguez et al. |
| 11,219,526 | B2 | 1/2022 | Mahfouz |
| 11,224,448 | B2 | 1/2022 | Bailey |
| 11,259,817 | B2 | 3/2022 | Fallin et al. |
| 11,284,909 | B2 | 3/2022 | Castricini et al. |
| 11,304,705 | B2 | 4/2022 | Fallin et al. |
| 11,304,735 | B2 | 4/2022 | Sayger et al. |
| 11,324,522 | B2 | 5/2022 | Metzger et al. |
| 11,324,607 | B2 | 5/2022 | Mauldin et al. |
| 11,331,148 | B2 | 5/2022 | Fritzinger |
| 11,331,205 | B2 | 5/2022 | Parr |
| 11,344,347 | B2 | 5/2022 | Treace et al. |
| 11,389,221 | B2 | 7/2022 | Tyber et al. |
| 11,399,849 | B2 | 8/2022 | Larche et al. |
| 11,419,726 | B2 | 8/2022 | Miller et al. |
| 11,426,184 | B2 | 8/2022 | Rivet-Sabourin et al. |
| 11,432,931 | B2 | 9/2022 | Lang |
| 11,436,801 | B2 | 9/2022 | Haslam et al. |
| 11,439,412 | B2 | 9/2022 | Woodard et al. |
| 11,457,980 | B2 | 10/2022 | Bonny et al. |
| 11,484,354 | B2 | 11/2022 | Singh et al. |
| 11,497,557 | B2 | 11/2022 | Haslam et al. |
| 11,508,102 | B2 | 11/2022 | Su et al. |
| 11,510,738 | B2 | 11/2022 | Stifter et al. |
| 11,532,402 | B2 | 12/2022 | Farley et al. |
| 11,557,036 | B2 | 1/2023 | Mansi et al. |
| 11,583,298 | B2 | 2/2023 | Robichaud et al. |
| 11,596,421 | B2 | 3/2023 | Saltzman et al. |
| 11,596,443 | B2 | 3/2023 | Treace et al. |

(56) References Cited

U.S. PATENT DOCUMENTS

| | | |
|---|---|---|
| 11,602,386 B2 | 3/2023 | Smith et al. |
| 11,607,250 B2 | 3/2023 | Treace et al. |
| 11,627,954 B2 | 4/2023 | May et al. |
| 11,628,003 B2 | 4/2023 | Nachtrab et al. |
| 11,633,195 B2 | 4/2023 | Dhillon |
| 11,648,019 B2 | 5/2023 | Bays et al. |
| 11,653,938 B2 | 5/2023 | Siegler |
| 11,684,423 B2 | 6/2023 | Jaramaz et al. |
| 11,690,725 B2 | 7/2023 | Gemon et al. |
| 11,717,359 B2 | 8/2023 | Chi |
| 11,741,277 B2 | 8/2023 | Dayal et al. |
| 11,751,892 B2 | 9/2023 | Woodard et al. |
| 11,756,051 B2 | 9/2023 | Indani et al. |
| 11,766,268 B2 | 9/2023 | Iannotti et al. |
| 11,779,467 B2 | 10/2023 | Mimnaugh et al. |
| 11,786,257 B2 | 10/2023 | Dayton et al. |
| 11,793,549 B2 | 10/2023 | Rhodes et al. |
| 11,812,978 B2 | 11/2023 | Trabish et al. |
| 11,819,223 B2 | 11/2023 | Lee |
| 11,819,224 B2 | 11/2023 | Allard et al. |
| 11,849,933 B2 | 12/2023 | Denham et al. |
| 11,849,957 B2 | 12/2023 | Couture et al. |
| 11,849,961 B2 | 12/2023 | Khatibi et al. |
| 11,849,962 B2 | 12/2023 | Singh et al. |
| 11,854,683 B2 | 12/2023 | Casey et al. |
| D1,011,524 S | 1/2024 | Santrock et al. |
| 11,857,206 B2 | 1/2024 | Robichaud et al. |
| 11,864,778 B2 | 1/2024 | Mcginley et al. |
| 11,864,959 B2 | 1/2024 | Basta |
| 11,911,046 B2 | 2/2024 | Carroll et al. |
| 11,925,417 B2 | 3/2024 | Mosnier et al. |
| 11,931,106 B2 | 3/2024 | Perler et al. |
| 11,944,546 B2 | 4/2024 | Puncreobutr et al. |
| 11,950,786 B2 | 4/2024 | Courtis et al. |
| 11,963,687 B2 | 4/2024 | Langhorn et al. |
| 11,963,703 B2 | 4/2024 | Dayton et al. |
| 11,963,729 B2 | 4/2024 | Aljuri et al. |
| 11,980,377 B2 | 5/2024 | Mauldin et al. |
| 12,004,789 B2 | 6/2024 | Mcaleer et al. |
| 12,004,814 B2 | 6/2024 | Ryan et al. |
| D1,034,985 S | 7/2024 | Hartson et al. |
| 12,035,929 B2 | 7/2024 | Athwal et al. |
| 12,045,943 B2 | 7/2024 | Chaoui et al. |
| 12,048,600 B2 | 7/2024 | Azernikov et al. |
| 12,050,999 B2 | 7/2024 | Poltaretskyi et al. |
| 12,053,242 B2 | 8/2024 | Landon et al. |
| 12,062,183 B2 | 8/2024 | Chaoui et al. |
| 12,097,129 B2 | 9/2024 | Deransart et al. |
| 12,115,083 B2 | 10/2024 | Mullen et al. |
| 12,121,272 B2 | 10/2024 | Marien et al. |
| 2002/0107519 A1 | 8/2002 | Dixon et al. |
| 2003/0236522 A1 | 12/2003 | Long et al. |
| 2004/0010259 A1 | 1/2004 | Keller et al. |
| 2004/0039394 A1 | 2/2004 | Conti et al. |
| 2004/0039396 A1 | 2/2004 | Couture et al. |
| 2004/0097946 A1 | 5/2004 | Dietzel et al. |
| 2004/0138669 A1 | 7/2004 | Horn |
| 2005/0059978 A1 | 3/2005 | Sherry et al. |
| 2005/0080424 A1 | 4/2005 | Cuckler et al. |
| 2005/0267482 A1 | 12/2005 | Hyde |
| 2005/0273112 A1 | 12/2005 | Mcnamara |
| 2006/0129163 A1 | 6/2006 | Mcguire |
| 2006/0206044 A1 | 9/2006 | Simon |
| 2006/0229621 A1 | 10/2006 | Cadmus |
| 2006/0241607 A1 | 10/2006 | Myerson et al. |
| 2006/0241608 A1 | 10/2006 | Myerson et al. |
| 2006/0264961 A1 | 11/2006 | Murray-Brown |
| 2007/0010818 A1 | 1/2007 | Stone et al. |
| 2007/0123857 A1 | 5/2007 | Deffenbaugh et al. |
| 2007/0233138 A1 | 10/2007 | Figueroa et al. |
| 2007/0265634 A1 | 11/2007 | Weinstein |
| 2007/0276383 A1 | 11/2007 | Rayhack |
| 2008/0009863 A1 | 1/2008 | Bond et al. |
| 2008/0039850 A1 | 2/2008 | Rowley et al. |
| 2008/0091197 A1 | 4/2008 | Coughlin |
| 2008/0140081 A1 | 6/2008 | Heavener et al. |
| 2008/0161815 A1 | 7/2008 | Schoenefeld et al. |
| 2008/0172054 A1 | 7/2008 | Claypool et al. |
| 2008/0288004 A1 | 11/2008 | Schendel |
| 2009/0036931 A1 | 2/2009 | Pech et al. |
| 2009/0089081 A1 | 4/2009 | Haddad |
| 2009/0093849 A1 | 4/2009 | Grabowski |
| 2009/0105767 A1 | 4/2009 | Reiley |
| 2009/0198244 A1 | 8/2009 | Leibel |
| 2009/0216089 A1 | 8/2009 | Davidson |
| 2009/0222047 A1 | 9/2009 | Graham |
| 2009/0254092 A1 | 10/2009 | Albiol Llorach |
| 2009/0254126 A1 | 10/2009 | Orbay et al. |
| 2009/0265012 A1 | 10/2009 | Engh et al. |
| 2009/0287309 A1 | 11/2009 | Walch et al. |
| 2010/0069910 A1 | 3/2010 | Hasselman |
| 2010/0130981 A1 | 5/2010 | Richards |
| 2010/0168799 A1 | 7/2010 | Schumer |
| 2010/0185202 A1 | 7/2010 | Lester et al. |
| 2010/0217270 A1 | 8/2010 | Polinski et al. |
| 2010/0256687 A1 | 10/2010 | Neufeld et al. |
| 2010/0274253 A1 | 10/2010 | Ure |
| 2010/0318088 A1 | 12/2010 | Warne et al. |
| 2011/0009865 A1 | 1/2011 | Orfaly |
| 2012/0065689 A1 | 3/2012 | Prasad et al. |
| 2012/0116203 A1 | 5/2012 | Vancraen et al. |
| 2012/0123420 A1 | 5/2012 | Honiball |
| 2012/0130434 A1 | 5/2012 | Stemniski |
| 2012/0150242 A1 | 6/2012 | Mannion |
| 2012/0191199 A1 | 7/2012 | Raemisch |
| 2012/0234329 A1 | 9/2012 | Vancraen et al. |
| 2012/0253350 A1 | 10/2012 | Anthony et al. |
| 2012/0265301 A1 | 10/2012 | Demers et al. |
| 2012/0277745 A1 | 11/2012 | Lizee |
| 2013/0211410 A1 | 8/2013 | Landes et al. |
| 2013/0236874 A1 | 9/2013 | Iannotti et al. |
| 2013/0237989 A1 | 9/2013 | Bonutti |
| 2013/0274778 A1 | 10/2013 | Mercier et al. |
| 2013/0289570 A1 | 10/2013 | Chao |
| 2013/0292870 A1 | 11/2013 | Roger |
| 2014/0005672 A1 | 1/2014 | Edwards et al. |
| 2014/0039501 A1 | 2/2014 | Schickendantz et al. |
| 2014/0074099 A1 | 3/2014 | Vigneron et al. |
| 2014/0094861 A1 | 4/2014 | Fallin |
| 2014/0163568 A1 | 6/2014 | Wong et al. |
| 2014/0257402 A1 | 9/2014 | Barsoum |
| 2014/0259629 A1 | 9/2014 | Dion et al. |
| 2014/0263674 A1 | 9/2014 | Cerveny |
| 2014/0343555 A1 | 11/2014 | Russi et al. |
| 2014/0371866 A1 | 12/2014 | Chao et al. |
| 2014/0371897 A1 | 12/2014 | Lin et al. |
| 2015/0032215 A1 | 1/2015 | Slamin et al. |
| 2015/0045903 A1 | 2/2015 | Neal |
| 2015/0066094 A1 | 3/2015 | Anderson et al. |
| 2015/0081029 A1 | 3/2015 | Bojarski et al. |
| 2015/0088142 A1 | 3/2015 | Gibson |
| 2015/0093283 A1 | 4/2015 | Miller et al. |
| 2015/0112348 A1 | 4/2015 | Schoenefeld et al. |
| 2015/0142000 A1 | 5/2015 | Seedhom et al. |
| 2015/0182342 A1 | 7/2015 | Hafez |
| 2015/0227679 A1 | 8/2015 | Kamer et al. |
| 2015/0230843 A1 | 8/2015 | Palmer et al. |
| 2015/0305752 A1 | 10/2015 | Eash |
| 2015/0342616 A1 | 12/2015 | Fryman |
| 2015/0351780 A1 | 12/2015 | Anderson et al. |
| 2015/0351916 A1 | 12/2015 | Kosarek et al. |
| 2016/0015426 A1 | 1/2016 | Dayton |
| 2016/0038161 A1 | 2/2016 | Gibson |
| 2016/0100773 A1 | 4/2016 | Ching et al. |
| 2016/0100847 A1 | 4/2016 | Maxson |
| 2016/0151165 A1 | 6/2016 | Fallin et al. |
| 2016/0175089 A1 | 6/2016 | Fallin et al. |
| 2016/0192951 A1 | 7/2016 | Gelaude et al. |
| 2016/0199198 A1 | 7/2016 | Dietz et al. |
| 2016/0256176 A9 | 9/2016 | Lowery et al. |
| 2016/0270829 A1 | 9/2016 | Duggal et al. |
| 2016/0270855 A1 | 9/2016 | Kunz et al. |
| 2016/0287395 A1 | 10/2016 | Khalili et al. |
| 2016/0338715 A1 | 11/2016 | Bojarski et al. |

(56) References Cited

U.S. PATENT DOCUMENTS

| | | |
|---|---|---|
| 2016/0354128 A1 | 12/2016 | Jeng et al. |
| 2016/0367270 A1 | 12/2016 | Garlock et al. |
| 2017/0014169 A1 | 1/2017 | Dean et al. |
| 2017/0020537 A1 | 1/2017 | Tuten |
| 2017/0027593 A1 | 2/2017 | Bojarski et al. |
| 2017/0079803 A1 | 3/2017 | Lang |
| 2017/0143511 A1 | 5/2017 | Cachia |
| 2017/0209189 A9 | 7/2017 | Hatch et al. |
| 2017/0231645 A1 | 8/2017 | Metzger et al. |
| 2017/0245906 A1 | 8/2017 | Kugler et al. |
| 2017/0245935 A1 | 8/2017 | Kugler et al. |
| 2017/0249440 A1 | 8/2017 | Lang et al. |
| 2017/0281353 A1 | 10/2017 | Al Hares et al. |
| 2017/0360578 A1 | 12/2017 | Shin et al. |
| 2018/0021145 A1 | 1/2018 | Seavey et al. |
| 2018/0028325 A1 | 2/2018 | Bojarski et al. |
| 2018/0049758 A1 | 2/2018 | Amis et al. |
| 2018/0116804 A1 | 5/2018 | Hafez et al. |
| 2018/0221071 A1 | 8/2018 | Isch |
| 2018/0235706 A1 | 8/2018 | Asseln et al. |
| 2018/0242987 A1 | 8/2018 | Lintula et al. |
| 2018/0289423 A1 | 10/2018 | Singh et al. |
| 2018/0317986 A1 | 11/2018 | Jackman et al. |
| 2018/0344326 A1 | 12/2018 | Chan et al. |
| 2019/0000629 A1 | 1/2019 | Winslow |
| 2019/0008532 A1 | 1/2019 | Fitz et al. |
| 2019/0117239 A1 | 4/2019 | Verma |
| 2019/0175277 A1 | 6/2019 | Chav et al. |
| 2019/0175351 A1 | 6/2019 | Bojarski et al. |
| 2019/0307495 A1 | 10/2019 | Geldwert |
| 2019/0365543 A1 | 12/2019 | Slamin et al. |
| 2020/0008813 A1 | 1/2020 | Bonny et al. |
| 2020/0046425 A1 | 2/2020 | Lopes et al. |
| 2020/0100909 A1 | 4/2020 | Lang et al. |
| 2020/0155323 A1 | 5/2020 | Lang et al. |
| 2020/0163721 A1 | 5/2020 | Aghazadeh |
| 2020/0214719 A1 | 7/2020 | Fraone et al. |
| 2020/0253641 A1* | 8/2020 | Treace ................. A61B 17/025 |
| 2020/0337714 A1 | 10/2020 | Hafez et al. |
| 2020/0356073 A1 | 11/2020 | Tokushima |
| 2020/0405322 A1 | 12/2020 | Brailovski et al. |
| 2021/0007760 A1 | 1/2021 | Reisin |
| 2021/0022781 A1 | 1/2021 | Dacosta et al. |
| 2021/0030429 A1 | 2/2021 | Rose et al. |
| 2021/0045756 A1 | 2/2021 | Zakhary et al. |
| 2021/0059691 A1 | 3/2021 | Zille |
| 2021/0059837 A1 | 3/2021 | Rhodes |
| 2021/0077120 A1 | 3/2021 | Hatch et al. |
| 2021/0077192 A1 | 3/2021 | Perler et al. |
| 2021/0085338 A1 | 3/2021 | Dacosta et al. |
| 2021/0090248 A1 | 3/2021 | Choi et al. |
| 2021/0106427 A1 | 4/2021 | Mahfouz |
| 2021/0113223 A1 | 4/2021 | Schaumann et al. |
| 2021/0121297 A1 | 4/2021 | Cavanagh et al. |
| 2021/0137537 A1 | 5/2021 | Zille |
| 2021/0161543 A1 | 6/2021 | Mcauliffe et al. |
| 2021/0186704 A1 | 6/2021 | Fitz et al. |
| 2021/0192759 A1 | 6/2021 | Lang |
| 2021/0196290 A1 | 7/2021 | Tannotti et al. |
| 2021/0212705 A1 | 7/2021 | Reynolds et al. |
| 2021/0219989 A1 | 7/2021 | Chao |
| 2021/0244477 A1 | 8/2021 | Singh et al. |
| 2021/0256171 A1 | 8/2021 | Hosseini |
| 2021/0275196 A1 | 9/2021 | Wodajo |
| 2021/0282790 A1 | 9/2021 | Sellman et al. |
| 2021/0282823 A1 | 9/2021 | Day et al. |
| 2021/0290250 A1 | 9/2021 | Denham et al. |
| 2021/0298766 A1 | 9/2021 | Loring et al. |
| 2021/0307833 A1 | 10/2021 | Farley et al. |
| 2021/0307834 A1 | 10/2021 | Gillman et al. |
| 2021/0346038 A1 | 11/2021 | Fiechter et al. |
| 2021/0378752 A1 | 12/2021 | Paul et al. |
| 2021/0386437 A1 | 12/2021 | Dacosta et al. |
| 2021/0391058 A1 | 12/2021 | Kostrzewski et al. |
| 2021/0393304 A1 | 12/2021 | Geldwert |

| | | |
|---|---|---|
| 2022/0039965 A1 | 2/2022 | Casey et al. |
| 2022/0087822 A1 | 3/2022 | Radermacher et al. |
| 2022/0096157 A1 | 3/2022 | Pollock et al. |
| 2022/0133484 A1 | 5/2022 | Lang |
| 2022/0160405 A1 | 5/2022 | Casey et al. |
| 2022/0167998 A1 | 6/2022 | Siccardi et al. |
| 2022/0192685 A1 | 6/2022 | Gazonnet et al. |
| 2022/0202495 A1 | 6/2022 | Pack |
| 2022/0211387 A1 | 7/2022 | Perler et al. |
| 2022/0233203 A1 | 7/2022 | Rhodes et al. |
| 2022/0249106 A1 | 8/2022 | Akallal et al. |
| 2022/0249143 A1 | 8/2022 | Hollis et al. |
| 2022/0270762 A1 | 8/2022 | Crawford et al. |
| 2022/0273450 A1 | 9/2022 | Steines et al. |
| 2022/0296285 A1 | 9/2022 | Besque et al. |
| 2022/0313284 A1 | 10/2022 | Korman |
| 2022/0323086 A1 | 10/2022 | Stemniski et al. |
| 2022/0338934 A1 | 10/2022 | Perler et al. |
| 2022/0346806 A1 | 11/2022 | Leemrijse et al. |
| 2023/0013727 A1 | 1/2023 | Korman et al. |
| 2023/0014384 A1 | 1/2023 | Cordonnier et al. |
| 2023/0077222 A1 | 3/2023 | Awtrey |
| 2023/0157705 A1 | 5/2023 | Reynolds |
| 2023/0190306 A1 | 6/2023 | Kowalczyk et al. |
| 2023/0281842 A1 | 9/2023 | Ribeiro et al. |
| 2023/0310013 A1 | 10/2023 | Perler et al. |
| 2023/0310051 A1 | 10/2023 | Hafez et al. |
| 2023/0363773 A1 | 11/2023 | Perler et al. |
| 2023/0371966 A1 | 11/2023 | Spitler |
| 2023/0389937 A1 | 12/2023 | Penner et al. |
| 2023/0404673 A1 | 12/2023 | Spitler et al. |
| 2024/0005504 A1 | 1/2024 | Ribeiro et al. |
| 2024/0008880 A1 | 1/2024 | Spitler et al. |
| 2024/0099778 A1 | 3/2024 | Hlad et al. |
| 2024/0108414 A1 | 4/2024 | Dreyer et al. |

FOREIGN PATENT DOCUMENTS

| | | |
|---|---|---|
| AU | 2015203808 B2 | 9/2017 |
| AU | 2020220169 A1 | 9/2020 |
| AU | 2021286392 A1 | 1/2022 |
| CA | 2491824 A1 | 9/2005 |
| CA | 2608464 C | 7/2012 |
| CA | 2854997 A1 | 5/2013 |
| CA | 2713309 C | 7/2013 |
| CH | 695846 A5 | 9/2006 |
| CN | 2930668 Y | 8/2007 |
| CN | 201558162 U | 8/2010 |
| CN | 201572172 U | 9/2010 |
| CN | 201586060 U | 9/2010 |
| CN | 201912210 U | 8/2011 |
| CN | 101237835 B | 11/2012 |
| CN | 202801773 U | 3/2013 |
| CN | 103462675 A | 12/2013 |
| CN | 103505276 A | 1/2014 |
| CN | 203458450 U | 3/2014 |
| CN | 102860860 B | 5/2014 |
| CN | 203576647 U | 5/2014 |
| CN | 104490460 A | 4/2015 |
| CN | 104510523 A | 4/2015 |
| CN | 104523327 A | 4/2015 |
| CN | 104546102 A | 4/2015 |
| CN | 204379413 U | 6/2015 |
| CN | 204410951 U | 6/2015 |
| CN | 204428143 U | 7/2015 |
| CN | 204428144 U | 7/2015 |
| CN | 204428145 U | 7/2015 |
| CN | 204446081 U | 7/2015 |
| CN | 106236185 A | 12/2016 |
| CN | 205924106 U | 2/2017 |
| CN | 206151532 U | 5/2017 |
| CN | 105105853 B | 7/2017 |
| CN | 108030532 A | 5/2018 |
| CN | 207721902 U | 8/2018 |
| CN | 112914724 B | 2/2022 |
| CN | 117297772 B | 2/2024 |
| CN | 117322951 B | 2/2024 |
| CN | 109223098 B | 5/2024 |
| DE | 2910627 A1 | 9/1980 |

(56) References Cited

FOREIGN PATENT DOCUMENTS

| DE | 202006010241 U1 | 3/2007 |
|----|----|----|
| DE | 102007053058 B3 | 4/2009 |
| EP | 685206 B1 | 9/2000 |
| EP | 1508316 B1 | 5/2007 |
| EP | 1897509 B1 | 7/2009 |
| EP | 2124832 B1 | 8/2012 |
| EP | 2750617 A1 | 7/2014 |
| EP | 2856951 A1 | 4/2015 |
| EP | 2624764 B1 | 12/2015 |
| EP | 3000443 A3 | 7/2016 |
| EP | 2083758 B1 | 11/2017 |
| EP | 2632349 B1 | 3/2018 |
| EP | 3013256 B1 | 11/2018 |
| EP | 3171795 B1 | 11/2018 |
| EP | 3672535 A1 | 7/2020 |
| EP | 2558010 B1 | 5/2021 |
| EP | 3948895 A1 | 2/2022 |
| EP | 3740141 B1 | 4/2022 |
| EP | 2844162 B1 | 7/2022 |
| FR | 2362616 A1 | 3/1978 |
| FR | 2764183 A1 | 12/1998 |
| FR | 2953120 B1 | 1/2012 |
| FR | 3030221 A1 | 6/2016 |
| FR | 3117328 B1 | 3/2023 |
| GB | 2154143 A | 9/1985 |
| GB | 2154144 A | 9/1985 |
| GB | 2334214 B | 1/2003 |
| GB | 2589960 A | 6/2021 |
| JP | S635739 A | 1/1988 |
| JP | 2004174265 A | 6/2004 |
| JP | 2006158972 A | 6/2006 |
| JP | 4134243 B2 | 8/2008 |
| JP | 2011092405 A | 5/2011 |
| JP | 4796943 B2 | 10/2011 |
| JP | 2014511207 A | 5/2014 |
| JP | 2014521384 A | 8/2014 |
| KR | 100904142 B1 | 6/2009 |
| KR | 1020160090006 A | 7/2016 |
| KR | 1020180118476 A | 10/2018 |
| KR | 101952368 B1 | 2/2019 |
| MD | 756 B1 | 7/1997 |
| RU | 2098036 C1 | 12/1997 |
| RU | 2195892 C2 | 1/2003 |
| RU | 2320287 C1 | 3/2008 |
| RU | 2321366 C2 | 4/2008 |
| RU | 2321369 C1 | 4/2008 |
| RU | 2346663 C2 | 2/2009 |
| RU | 2412662 C1 | 2/2011 |
| RU | 182499 U1 | 8/2018 |
| RU | 2789960 C2 | 2/2023 |
| SU | 1333328 A2 | 8/1987 |
| WO | 0166022 A1 | 9/2001 |
| WO | 03075775 A1 | 9/2003 |
| WO | 2004089227 A2 | 10/2004 |
| WO | 2008051064 A1 | 5/2008 |
| WO | 2009001083 A1 | 12/2008 |
| WO | 2009029798 A1 | 3/2009 |
| WO | 2009032101 A2 | 3/2009 |
| WO | 2010099231 A3 | 11/2010 |
| WO | 2011005327 A1 | 1/2011 |
| WO | 2011037885 A1 | 3/2011 |
| WO | 2012024317 A2 | 2/2012 |
| WO | 2012029008 A1 | 3/2012 |
| WO | 2012176077 A1 | 12/2012 |
| WO | 2013026786 A1 | 2/2013 |
| WO | 2013041618 A1 | 3/2013 |
| WO | 2013134387 A1 | 9/2013 |
| WO | 2013156816 A2 | 10/2013 |
| WO | 2014020561 A1 | 2/2014 |
| WO | 2014020562 A1 | 2/2014 |
| WO | 2014022055 A1 | 2/2014 |
| WO | 2014085882 A1 | 6/2014 |
| WO | 2014147099 A1 | 9/2014 |
| WO | 2014152219 A2 | 9/2014 |
| WO | 2014200017 A1 | 12/2014 |
| WO | 2015003284 A2 | 1/2015 |
| WO | 2015094409 A1 | 6/2015 |
| WO | 2015127515 A2 | 9/2015 |
| WO | 2016012731 A1 | 1/2016 |
| WO | 2016102025 A1 | 6/2016 |
| WO | 2017031000 A1 | 2/2017 |
| WO | 2017122076 A2 | 7/2017 |
| WO | 2017151833 A1 | 9/2017 |
| WO | 2018167369 A1 | 9/2018 |
| WO | 2019060780 A2 | 3/2019 |
| WO | 2019052622 A4 | 5/2019 |
| WO | 2019180747 A1 | 9/2019 |
| WO | 2020060349 A1 | 3/2020 |
| WO | 2021054518 A1 | 3/2021 |
| WO | 2021091071 A1 | 5/2021 |
| WO | 2021118733 A1 | 6/2021 |
| WO | 2021127625 A1 | 6/2021 |
| WO | 2021240290 A1 | 12/2021 |
| WO | 2022155208 A1 | 7/2022 |
| WO | 2022182312 A1 | 9/2022 |
| WO | 2023096516 A1 | 6/2023 |
| WO | 2024025840 A1 | 2/2024 |

OTHER PUBLICATIONS

Defendant Fusion Orthopedics LLC's Invalidity Contentions, No. CV-22-00490-PHX-SRB, US District Court for the District of Arizona, Aug. 27, 2022, 41 pages.

Didomenico et al., "Correction of Frontal Plane Rotation of Sesamoid Apparatus during the Lapidus Procedure: A Novel Approach," The Journal of Foot and Ankle Surgery, vol. 53, 2014, pp. 248-251.

Didomenico et al., "Lapidus Bunionectomy: First Metatarsal-Cuneiform Arthrodesis," McGlamrys Comprehensive Textbook of Foot and Ankle Surgery, Fourth Edition, vol. 1, Chapter 31, 2013, 24 pages.

Dinapoli et al., "Metatarsal Osteotomy for the Correction of Metatarsus Adductus," Reconstructive Surgery of the Foot and Leg, 1989, pp. 242-250.

Disior, "Bonelogic Foot & Ankle Module" , https://www.disior.com/foot--ankle.html, Downloaded Jun. 1, 2022, p. 6.

Dobbe et al. "Patient-Tailored Plate For Bone Fixation And Accurate 3D Positioning In Corrective Osteotomy," Medical and Biological Engineering and Computing, vol. 51, No. 1-2, Feb. 2013, pp. 19-27, (Abstract Only).

Doty et al., "Hallux valgus and hypermobility of the first ray: facts and fiction," International Orthopaedics, vol. 37, 2013, pp. 1655-1660.

Dubovik et al., "Talonavicular Joint Arthrodesis and Medial Displacement Calcaneal Osteotomy for Treatment of Patients With Planovalgus Deformity" Traumatology and Orthopedics of Russia, vol. 18, No. 3, Sep. 30, 2012, pp. 83-88.

Easley et al., "Current Concepts Review: Hallux Valgus Part I: Pathomechanics, Clinical Assessment, and Nonoperative Management," Foot and Ankle International, vol. 28, No. 5, May 2007, pp. 654-659.

Easley et al., "Current Concepts Review: Hallux Valgus Part II: Operative Treatment," Foot and Ankle International, vol. 28, No. 6, Jun. 2007, pp. 748-758.

Easley et al., "What is the Best Treatment for Hallux Valgus?," Evidence-Based Orthopaedics—The Best Answers to Clinical Questions, Chapter 73, 2009, pp. 479-491.

EBI Extra Small Rail Fixator, Biomet Trauma, retrieved Dec. 19, 2014, from the Internet: <http://footandanklefixation.com/product/biomet-trauma-ebi-extra-small-rail-fixator>, 7 pages.

Holmes, Jr., "Correction of the Intermetatarsal Angle Component of Hallux Valgus Using Fiberwire-Attached Endo-buttons," Revista Internacional de Ciencias Podologicas, vol. 6, No. 2, 2012, pp. 73-79.

Eustace et al., "Hallux valgus, first metatarsal pronation and collapse of the medial longitudinal arch—a radiological correlation," Skeletal Radiology, vol. 23, 1994, pp. 191-194.

Fallin et al., US Provisional Application Entitled Indexed Tri-Planar Osteotomy Guide and Method, U.S. Appl. No. 62/118,378, filed Feb. 19, 2015, 62 pages.

(56)          References Cited

OTHER PUBLICATIONS

Fazal et al., "First metatarsophalangeal joint arthrodesis with two orthogonal two hole plates," Acta Orthopaedica et Traumatologica Turcica, vol. 52, 2018, pp. 363-366.

Feilmeier et al., "Incidence of Surgical Site Infection in the Foot and Ankle with Early Exposure and Showering of Surgical Sites: A Prospective Observation," The Journal of Foot and Ankle Surgery, vol. 53, 2014, pp. 173-175.

Feilmeier et al., "Reduction of Intermetatarsal Angle after First Metatarsophalangeal Joint Arthrodesis in Patients with Hallux Valgus," The Journal of Foot and Ankle Surgery, vol. 53, 2014, pp. 29-31.

Ferrari et al., "A Radiographic Study of the Relationship Between Metatarsus Adductus and Hallux Valgus," The Journal of Foot and Ankle Surgery, vol. 42, No. 1, 2003, pp. 9-14.

Ferreyra et al., "Can we correct first metatarsal rotation and sesamoid position with the 3D Lapidus procedure?," Foot and Ankle Surgery, vol. 28, No. 3, Apr. 2022, pp. 313-318.

Fibretuff, "3D Printing, CNC Machining, Molding and Extruding Biocompatible material's with "bone like" Qualities for 3D Printing" https://fibretuff.us, Downloaded Feb. 24, 2023, pp. 22.

Fishco, "A Straightforward Guide to the Lapidus Bunionectomy, " Podiatry Today, Retrieved online from <https://www.hmpglobal-learningnetwork.com/site/podiatry/blogged/straightforward-guide-lapidus-bunionectomy>, dated Sep. 6, 2013, 5 pages.

Fishco, "Making the Lapidus Easy," The Podiatry Institute, Update 2014, Chapter 14, 2014, pp. 91-93.

Flavin et al., "Arthrodesis of the First Metatarsophalangeal Joint Using a Dorsal Titanium Contoured Plate," Foot & Ankle International, vol. 25, No. 11, Nov. 2004, pp. 783-787.

Fleming et al., "Results of Modified Lapidus Arthrodesis Procedure Using Medial Eminence as an Interpositional Autograft," The Journal of Foot & Ankle Surgery, vol. 50, 2011, pp. 272-275.

Fraissler et al., "Treatment of hallux valgus deformity," Efort Open Reviews, vol. 1, Aug. 2016, pp. 295-302.

Fuhrmann, "Arthrodesis of the First Tarsometatarsal Joint for Correction of the Advanced Splayfoot Accompanied by a Hallux Valgus," Operative Orthopadie und Traumatologie, No. 2, 2005, pp. 195-210.

Galli et al., "Enhanced Lapidus Arthrodesis: Crossed Screw Technique With Middle Cuneiform Fixation Further Reduces Sagittal Mobility," The Journal of Foot & Ankle Surgery, vol. 54, vol. 3, May/Jun. 2015, pp. 437-440.

Garthwait, "Accu-Cut System Facilitates Enhanced Precision," Podiatry Today, vol. 18, No. 6, Jun. 2005, 6 pages.

Gerard et al., "The Modified Lapidus Procedure," Orthopedics, vol. 31, No. 3, Mar. 2008, 7 pages.

Ghali et al., "The Management of Metatarsus Adductus et Supinatus," The Journal of Bone and Joint Surgery, vol. 66-B, No. 3, May 1984, pp. 376-380.

Giannoudis et al., "Hallux Valgus Correction," Practical Procedures in Elective Orthopaedic Surgery, Pelvis and Lower Extremity, Chapter 38, 2012, 22 pages.

Gonzalez Del Pino et al., "Variable Angle Locking Intercarpal Fusion System for Four-Corner Arthrodesis: Indications and Surgical Technique," Journal of Wrist Surgery, vol. 1, No. 1, Aug. 2012, pp. 73-78.

Gotte, "Entwicklung eines Assistenzrobotersystems fr die Knieendoprothetik," Forschungsberichte, Technische Universitat Munchen, 165, 2002, 11 pages, including partial English Translation.

Gould et al., "A Prospective Evaluation of First Metatarsophalangeal Fusion Using an Innovative Dorsal Compression Plating System," The Journal of Foot & Ankle Surgery, vol. 60, 2021, pp. 891-896.

Gregg et al., "Plantar plate repair and Weil osteotomy for metatarsophalangeal joint instability," Foot and Ankle Surgery, vol. 13, 2007, pp. 116-121.

Greiner, "The Jargon of Pedal Movements," Foot & Ankle International, vol. 28, No. 1, Jan. 2007, pp. 109-125.

Grondal et al., "A Guide Plate for Accurate Positioning of First Metatarsophalangeal Joint during Fusion," Operative Orthopdie Und Traumatologie, vol. 16, No. 2, 2004, pp. 167-178 (Abstract Only).

Groves, "Functional Position Joint Sectioning: Pre-Load Method for Lapidus Arthrodesis," The Podiatry Institute, Update 2015, Chapter 6, 2015, pp. 23-29.

Groves, "Operative Report," St. Tammany Parish Hospital, Date of Procedure, Mar. 26, 2014, 2 pages.

Gutteck et al., "Comparative study of Lapidus bunionectomy using different osteosynthesis methods," Foot and Ankle Surgery, vol. 19, 2013, pp. 218-221.

Gutteck et al., "Is it feasible to rely on intraoperative X ray in correcting hallux valgus?," Archives of Orthopaedic and Trauma Surgery, vol. 133, 2013, pp. 753-755.

Hardy et al., "Observations on Hallux Valgus," The Journal of Bone and Joint Surgery, vol. 33B, No. 3, Aug. 1951,pp. 376-391.

Hatch et al., "Analysis of Shortening and Elevation of the First Ray With Instrumented Triplane First Tarsometatarsal Arthrodesis," Foot & Ankle Orthopaedics, vol. 5, No. 4, 2020, pp. 1-8.

Hatch et al., "Triplane Hallux Abducto Valgus Classification," The Journal of Foot & Ankle Surgery, vol. 57, No. 5, September/Oct. 2018, published online: May 18, 2018, pp. 972-981.

Hetherington et al., "Evaluation of surgical experience and the use of an osteotomy guide on the apical angle of an Austin osteotomy," The Foot, vol. 18, 2008, pp. 159-164.

Hirao et al., "Computer assisted planning and custom-made surgical guide for malunited pronation deformity after first metatarsophalangeal joint arthrodesis in rheumatoid arthritis: A case report," Computer Aided Surgery, vol. 19, Nos. 1-3, 2014, pp. 13-19.

Ho et al., "Hallux rigidus," Efort Open Reviews, vol. 2, Jan. 2017, pp. 13-20.

D'Amico et al., "Motion of the First Ray: Clarification Through Investigation," Journal of the American Podiatry Association, vol. 69, No. 1, Jan. 1979, pp. 17-23.

Dayton et al., "Biwinged Excision for Round Pedal Lesions," The Journal of Foot and Ankle Surgery, vol. 35, No. 3, 1996, pp. 244-249.

Coughlin "Proximal Metatarsal Osteotomy and Distal Soft Tissue Reconstruction for Hallux Valgus in Juveniles" Orthopaedics and Traumatology, vol. 7, Published: Jun. 1999, pp. 133-143.

Dayton et al., "Medial Incision Approach to the First Metatarsophalangeal Joint," The Journal of Foot and Ankle Surgery, vol. 40, No. 6, Nov./Dec. 2001, pp. 414-417.

Dayton et al., "Reduction of the Intermetatarsal Angle after First Metatarsophalangeal Joint Arthrodesis in Patients with Moderate and Severe Metatarsus Primus Adductus," The Journal of Foot and Ankle Surgery, vol. 41, No. 5, Sep./Oct. 2002, pp. 316-319.

Dayton et al., "Use of the Z Osteotomy for Tailor Bunionectomy," The Journal of Foot and Ankle Surgery, vol. 42, No. 3, May/Jun. 2003, pp. 167-169.

Dayton et al., "Early Weightbearing After First Metatarsophalangeal Joint Arthrodesis: A Retrospective Observational Case Analysis," The Journal of Foot and Ankle Surgery, vol. 43, No. 3, May/Jun. 2004, pp. 156-159.

Dayton et al., "Dorsal Suspension Stitch: An Alternative Stabilization After Flexor Tenotomy for Flexible Hammer Digit Syndrome," The Journal of Foot and Ankle Surgery, vol. 48, No. 5, Sep./Oct. 2009, pp. 602-605.

Dayton et al., "The Extended Knee Hemilithotomy Position for Gastrocnemius Recession," The Journal of Foot and Ankle Surgery, vol. 49, 2010, pp. 214-216.

Dayton et al., "A User-Friendly Method of Pin Site Management for External Fixators," Foot and Ankle Specialist, Sep. 16, 2011, 4 pages.

Dayton et al., "Hallux Varus as Complication of Foot Compartment Syndrome," The Journal of Foot and Ankle Surgery, vol. 50, 2011, pp. 504-506.

Dayton et al., "Measurement of Mid-Calcaneal Length on Plain Radiographs: Reliability of a New Method," Foot and Ankle Specialist, vol. 4, No. 5, Oct. 2011, pp. 280-283.

(56) References Cited

OTHER PUBLICATIONS

Cottom, "Fixation of the Lapidus Arthrodesis with a Plantar Interfragmentary Screw and Medial Low Profile Locking Plate," The Journal of Foot & Ankle Surgery, vol. 51, 2012, pp. 517-522.

Dayton et al., "Does Postoperative Showering or Bathing of a Surgical Site Increase the Incidence of Infection? A Systematic Review of the Literature," The Journal of Foot and Ankle Surgery, vol. 52, 2013, pp. 612-614.

Dayton et al., "Effectiveness of a Locking Plate in Preserving Midcalcaneal Length and Positional Outcome after Evans Calcaneal Osteotomy: A Retrospective Pilot Study," The Journal of Foot and Ankle Surgery, vol. 52, 2013, pp. 710-713.

Dayton et al., "Principles of Management of Growth Plate Fractures in the Foot and Ankle," Clinics in Podiatric Medicine and Surgery, Pediatric Foot Deformities, Oct. 2013, 17 pages.

Crawford et al. "Metatarsus Adductus: Radiographic and Pathomechanical Analysis" Chapter 5, https://www.podiatryinstitute.com/pdfs/Update_2014/2014_05.pdf, Published 2014, pp. 25-30.

Dayton et al., "Clarification of the Anatomic Definition of the Bunion Deformity," The Journal of Foot and Ankle Surgery, vol. 53, 2014, pp. 160-163.

Dayton et al., "Observed Changes in First Metatarsal and Medial Cuneiform Positions after First Metatarsophalangeal Joint Arthrodesis," The Journal of Foot and Ankle Surgery, vol. 53, 2014, pp. 32-35.

Dayton et al., "Observed Changes in Radiographic Measurements of the First Ray after Frontal Plane Rotation of the First Metatarsal in a Cadaveric Foot Model," The Journal of Foot and Ankle Surgery, Article in Press, 2014, 5 pages.

Dayton et al., "Observed Changes in Radiographic Measurements of the First Ray after Frontal and Transverse Plane Rotation of the Hallux: Does the Hallux Drive the Metatarsal in a Bunion Deformity?," The Journal of Foot and Ankle Surgery, Article in Press, 2014, 4 pages.

Dayton et al., "Observed Changes in Radiographic Measurements of the First Ray after Frontal and Transverse Plane Rotation of the Hallux: Does the Hallux Drive the Metatarsal in a Bunion Deformity?," The Journal of Foot and Ankle Surgery, vol. 53, 2014, pp. 584-587.

Dayton et al., "Reduction of the Intermetatarsal Angle after First Metatarsal Phalangeal Joint Arthrodesis: A Systematic Review," The Journal of Foot and Ankle Surgery, Article in Press, 2014, 4 pages.

Dayton et al., "Technique for Minimally Invasive Reduction of Calcaneal Fractures Using Small Bilateral External Fixation," The Journal of Foot and Ankle Surgery, Article in Press, 2014, 7 pages.

Dayton, "Tarsal-Metatarsal Joint: Primary & Revision Arthrodesis" Disclosure: Speaker for Orthofix and Biomet, Apr. 2014, pp. 38.

Dalat et al. "Does arthrodesis of the first metatarsophalangeal joint correct the intermetatarsal M1M2 angle? Analysis of a continuous series of 208 arthrodeses fixed with plates" Orthopaedics & Traumatology: Surgery & Research 101, 2015, pp. 709-714.

Dayton et al., "A new triplanar paradigm for bunion management," Lower Extremity Review, Apr. 2015, 9 pages.

Dayton et al., "Comparison of Complications for Internal and External Fixation for Charcot Reconstruction: A Systematic Review," The Journal of Foot and Ankle Surgery, Article in Press, 2015, 4 pages.

Dayton et al., "Complications of Metatarsal Suture Techniques for Bunion Correction: A Systematic Review of the Literature," The Journal of Foot and Ankle Surgery, Article in Press, 2015, 3 pages.

Dayton et al., "Is Our Current Paradigm for Evaluation and Management of the Bunion Deformity Flawed? A Discussion of Procedure Philosophy Relative to Anatomy," The Journal of Foot and Ankle Surgery, vol. 54, 2015, pp. 102-111.

Dayton et al., "Quantitative Analysis of the Degree of Frontal Rotation Required to Anatomically Align the First Metatarsal Phalangeal Joint During Modified Tarsal-Metatarsal Arthrodesis Without Capsular Balancing," The Journal of Foot and Ankle Surgery, 2015, pp. 1-6.

Dayton et al. "Comparison of Tibial Sesamoid Position on Anteroposterior and Axial Radiographs Before and After Triplane Tarsal Metatarsal Joint Arthrodesis" The Journal of Foot & Ankle Surgery 56, 2017, pp. 1041-1046.

Dayton "Evidence-Based Bunion Surgery: A Critical Examination of Current and Emerging Concepts and Techniques" Springer International Publishing, 2017, pp. 254.

Dayton et al. "Biomechanical Characteristics of Biplane Multiplanar Tension-Side Fixation for Lapidus Fusion" The Journal of Foot & Ankle Surgery, 2018, pp. 1-5.

Dayton et al. "Progression of Healing on Serial Radiographs Following First Ray Arthrodesis in the Foot Using a Biplanar Plating Technique Without Compression" The Journal of Foot & Ankle Surgery, 2018, pp. 1-7.

Cruz et al., "Does Hallux Valgus Exhibit a Deformity Inherent to the First Metatarsal Bone?" The Journal of Foot & Ankle Surgery, vol. 58, No. 6, Nov. 2019, pp. 1210-1214.

Dahlgren et al., "First Tarsometatarsal Fusion Using Saw Preparation vs. Standard Preparation of the Joint: A Cadaver Study," Foot & Ankle Orthopaedics, vol. 4, No. 4, Oct. 2019, 2 pages.

Conti et al., "Effect of the Modified Lapidus Procedure for Hallux Valgus on Foot Width," Foot & Ankle International, Feb. 1, 2020, published online: Oct. 30, 2019, 6 pages.

Conti et al., "Effect of the Modified Lapidus Procedure on Pronation of the First Ray in Hallux Valgus," Foot & Ankle International, Feb. 1, 2020, published online: Oct. 16, 2019, 8 pages.

Dayton et al. "Comparison of Radiographic Measurements Before and After Triplane Tarsometatarsal Arthrodesis for Hallux Valgus" The Journal of Foot & Ankle Surgery 59, 2020, pp. 291-297.

Curran et al. "Functional Capabilities After First Metatarsal Phalangeal Joint Arthrodesis Using a Locking Plate and Compression Screw Construct" The Journal of Foot & Ankle Surgery, 2021, pp. 1-5.

De Carvalho, et al. "Automated Three-dimensional distance and coverage mapping of hallux valgus: a case- control study" Journal of Foot and Ankle, 2022; 16(1), pp. 5.

Dayton et al., "Comparison of the Mechanical Characteristics of a Universal Small Biplane Plating Technique Without Compression Screw and Single Anatomic Plate With Compression Screw," The Journal of Foot & Ankle Surgery, vol. 55, No. 3, May/Jun. 2016, published online: Feb. 9, 2016, pp. 567-571.

Dayton et al., "Relationship of Frontal Plane Rotation of First Metatarsal to Proximal Articular Set Angle and Hallux Alignment in Patients Undergoing Tarsometatarsal Arthrodesis for Hallux Abducto Valgus: A Case Series and Critical Review of the Literature," The Journal of Foot & Ankle Surgery, 2013, Article in Press, Mar. 1, 2013, 7 pages.

Dayton et al., "Relationship of Frontal Plane Rotation of First Metatarsal to Proximal Articular Set Angle and Hallux Alignment in Patients Undergoing Tarsometatarsal Arthrodesis for Hallux Abducto Valgus: A Case Series and Critical Review of the Literature," The Journal of Foot and Ankle Surgery, vol. 52, No. 3, May/Jun. 2013, pp. 348-354.

De Geer et al., "A New Measure of Tibial Sesamoid Position in Hallux Valgus in Relation to the Coronal Rotation of the First Metatarsal in CT Scans," Foot and Ankle International, Mar. 26, 2015, 9 pages.

De Heer et al., "Procedure-Specific Hardware Removal After Evans Osteotomy" Journal of the American Podiatric Medical Association, vol. 110, No. 2, Mar./Apr. 2020, pp. 1-7.

Decarbo et al., "Locking Plates: Do They Prevent Complications?," Podiatry Today, Apr. 2014, 7 pages.

Decarbo et al., "Resurfacing Interpositional Arthroplasty for Degenerative Joint Disease of the First Metatarsalphalangeal Joint," Podiatry Management, Jan. 2013, pp. 137-142.

Wendl et al., "Navigation in der Knieendoprothetik," OP-Journal, vol. 17, 2002, pp. 22-27, including English Abstract.

Whipple et al., "Zimmer Herbert Whipple Bone Screw System: Surgical Techniques for Fixation of Scaphoid and Other Small Bone Fractures," Zimmer, 2003, 59 pages.

Weber et al., "A Simple System for Navigation of Bone Alignment Osteotomies of the Tibia," International Congress Series, vol. 1268, Jan. 2004, pp. 608-613, (Abstract Only).

(56) References Cited

OTHER PUBLICATIONS

Wukich et al., "Hypermobility of the First Tarsometatarsal Joint," Foot and Ankle Clinics, vol. 10, No. 1, Mar. 2005, pp. 157-166.

Weber et al., "Use of the First Ray Splay Test to Assess Transverse Plane Instability Before First Metatarsocuneiform Fusion," The Journal of Foot and Ankle Surgery, vol. 45, No. 4, Jul./Aug. 2006, pp. 278-282.

Vitek et al., "Die Behandlung des Hallux rigidus mit Cheilektomie und Akin-Moberg-Osteotomie unter Verwendung einer neuen Schnittlehre und eines neuen Schraubensystems," Orthopadische Praxis, vol. 44, Nov. 2008, pp. 563-566, including English Abstract on p. 564.

Vitek, "Neue Techniken in der Fuchirurgie Das V-tek-System," ABW Wissenschaftsverlag GmbH, 2009, 11 pages, including English Abstract.

Yakacki et al. "Compression Forces of Internal and External Ankle Fixation Devices with Simulated Bone Resorption," Foot and Ankle International, vol. 31, No. 1, Jan. 2010, pp. 76-85, (Abstract Only).

Weil et al., "Anatomic Plantar Plate Repair Using the Weil Metatarsal Osteotomy Approach," Foot & Ankle Specialist, vol. 4, No. 3, 2011, pp. 145-150.

Wienke et al., "Bone Stimulation For Nonunions: What the Evidence Reveals," Podiatry Today, vol. 24, No. 9, Sep. 2011, pp. 52-57.

Williams et al., "Metatarsus adductus: Development of a non-surgical treatment pathway," Journal of Paediatrics and Child Health, vol. 49, 2013, pp. E428-433.

Yasuda et al., "Proximal Supination Osteotomy of the First Metatarsal for Hallux Valgus," Foot and Ankle International, vol. 36, No. 6, Jun. 2015, pp. 696-704.

Walker et al., "The Role of First Ray Insufficiency in the Development of Metatarsalgia," Foot and Ankle Clinics, vol. 24, No. 4, Dec. 2019, published online: Sep. 5, 2019, pp. 641-648.

Weigelt et al., "Risk Factors for Nonunion After First Metatarsophalangeal Joint Arthrodesis With a Dorsal Locking Plate and Compression Screw Construct: Correction of Hallux Valgus Is Key," The Journal of Foot & Ankle Surgery, vol. 60, No. 6, Nov./Dec. 2021, pp. 1179-1183.

Wright Medical, "How BLUEPRINT Works—from CT to 3D [CAW -9389]", https://www.wrightmeded.com/videos/how-blueprint-works-from-ct-to-3d-caw-9389, video time mark 32 seconds to 48 seconds, Dated May 26, 2022.

International Searching Authority, "International Search Report and Written Report", From Application No. PCT/US2024/013592, Mailed Jun. 11, 2024, pp. 16.

International Searching Authority, "International Search Report and Written Report", From Application No. PCT/US2024/012970, Mailed Jul. 23, 2024, pp. 12.

Tricot et al., "3D-corrective osteotomy using surgical guides for posttraumatic distal humeral deformity," Acta Orthopaedica Belgica, vol. 78, No. 4, 2012, pp. 538-542.

Vaida et al., "Effect on Foot Width With Triplanar Tarsometatarsal Arthrodesis for Hallux Valgus," Foot & Ankle Orthopaedics, vol. 5, No. 3, 2020, pp. 1-5.

Nyska, Synergy 3D Med, "Anatomical Model: Calcaneus" , 2022, pp. 3.

Okuda et al., "Postoperative Incomplete Reduction of the Sesamoids as a Risk Factor for Recurrence of Hallux Valgus," The Journal of Bone and Joint Surgery, vol. 91-A, No. 1, Jul. 2009, pp. 1637-1645.

Okuda et al., "The Shape of the Lateral Edge of the First Metatarsal Head as a Risk Factor for Recurrence of Hallux Valgus," The Journal of Bone and Joint Surgery, vol. 89, 2007, pp. 2163-2172.

Osher et al., "Accurate Determination of Relative Metatarsal Protrusion with a Small Intermetatarsal Angle: A Novel Simplified Method," The Journal of Foot & Ankle Surgery, vol. 53, No. 5, Sep./Oct. 2014, published online: Jun. 3, 2014, pp. 548-556.

Otsuki et al., "Developing a novel custom cutting guide for curved per-acetabular osteotomy," International Orthopaedics (SICOT), vol. 37, 2013, pp. 1033-1038.

Park et al., "Comparative analysis of clinical outcomes of fixed-angle versus variable-angle locking compression plate for the treatment of Lisfranc injuries," Foot and Ankle Surgery, vol. 26, 2020, pp. 338-342.

Patel et al., "Modified Lapidus Arthrodesis: Rate of Nonunion in 227 Cases," The Journal of Foot & Ankle Surgery, vol. 43, No. 1, Jan./Feb. 2004, pp. 37-42.

Pentikainen et al., "Preoperative Radiological Factors Correlated to Long-Term Recurrence of Hallux Valgus Following Distal Chevron Osteotomy," Foot & Ankle International, vol. 35, No. 12, 2014, pp. 1262-1267.

Perler, " Cuboid Suspension in Charcot Reconstruction. Using 3D Imaging for Planning, Printing and Execution for Complex Deformity Correction" Downloaded Apr. 2021, pp. 4.

Peters et al., "Flexor Hallucis Longus Tendon Laceration as a Complication of Total Ankle Arthroplasty," Foot & Ankle International, vol. 34, No. 1, 2013, pp. 148-149.

Ray et al., "Hallux Valgus," Foot & Ankle Orthopaedics, vol. 4, No. 2, 2019, pp. 1-12.

Ray et al., "Multicenter Early Radiographic Outcomes of Triplanar Tarsometatarsal Arthrodesis With Early Weightbearing," Foot & Ankle International, vol. 40, No. 8, Aug. 1, 2019, published online: May 5, 2019, 7 pages.

Rodriguez et al., "Ilizarov method of fixation for the management of pilon and distal tibial fractures in the compromised diabetic patient: A technique guide," The Foot and Ankle Journal Online, vol. 7, No. 2, 2014, 9 pages.

Rx-Fix Mini Rail External Fixator, Wright Medical Technology, Brochure, Aug. 15, 2014, 2 pages.

Saltzman et al., "Prospective Controlled Trial of STAR Total Ankle Replacement Versus Ankle Fusion: Initial Results," Foot & Ankle International, vol. 30, No. 7, Jul. 2009, pp. 579-596.

Sammarco, "Surgical Strategies: Mau Osteotomy for Correction of Moderate and Severe Hallux Valgus Deformity," Foot & Ankle International, vol. 28, No. 7, Jul. 2007, pp. 857-864.

Sandhu et al., "Digital Arthrodesis With a One-Piece Memory Nitinol Intramedullary Fixation Device: A Retrospective Review," Foot and Ankle Specialist, vol. 6, No. 5, Oct. 2013, pp. 364-366.

Santrock et al., "Hallux Valgus Deformity and Treatment: A Three-Dimensional Approach: Lapiplasty," Foot & Ankle Clinics, vol. 23, No. 2, 2018, pp. 281-295.

Scanlan et al. "Technique Tip: Subtalar Joint Fusion Using a Parallel Guide and Double Screw Fixation," The Journal of Foot and Ankle Surgery, vol. 49, Issue 3, May-Jun. 2010, pp. 305-309, (Abstract Only).

Schon et al., "Cuneiform-Metatarsal Arthrodesis for Hallux Valgus," The Foot and Ankle, Second Edition, Chapter 8, 2002, pp. 99-117.

Scranton Jr. et al., "Anatomic Variations in the First Ray: Part I. Anatomic Aspects Related to Bunion Surgery," Clinical Orthopaedics and Related Research, vol. 151, Sep. 1980, pp. 244-255.

Shima et al., "Operative Treatment for Hallux Valgus With Moderate to Severe Metatarsus Adductus," Foot & Ankle International, vol. 40, No. 6, 2019, pp. 641-647.

Shurnas et al., "Proximal Metatarsal Opening Wedge Osteotomy," Operative Techniques in Foot and Ankle Surgery, Section I, Chapter 13, 2011, pp. 73-78.

Siddiqui et al. "Fixation Of Metatarsal Fracture With Bone Plate In A Dromedary Heifer," Open Veterinary Journal, vol. 3, No. 1, 2013, pp. 17-20.

Sidekick Stealth Rearfoot Fixator, Wright Medical Technology, Surgical Technique, Dec. 2, 2013, 20 pages.

Simons et al., "Short-Term Clinical Outcome of Hemiarthroplasty Versus Arthrodesis for End-Stage Hallux Rigidus," The Journal of Foot & Ankle Surgery, vol. 54, 2015, pp. 848-851.

Simpson et al., "Computer-Assisted Distraction Ostegogenesis by Ilizarov's Method," International Journal of Medical Robots and Computer Assisted Surgery, vol. 4, No. 4, Dec. 2008, pp. 310-320, (Abstract Only).

Small Bone External Fixation System, Acumed, Surgical Technique, Effective date Sep. 2014, 8 pages.

Smith et al., "Intraoperative Multiplanar Alignment System to Guide Triplanar Correction of Hallux Valgus Deformity," Techniques in Foot & Ankle Surgery, 2017, 8 pages.

(56)                     References Cited

OTHER PUBLICATIONS

Smith et al., "Opening Wedge Osteotomies for Correction of Hallux Valgus: A Review of Wedge Plate Fixation," Foot and Ankle Specialist, vol. 2, No. 6, Dec. 2009, pp. 277-282.

Smith et al., "Understanding Frontal Plane Correction in Hallux Valgus Repair," Clinics in Podiatric Medicine and Surgery, vol. 35, 2018, pp. 27-36.

Sokoloff, "Lapidus Procedure," Textbook of Bunion Surgery, Chapter 15, 1981, pp. 277-287.

Stableloc External Fixation System, Acumed, Product Overview, Effective date Sep. 2015, 4 pages.

Stahl et al., "Derotation Of Post-Traumatic Femoral Deformities By Closed Intramedullary Sawing," Injury, vol. 37, No. 2, Feb. 2006, pp. 145-151, (Abstract Only).

Stamatis et al., "Mini Locking Plate as Medial Buttress for Oblique Osteotomy for Hallux Valgus," Foot & Ankle International, vol. 31, No. 10, Oct. 2010, pp. 920-922.

Stryker, "PROstep Minimally Invasive Surgery" https://www.stryker.com/us/en/foot-and-ankle/products/prostep.html, Downloaded Jun. 23, 2023, pp. 10.

Synergy 3D Med, "Anatomical Model: Calcaneus" Downloaded Mar. 2, 2023, pp. 2.

Synopsys, "Medical Image Segmentation with Machine Learning—Simpleware Automated Solution Modules" , https://www.synopsys.com/simpleware/software/auto-segmenter-modules.html#simpleware-as-ortho, 2022, pp. 12.

Talbot et al., " Assessing Sesamoid Subluxation: How Good is the AP Radiograph?," Foot and Ankle International, vol. 19, No. 8, Aug. 1998, pp. 547-554.

TempFix Spanning the Ankle Joint Half Pin and Transfixing Pin Techniques, Biomet Orthopedics, Surgical Technique, 2012, 16 pages.

Tornier Technology, "Tornier Blueprint 3D Planning + PSI" , https://www.wrightemedia.com/ProductFiles/Files/PDFs/CAW-8609_EN_HR_LE.pdf, Feb. 2017, pp. 12.

Total Ankle Institute, "Prophecy: Preoperative Navigation Guides" , https://www.totalankleinstitute.com/infinity-products/prophecy-preoperative-navigation-guides/, 2019, pp. 6.

Toth et al., "The Effect of First Ray Shortening in the Development of Metatarsalgia in the Second Through Fourth Rays After Metatarsal Osteotomy," Foot & Ankle International, vol. 28, No. 1, Jan. 2007, pp. 61-63.

Treace "FastGrafter Autograft Harvesting System" Downloaded from https://www.lapiplasty.com/surgeons/other-products/fastgrafter/, Dec. 4, 2024, pp. 8.

Treace Medical Concepts, "Adductoplasty Midfoot Correction System", https://www.lapiplasty.com/surgeons/other-products/adductoplasty-system/, Downloaded May 2, 2022, pp. 9.

Use for BME Speed Nitinol Staple Fixation for the Lapidus Procedure, "date unknown, 1 page.".

Virzi et al. "Comprehensive Review of 3D Segmentation Software Tools for MRI Usable for Pelvic Surgery Planning", Journal of Digital Imaging (2020) 33, pp. 99-110.

Prior Art Publications, Exhibit A of Defendant Fusion Orthopedics LLC's Invalidity Contentions, No. CV-22-00490-PHX-SRB, US District Court for the District of Arizona, Aug. 27, 2022, 3 pages.

"Foot and Ankle Instrument Set," Smith & Nephew, 2013, 2 pages.

"Lapidus Pearls: Gaining Joint Exposure to Decrease Non-Union," Youtube, Retrieved online from <https://www.youtube.com/watch?v =-jqJyE7pj-Y>, dated Nov. 2, 2009, 3 pages.

"Reconstructive Surgery of the Foot & Ankle," The Podiatry Institute, Update 2015, Conference Program, May 2015, 28 pages.

"Speed Continuous Active Compression Implant," BioMedical Enterprises, Inc., A120-029 Rev. 3, 2013, 4 pages.

"Visionaire: Patient Matched Cutting Blocks Surgical Procedure," Smith & Nephew, Inc., 2009, 2 pages.

ACUMED "Acumed Osteotomy System" with partial English Translation, 2014, pp. 19.

Additive Orthopaedics, "The First and Only FDA Approved Patient Specific Talus Spacer" , https://totaltalusreplacement.com, Downloaded: Mar. 4, 2022, pp. 11.

Aiyer et al. "Prevalence of Metatarsus Adductus in Patients Undergoing Hallux Valgus Surgery" Foot & Ankle International 2014, vol. 35(12), pp. 1292-1297.

Albano et al. "Biomechanical Study of Transcortical or Transtrabecular Bone Fixation of Patellar Tendon Graft With Bioabsorbable Pins in ACL Reconstruction in Sheep" Rev Bras Ortop. 2012, 47(1), pp. 43-49.

Alvine et al. "Peg and Dowel Fusion of the Proximal Interphalangeal Joint" Foot & Ankle vol. 1, No. 2, 1980 American Orthopaedic Foot Society, pp. 5.

ARTHREX "Chevron Osteotomy" https://www.arthrex.com/foot-ankle/chevron-osteotomy, Retrieved Nov. 30, 2022, pp. 7.

ARTHREX "Comprehensive Foot System" https://www.arthrex.com/resources/animation/8U3iaPvY6kO8bwFAwZF50Q/comprehensive-foot-system?referringTeam=foot_and_ankle, Published Aug. 27, 2013, pp. 3.

ARTHREX, "Distal Tibia Allograft Workstation for Glenoid Bone Loss, Surgical Technique" Arthrex.com, 2018, pp. 8.

Baravarian, "Why the Lapidus Procedure is Ideal for Bunions" Podiatry Today, https://www.hmpgloballearningnetwork.com/site/podiatry/article/5542, May 2006 pp. 8.

Bauer et al. "Offset-V Osteotomy of the First Metatarsal Shaft in Hallux Abducto Valgus" Chapter 29, McGlamry's Comprehensive Textbook of Foot and Ankle Surgery, Fourth Edition, 2013, pp. 26.

Bednarz et al. "Modified Lapidus Procedure for the Treatment of Hypermobile Hallux Valgus" Foot & Ankle, American Orthopaedic Foot & Ankle Society, 2000, pp. 6.

Bennett et al. "Intraosseous Sliding Plate Fixation Used in Double Osteotomy Bunionectomy" Foot & Ankle International, 2019, vol. 40(1), pp. 85-88.

BIOPRO "Accu-Cut Osteotomy Guide System Accurate and consistent hallux valgus correction" Document Dates Sep. 16, 2019, pp. 2.

Boffeli et al. "Can We Abandon Saw Wedge Resection in Lapidus Fusion? A Comparative Study of Joint Preparation Techniques Regarding Correction of Deformity, Union Rate, and Preservation of First Ray Length" The Journal of Foot & Ankle Surgery, 58, 2019, pp. 1118-1124.

Bouaicha et al. "Fixation of Maximal Shift Scarf Osteotomy with Inside-Out Plating: Technique Tip" Foot & Ankle International, vol. 32, No. 5, May 2011, pp. 567-569.

Buda et al. "Effect of Fixation Type and Bone Graft on Tarsometatarsal Fusion" Foot & Ankle International 2018, vol. 39(12), pp. 1394-1402.

Carr et al. "Correctional Osteotomy for Metatarsus Primus Varus and Hallux Valgus*" The Journal of Bone and Joint Surgery, vol. 50-A, No. 7, Oct. 1968, pp. 1353-1367.

Catanese et al. "Measuring Sesamoid Position in Hallux Valgus When Is the Sesamoid Axial View Necessary?" Foot & Ankle Specialist, Downloaded Aug. 15, 2016, pp. 1-3.

Chesser et al. "New Advances With the Tarsometatarsal" Podiatry Today, vol. 30, Issue 10, Oct. 2017, pp. 28-36.

Chomej et al. "Lateralising DMMO (MIS) for simultaneous correction of a pes adductus during surgical treatment of a hallux valgus" Journal Pre-proof, The Foot, Accepted Jul. 16, 2020, pp. 33.

Cichero et al. "Different fixation constructs and the risk of nonunion following first metatarsophalangeal joint arthrodesis" Foot and Ankle Surgery, 27, 2021, Accepted Oct. 15, 2020, pp. 789-792.

Coetzee et al., "Revision Hallux Valgus Correction," Operative Techniques in Foot and Ankle Surgery, Section I, Chapter 15, 2011, pp. 84-96.

Collan et al., "The biomechanics of the first metatarsal bone in hallux valgus: A preliminary study utilizing a weight bearing extremity CT," Foot and Ankle Surgery, vol. 19, 2013, pp. 155-161.

"Futura Forefoot Implant Arthroplasty Products," Tornier, Inc., 2008, 14 pages.

"HAT-TRICK Lesser Toe Repair System, Foot and Ankle Technique Guide, Metatarsal Shortening Osteotomy Surgical Technique," Smith & Nephew, 2014, 16 pages.

(56) References Cited

OTHER PUBLICATIONS

"HAT-TRICK Lesser Toe Repair System," Smith & Nephew, Brochure, Aug. 2014, 12 pages.

"Hoffmann II Compact External Fixation System", Stryker, Brochure, Literature No. 5075-1-500, 2006, 12 pages.

"Hoffmann II Micro Lengthener", Stryker, Operative Technique, Literature No. 5075-2-002, 2008, 12 pages.

"Hoffmann Small System External Fixator Orthopedic Instruments," Stryker, retrieved Dec. 19, 2014, from the Internet: <http://www.alibaba.com/product-detail/Stryker-Hoffmann-Small-System-External-Fixator_1438850129.html>, 3 pages.

Patient to Patient Precision, Accu-Cut, Osteotomy Guide System, BioPro, Foot & Ankle International Journal, vol. 23, No. 8, Aug. 2002, 2 pages.

Blomer "Problems and complications of knee endoprostheses from a manufacturer's point of view Orthopade 200, 29, pp. 688-696, English Abstract."

"Prophecy Inbone Preoperative Navigation Guides", Wright Medical Technology, Inc., Nov. 2013, 6 pages.

"RAYHACK Ulnar Shortening Generation II Low-Profile Locking System Surgical Technique," Wright Medical Technology, Inc., Dec. 2013, 20 pages.

Smith & Nephew scores a HAT-TRICK with its entry into the high-growth hammer toe repair market, Smith & Nephew, Jul. 31, 2014, 2 pages.

"Lag Screw Target Bow," Stryker Leibinger GmbH & Co. KG, Germany 2004, 8 pages.

Anderson et al., "Uncemented STAR Total Ankle Protheses" Journal of Bone Joint Surgery America, Sep. 2004, Abstract of Article, pp. 6.

Coetzee et al., "The Lapidus Procedure: A Prospective Cohort Outcome Study," Foot & Ankle International, vol. 25, No. 8, Aug. 2004, pp. 526-531.

Claim Chart for Fishco, "A Straightforward Guide to the Lapidus Bunionectomy," HMP Global (Sep. 6, 2013), Exhibit B2 of Defendant Fusion Orthopedics LLC's Invalidity Contentions, No. CV-22-00490-PHX-SRB, US District Court for the District of Arizona, Aug. 27, 2022, 67 pages.

Claim Chart for Fishco, "Making the Lapidus Easy," The Podiatry Institute (Apr. 2014), Exhibit B1 of Defendant Fusion Orthopedics LLC's Invalidity Contentions, No. CV-22-00490-PHX-SRB, US District Court for the District of Arizona, Aug. 27, 2022, 97 pages.

Claim Chart for Groves Public Use (Mar. 26, 2014), Exhibit B4 of Defendant Fusion Orthopedics LLC's Invalidity Contentions, No. CV-22-00490-PHX-SRB, US District Court for the District of Arizona, Aug. 27, 2022, 161 pages.

Claim Chart for Groves, "Functional Position Joint Sectioning: Pre-Load Method for Lapidus Arthrodesis," Update 2015: Proceedings of the Annual Meeting of the Podiatry Institute, Chpt. 6, pp. 23-29 (Apr. 2015), Exhibit B3 of Defendant Fusion Orthopedics LLC's Invalidity Contentions, No. CV-22-00490-PHX-SRB, US District Court for the District of Arizona, Aug. 27, 2022, 151 pages.

Claim Chart for Mote, "First Metatarsal-Cuneiform Arthrodesis for the Treatment of First Ray Pathology: A Technical Guide," The Journal Foot & Ankle Surgery (Sep. 1, 2009), Exhibit B5 of Defendant Fusion Orthopedics LLC's Invalidity Contentions, No. CV-22-00490-PHX-SRB, US District Court for the District of Arizona, Aug. 27, 2022, 21 pages.

Claim Chart for U.S. Pat. No. 10,376,268 to Fallin et al., entitled "Indexed Tri-Planar Osteotomy Guide and Method," issued Aug. 13, 2019, Exhibit B6 of Defendant Fusion Orthopedics LLC's Invalidity Contentions, No. CV-22-00490-PHX-SRB, US District Court for the District of Arizona, Aug. 27, 2022, 155 pages.

Claim Chart for U.S. Pat. No. 8,282,645 to Lawrence et al., entitled "Metatarsal Bone Implant Cutting Guide," issued Jan. 18, 2010, Exhibit B7 of Defendant Fusion Orthopedics LLC's Invalidity Contentions, No. CV-22-00490-PHX-SRB, US District Court for the District of Arizona, Aug. 27, 2022, 76 pages.

Claim Chart for U.S. Pat. No. 9,452,057 to Dacosta et al., entitled "Bone Implants and Cutting Apparatuses and Methods," issued Apr.

8, 2011, Exhibit B8 of Defendant Fusion Orthopedics LLC's Invalidity Contentions, No. CV-22-00490-PHX-SRB, US District Court for the District of Arizona, Aug. 27, 2022, 110 pages.

Hunt et al., "Locked Versus Nonlocked Plate Fixation For Hallux MTP Arthrodesis," Foot and Ankle International, vol. 32, No. 7, Jul. 2011, pp. 704-709.

Integra, "Integra Large Qwix Positioning and Fixation Screw, Surgical Technique," 2012, 16 pages.

Jackson III et al., "The Surgical Learning Curve for Modified Lapidus Procedure for Hallux Valgus Deformity," Foot & Ankle Specialist, Jul. 2021, 5 pages.

Jeuken et al., "Long-term Follow-up of a Randomized Controlled Trial Comparing Scarf to Chevron Osteotomy in Hallux Valgus Correction," Foot & Ankle International, vol. 37, No. 7, 2016, pp. 687-695.

Kilmartin et al., "Combined rotation scarf and Akin osteotomies for hallux valgus: a patient focused 9 year follow up of 50 patients," Journal of Foot and Ankle Research, vol. 3, No. 2, 2010, 12 pages.

Kim et al., "A Multicenter Retrospective Review of Outcomes for Arthrodesis, Hemi-Metallic Joint Implant, and Resectional Arthroplasty in the Surgical Treatment of End-Stage Hallux Rigidus," The Journal of Foot and Ankle Surgery, vol. 51, 2012, pp. 50-56.

Kim et al., "A New Measure of Tibial Sesamoid Position in Hallux Valgus in Relation to the Coronal Rotation of the First Metatarsal in CT Scans," Foot and Ankle International, vol. 36, No. 8, 2015, pp. 944-952.

Klos et al., "Modified Lapidus arthrodesis with plantar plate and compression screw for treatment of hallux valgus with hypermobility of the first ray: A preliminary report," Foot and Ankle Surgery, vol. 19, 2013, pp. 239-244.

KLS Martin Group, "Individual Patient Solutions IPS Implants" , https://www.klsmartin.com/en-na/products/individual-patient-solutions/ips-implants/, Downloaded: Jun. 1, 2022, pp. 8.

Kurup et al., "Midfoot arthritis- current concepts review," Journal of Clinical Orthopaedics and Trauma, vol. 11, 2020, pp. 399-405.

La Reaux et al., "Metatarsus adductus and hallux abducto valgus: their correlation," The Journal of Foot Surgery, vol. 26, No. 4, Jul. 1987, pp. 304-308, Abstract Only.

Langan et al., "Maintenance of Correction of the Modified Lapidus Procedure With a First Metatarsal to Intermediate Cuneiform Cross-Screw Technique," Foot & Ankle International, vol. 41, No. 4, Apr. 1, 2020, published online: Dec. 26, 2019, pp. 426-436.

Lapidus, "The Author's Bunion Operation From 1931 to 1959," Clinical Orthopaedics, vol. 16, 1960, pp. 119-135.

Latif et al., "First metatarsophalangeal fusion using joint specific dorsal plate with interfragmentary screw augmentation: Clinical and radiological outcomes," Foot and Ankle Surgery, vol. 25, 2019, pp. 132-136.

Le et al., "Tarsometatarsal Arthrodesis," Operative Techniques in Foot and Ankle Surgery, Section II, Chapter 40, 2011, pp. 281-285.

Lee et al., "Technique Tip: Lateral Soft-Tissue Release for Correction of Hallux Valgus Through a Medial Incision Using a Dorsal Flap Over the First Metatarsal," Foot & Ankle International, vol. 28, No. 8, Aug. 2007, pp. 949-951.

Li et al., "Evolution of Thinking of the Lapidus Procedure and Fixation," Foot and Ankle Clinics, vol. 25, No. 1, Mar. 2020, published online: Dec. 16, 2019, pp. 18 pages.

Lieske et al., "Implantation einer Sprunggelenktotalendo-prothese vom Typ Salto 2," Operative Orthopdie und Traumatologie, vol. 26, No. 4, 2014, pp. 401-413, including English Abstract on p. 403.

Little, "Joint Arthrodesis for Hallux Valgus," Clinics in Podiatric Medicine and Surgery, Hallux Abducto Valgus Surgery, updated Apr. 19, 2014, retrieved online from < https://www.footankleinstitute.com/first-metatarsophalangeal-joint-arthrodesis-in-the-treatment-of-hallux-valgus>, 7 pages.

Lopez et al., "Metatarsalgia: Assessment Algorithm and Decision Making," Foot and Ankle Clinics, vol. 24, No. 4, Dec. 2019, published online: Sep. 25, 2019, pp. 561-569.

MAC (Multi Axial Correction) Fixation System, Biomet Trauma, retrieved Dec. 19, 2014, from the Internet: <http://footandanklefixation.com/product/biomet-trauma-mac-multi-axial-correction-fixation-system>, 7 pages.

(56)        References Cited

OTHER PUBLICATIONS

Machacek Jr. et al., "Salvage of a Failed Keller Resection Arthroplasty," The Journal of Bone and Joint Surgery, vol. 86A, No. 6, Jun. 2004, pp. 1131-1138.

Magin, "Computernavigierter Gelenkersatz am Knie mit dem Orthopilot," Operative Orthopdie und Traumatologie, vol. 22, No. 1, 2010, pp. 63-80, including English Abstract on p. 64.

Magin, "Die belastungsstabile Lapidus-Arthrodese bei Hallux-valgus-Deformitt mittels IVP-Plattenfixateur (V-TEK- System)," Operative Orthopdie und Traumatologie, vol. 26, No. 2, 2014, pp. 184-195, including English Abstract on p. 186.

Marshall et al., "The identification and appraisal of assessment tools used to evaluate metatarsus adductus: a systematic review of their measurement properties," Journal of Foot and Ankle Research, vol. 11, No. 25, 2018, 10 pages.

McAleer et al., "A systematic approach to the surgical correction of combined hallux valgus and metatarsus adductus deformities," The Journal of Foot & Ankle Surgery, May 21, 2021, 6 pages.

McAleer et al., "Radiographic Outcomes Following Triplanar Correction of Combined Hallux Valgus and Metatarsus Adductus Deformities," ACFAS Scientific Conference, Poster, Feb. 2022, 1 page.

McCabe et al., "Anatomical reconstruction of first ray instability hallux valgus with a medial anatomical TMTJ1 plate," Foot and Ankle Surgery, vol. 27, No. 8, Dec. 2021, pp. 869-873.

Mehtar et al., "Outcomes of bilateral simultaneous hallux MTPJ fusion," Foot and Ankle Surgery, vol. 27, 2021, pp. 213-216.

Michelangelo Bunion System, Surgical Technique ", Instratek Incorporated, publication date unknown, 4 pages."

Miller et al., "Variable Angle Locking Compression Plate as Alternative Fixation for Jones Fractures: A Case Series," Kansas Journal of Medicine, vol. 12, No. 2, May 2019, pp. 28-32.

Mini Joint Distractor, Arthrex, retrieved Dec. 19, 2014, from the Internet: < http://www.arthrex.com/foot-ankle/mini-joint-distractor/products>, 2 pages.

MiniRail System, Small Bone Innovations, Surgical Technique, 2010, 24 pages.

Miyake et al., "Three-Dimensional Corrective Osteotomy for Malunited Diaphyseal Forearm Fractures Using Custom-Made Surgical Guides Based on Computer Simulation," JBJS Essential Surgical Techniques, vol. 2, No. 4, 2012, 11 pages.

Mizuno et al., "Detorsion Osteotomy of the First Metatarsal Bone in Hallux Valgus," Japanese Orthopaedic Association, Tokyo, 1956; 30:813-819.

Modular Rail System: External Fixator, Smith & Nephew, Surgical Technique, 2013, 44 pages.

Monnich et al., "A Hand Guided Robotic Planning System for Laser Osteotomy in Surgery," World Congress on Medical Physics and Biomedical Engineering vol. 25/6: Surgery, Nimimal Invasive Interventions, Endoscopy and Image Guided Therapy, Sep. 7-12, 2009, pp. 59-62, (Abstract Only).

Moore et al., "Effect of Ankle Flexion Angle on Axial Alignment of Total Ankle Replacement," Foot and Ankle International, vol. 31, No. 12, Dec. 2010, pp. 1093-1098, (Abstract Only).

Mortier et al., "Axial Rotation of the First Metatarsal Head in a Normal Population and Hallux Valgus Patients," Orthopaedics and Traumatology: Surgery and Research, vol. 98, 2012, pp. 677-683.

Mote et al., "First Metatarsal-Cuneiform Arthrodesis for the Treatment of First Ray Pathology: A Technical Guide," JFAS Techniques Guide, vol. 48, No. 5, Sep./Oct. 2009, pp. 593-601.

Musculoskeletal Key "Arthrodesis of the Tarsmetatarsal Joint" https://musculoskeletalkey.com/arthrodesis-of-the-tarsometatarsal-joint/, Retrieved May 8, 2020, pp. 11.

Myerson, "Cuneiform-Metatarsal Arthrodesis," The Foot and Ankle, Chapter 9, 1997, pp. 107-117.

Nagy et al., "The AO Ulnar Shortening Osteotomy System Indications and Surgical Technique," Journal of Wrist Surgery, vol. 3, No. 2, 2014, pp. 91-97.

NexFix from Nexa Orthopedics, MetaFix I from Merete Medical, Inc. and The BioPro Lower Extremities from BioPro, found in Foot & Ankle International Journal, vol. 28, No. 1, Jan. 2007, 4 pages.

Nix et al., "Prevalence of hallux valgus in the general population: a systematic review and meta-analysis," Journal of Foot and Ankle Research, vol. 3, No. 21, 2010, 9 pages.

Novastep, "Pecaplasty Percutaneous Bunion Correction" Downloaded Jun. 29, 2022, pp. 24.

Novastep, "Pecaplasty Percutaneous Bunion Correction- Brochure Pecaplasty Targeting Guide" Downloaded Dec. 15, 2021, pp. 4.

Odenbring et al., "A guide instrument for high tibial osteotomy," Acta Orthopaedica Scandinavica, vol. 60, No. 4, 1989, pp. 449-451.

Okuda et al., "Proximal Metatarsal Osteotomy for Hallux Valgus: Comparison of Outcome for Moderate and Severe Deformities, Foot and Ankle International," vol. 29, No. 7, Jul. 2008, pp. 664-670.

Instratek, "Michelangelo Bunion System, Surgical Technique", Instratek Incorporated, publication date unknown, 4 pages.

* cited by examiner

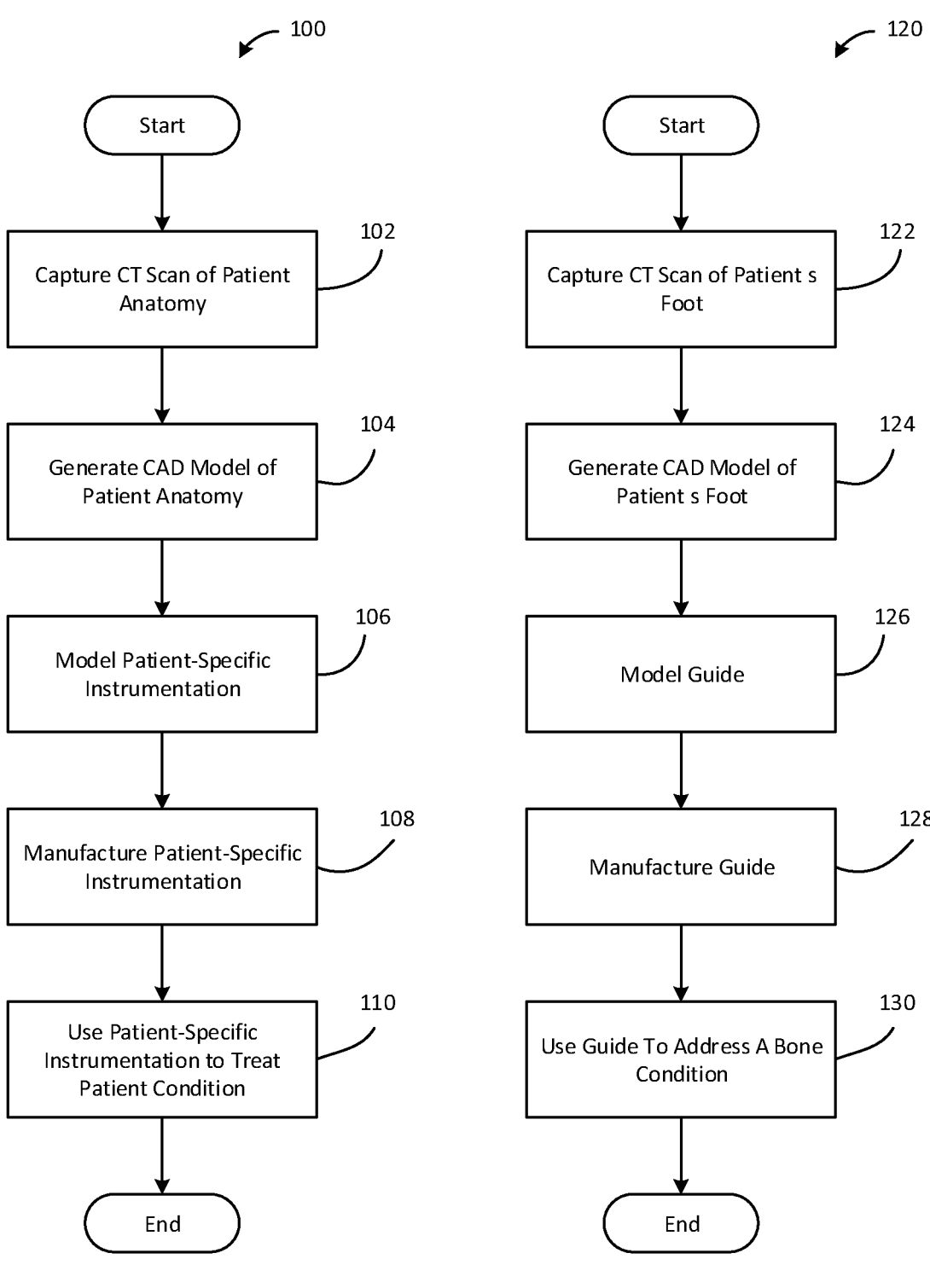
FIG. 1A                    FIG. 1B

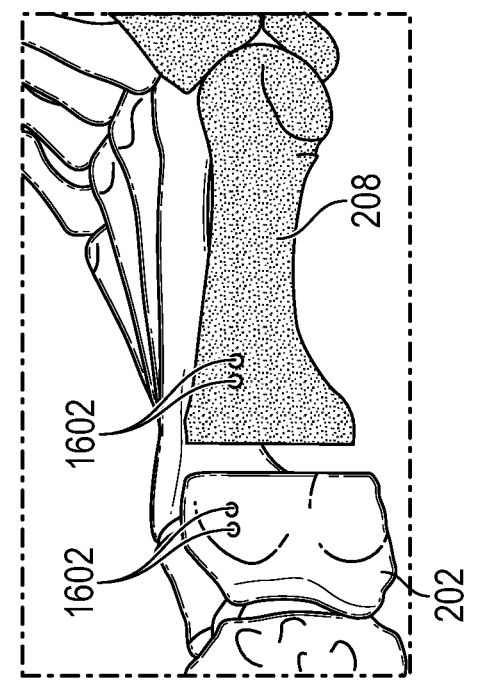
FIG. 16F
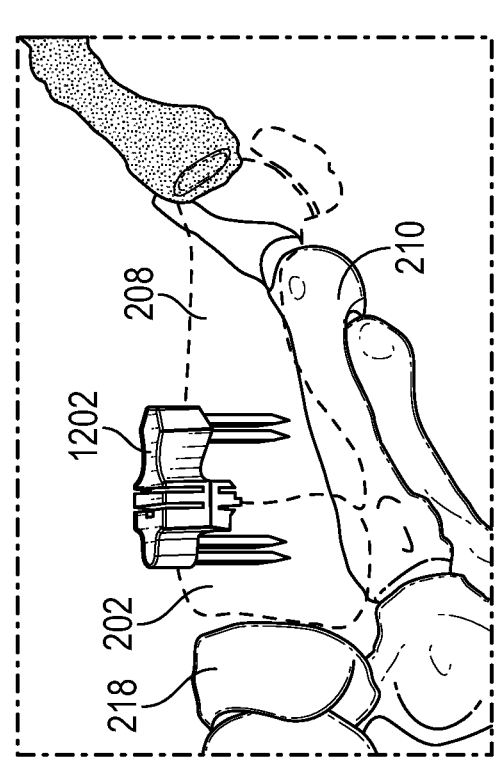
FIG. 16E
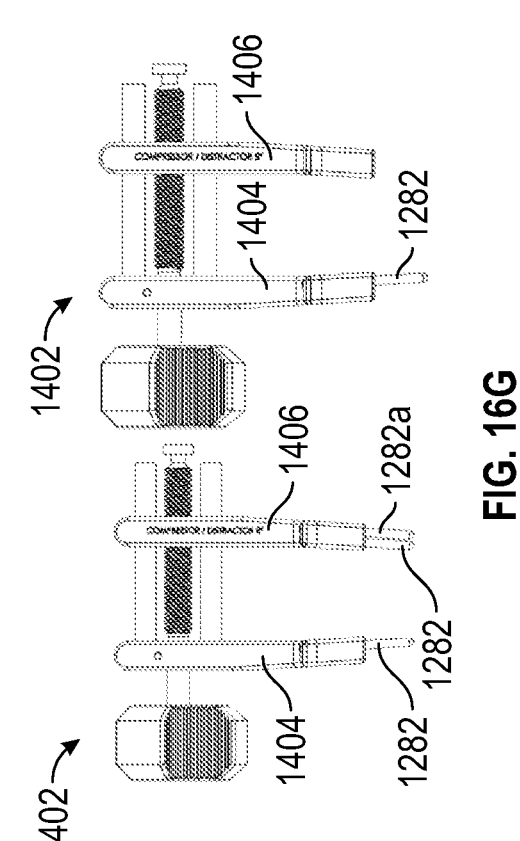
FIG. 16H
FIG. 16G

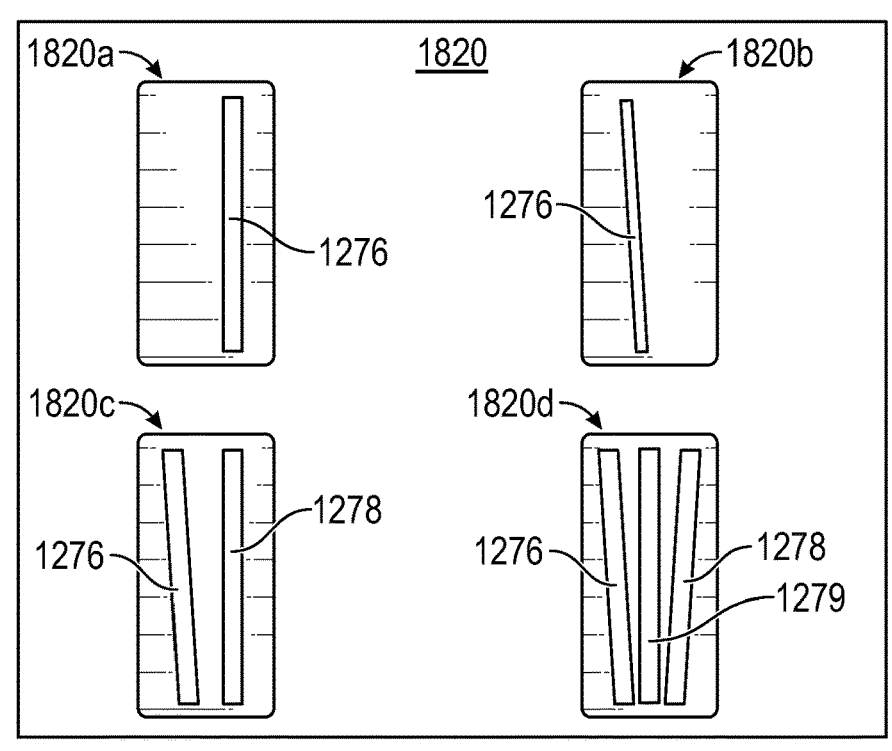
FIG. 19A
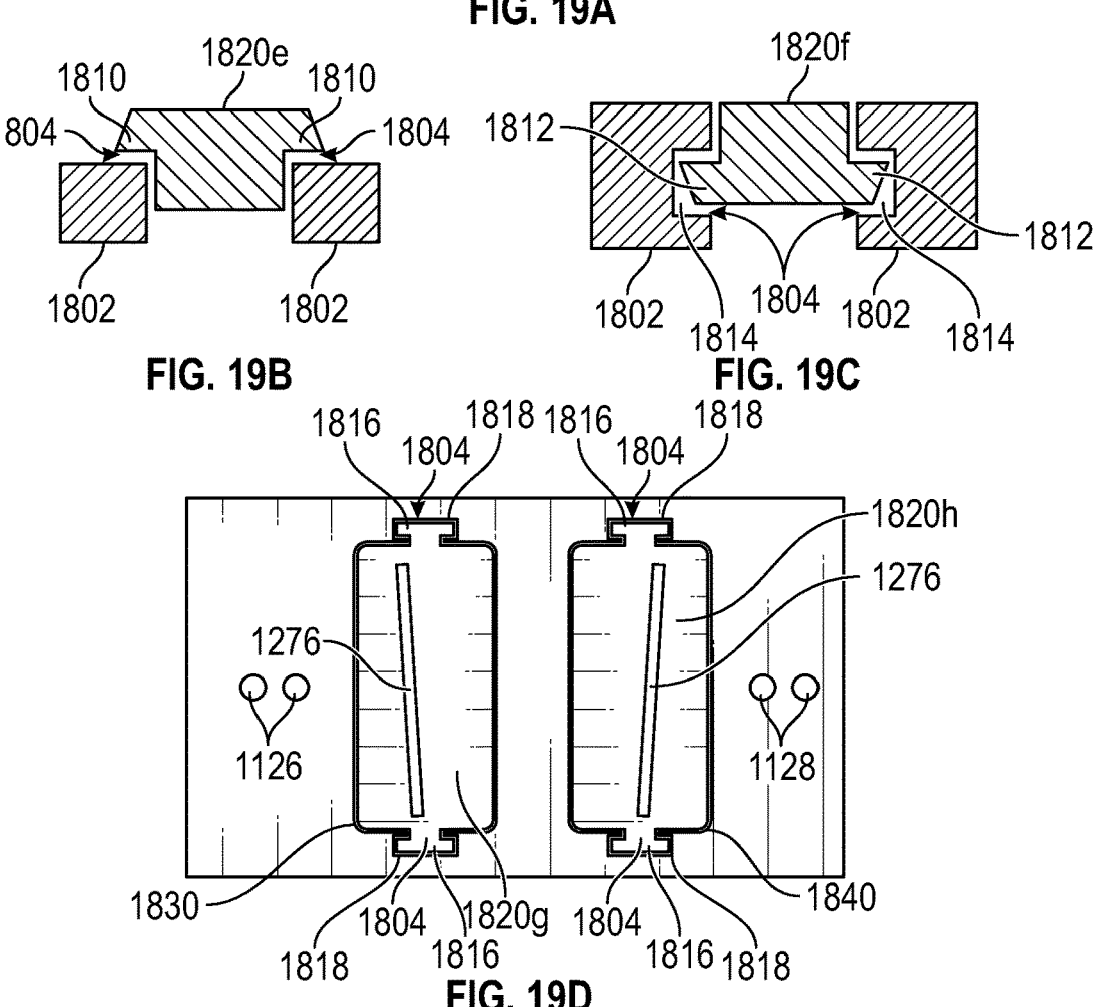
FIG. 19B
FIG. 19C
FIG. 19D

APPARATUS, SYSTEM, AND METHOD FOR OSTEOTOMIES

CROSS-REFERENCE TO RELATED APPLICATIONS

This application claims the benefit of and priority to U.S. Provisional Application No. 63/482,038, filed Jan. 28, 2023, which is hereby incorporated by reference in its entirety. This application also claims the benefit of and priority to U.S. Provisional Application No. 63/482,197, filed Jan. 30, 2023, which is hereby incorporated by reference in its entirety.

TECHNICAL FIELD

The present disclosure relates to surgical devices, systems, instruments, and methods. More specifically, the present disclosure relates to patient-specific guides, implants, instruments, and/or methods of designing and using the same.

BACKGROUND

Various bone conditions may be corrected using surgical procedures, in which one or more tendons, ligaments, joints, and/or bones may be cut, replaced, repositioned, reoriented, reattached, fixated and/or fused. These surgical procedures require the surgeon to properly locate, position, and/or orient one or more osteotomy cuts, fixation guides, fixators, bone tunnels, points of attachment for ends of grafts or soft tissue and the like. Conventional tools enable a surgeon to preplan the osteotomies using models of patient tissue, models of instruments and the like. However, determining and locating an optimal location, position, orientation, and/or trajectory for one or more steps, instruments, and/or anatomical structures for the surgical procedure can be challenging, given conventional techniques and instruments. What is needed is one or more guides to facilitate locating, aligning, orienting, planning, preparing for, initiating, and/or complete one or more osteotomies. Existing solutions for guiding orthopedic surgical procedures are inadequate and error prone.

SUMMARY

The various apparatuses, devices, systems and methods of the present disclosure have been developed in response to the present state of the art, and in particular, in response to the problems and needs in the art that have not yet been fully solved by currently available apparatuses, devices, systems, and/or methods.

In one general aspect, the apparatus may include a body having an inferior side and a superior side. The apparatus may also include a window that extends from the inferior side of the body to the superior side of the body, the window configured to enable a user to view an anatomical reference when the apparatus is in use. The apparatus may furthermore include where the window is configured to accept a resection guide insert configured to guide a cutting tool to form one or more osteotomies in at least one bone.

In one general aspect, the apparatus may include a body having a proximal side, a distal side, a medial side, a lateral side, an inferior side, and a superior side. The apparatus may also include a window that extends from one side of the body to an opposite side of the body, the window configured to enable a user to view an anatomical reference when the apparatus is in use. The apparatus may furthermore include a reference feature guide coupled to the body, the reference feature guide configured to guide a user in providing one or more reference features.

Implementations may include one or more of the following features. An apparatus where the body may include a plurality of position indicator holes each configured to accept one or more position indicators. An apparatus where the plurality of position indicator holes are configured such that a first position indicator deployed through a first set of position indicator holes and a second position indicator deployed through a second set of position indicator holes form a third position indicator within the window. An apparatus where the third position indicator may include a crosshair. An apparatus where at least one of the plurality of position indicator holes is a blind hole. An apparatus where the body is made of a radiolucent material. An apparatus where the reference feature guide may include at least one hole in the body that extends from a bone-facing side of the body to an opposite side of the body when the apparatus is used.

An apparatus may include a bone engagement surface on the inferior side of the body, the bone engagement surface configured to engage with a bone of the patient when the body is in a desired position. An apparatus where the desired position is a position for the body defined based at least in part on a bone model of a bone of the patient, the bone model defined based at least in part on medical imaging of a patient. An apparatus where the window is configured to accept a resection guide insert configured to guide a cutting tool to form one or more osteotomies in at least one bone. An apparatus may include an engagement interface configured to engage the resection guide insert and retain the resection guide insert as the one or more osteotomies are formed.

In one general aspect, the system may include a navigation guide having a body having: a proximal side, a distal side, a medial side, a lateral side, an inferior side, and a superior side; an opening that extends from one side of the body to an opposite side of the body, the opening configured to provide a view of an anatomical reference. The system may also include at least one position indicator that indicates a position of the navigation guide in relation to the anatomical reference. The system may furthermore include an instrument configured to participate in addressing a bone condition present in the patient. The system may in addition include at least one reference feature configured to interface between the instrument and a bone or a bone fragment.

Implementations may include one or more of the following features. A system where the navigation guide is configured to accept the at least one position indicator. A system where the navigation guide may include one or more holes configured to accept the at least one position indicator. A system where the at least one position indicator extends across the opening from a first side of the opening to a second side of the opening, the at least one position indicator configured to align with the anatomical reference, the system may include: a second position indicator configured to indicate a trajectory of a first bone or bone fragment in relation to a second bone or bone fragment after one or more steps for addressing a bone condition present in a patient. A system where the at least one position indicator and the second position indicator traverse each other within the opening.

A system may include at least one resection guide; an alignment guide; and a compression guide.

In one general aspect, the method may include positioning a navigation guide adjacent to an anatomical reference of the patient, the navigation guide having: a body having a proximal end that includes a proximal side and a distal end that includes a distal side, a medial side, a lateral side, a superior side, and an inferior side; a window that extends from the superior side to the inferior side, the window having a proximal edge, a distal edge, a medial edge, and a lateral edge; a first position indicator that extends across the window between the proximal edge and the distal edge; a second position indicator that extends across the window between the medial edge and the lateral edge.

The method may also include providing one or more reference features in one or more bones of the patient.

The method may furthermore include deploying a resection guide to a predetermined position defined based on the one or more reference features, the resection guide having: a proximal end that includes a proximal side; a distal end that includes a distal side; a medial side, a lateral side, a superior side, and an inferior side; one or more resection guide features configured to guide a cutting tool in resecting tissue of the patient.

The method may in addition include resecting one or more bones of the patient by activating a cutting tool within at least one of the resection guide features of the resection guide to form a proximal bone fragment and a distal bone fragment.

The method may moreover include coupling an alignment guide to the one or more reference features of at least one of the proximal bone fragment and the distal bone fragment. The method may also include providing an alignment feature using the alignment guide, the alignment feature configured to engage one or more of the proximal bone fragment and the distal bone fragment.

The method may furthermore include deploying a compressor/distractor that engages at least one reference feature and at least one alignment feature. The method may in addition include compressing the proximal bone fragment and the distal bone fragment together to remediate the bone condition.

Implementations may include one or more of the following features. A method where the resection guide may include a bone attachment feature configured to engage one or more bones and secure the resection guide to the one or more bones. A method where the resection guide may include a resection guide insert and where deploying the resection guide to the predetermined position may include coupling the resection guide insert to the navigation guide, the navigation guide coupled to the reference features.

BRIEF DESCRIPTION OF THE DRAWINGS

The advantages, nature, and additional features of exemplary embodiments of the disclosure will become more fully apparent from the following description and appended claims, taken in conjunction with the accompanying drawings. Understanding that these drawings depict only exemplary embodiments and are, therefore, not to be considered limiting of the disclosure's scope, the exemplary embodiments of the disclosure will be described with additional specificity and detail through use of the accompanying drawings.

FIG. 1A is a flowchart diagram depicting a method for remediating a condition, according to one embodiment.

FIG. 1B is a flowchart diagram depicting a method for remediating a condition, according to one embodiment.

FIGS. 16A-16H illustrate different views of stages of a surgical procedure.

FIGS. 19A-19D illustrates examples of a few, of a variety of different types and configurations of resection guides that can be used with the navigation guide and/or engagement interfaces, according to one embodiment.

DETAILED DESCRIPTION

Figures 2A, 2B:
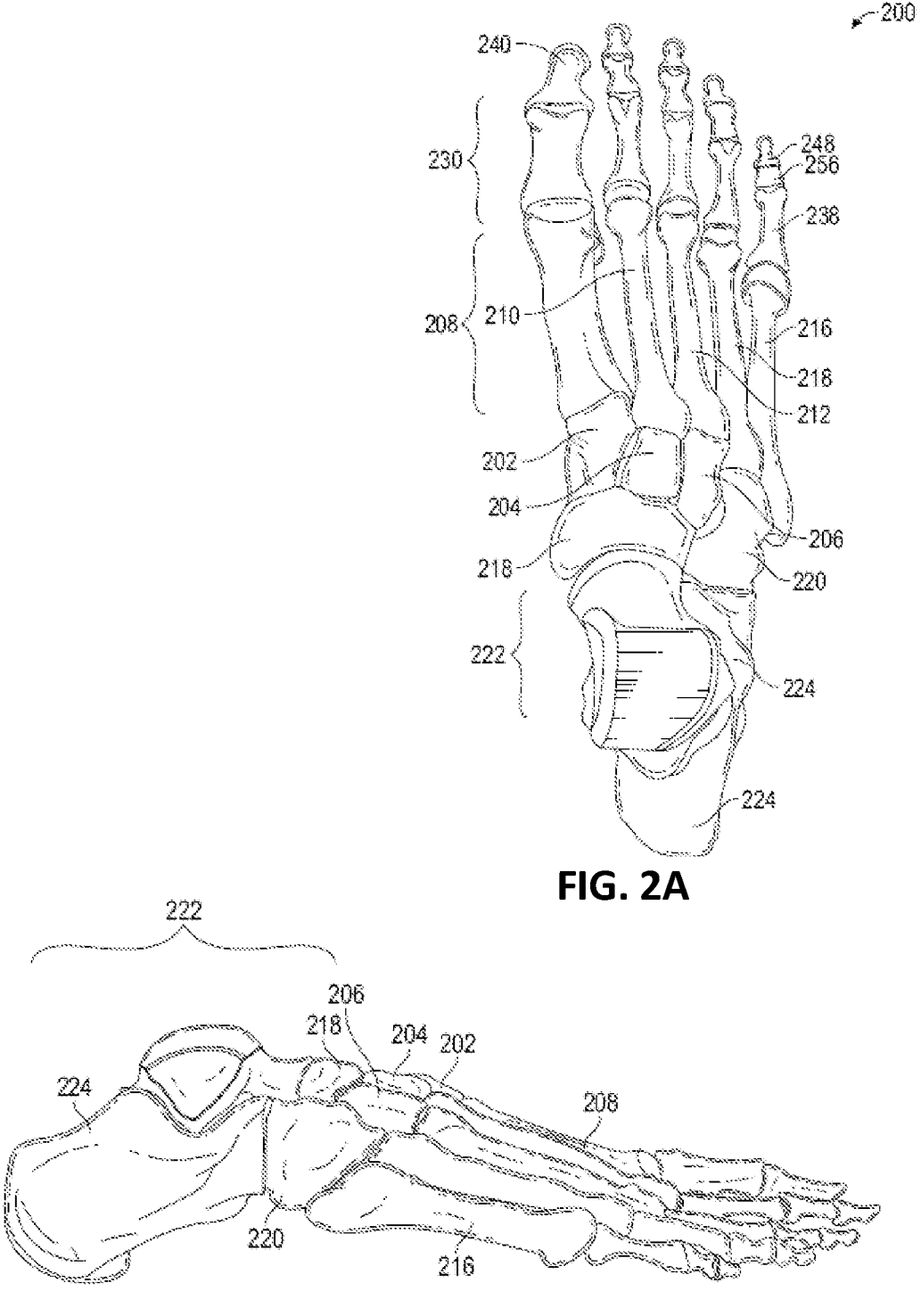
FIG. 2A is a dorsal perspective view of bones of a foot.
FIG. 2B is a lateral perspective view of bones of a foot.

Exemplary embodiments of the disclosure will be best understood by reference to the drawings, wherein like parts are designated by like numerals throughout. It will be readily understood that the components, as generally described and illustrated in the Figures herein, could be arranged and designed in a wide variety of different configurations. Thus, the following more detailed description of the embodiments of the apparatus, system, and method is not intended to limit the scope of the disclosure but is merely representative of exemplary embodiments.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The phrase "fluid communication" refers to two features that are connected such that a fluid within one feature can pass into the other feature.

As used herein, "coupling", "coupling member", or "coupler" refers to a mechanical device, apparatus, member, component, system, assembly, or structure, that is organized, configured, designed, arranged, or engineered to connect, or facilitate the connection of, two or more parts, objects, or structures. In certain embodiments, a coupling can connect adjacent parts or objects at their ends. In certain embodiments, a coupling can be used to connect two shafts together at their ends for the purpose of transmitting power. In other embodiments, a coupling can be used to join two pieces of rotating equipment while permitting some degree of misalignment or end movement or both. In certain embodiments, couplings may not allow disconnection of the two parts, such as shafts during operation. (Search "coupling" on Wikipedia.com Jul. 26, 2021. CC-BY-SA 3.0 Modified. Accessed Jul. 27, 2021.) A coupler may be flexible, semi-flexible, pliable, elastic, or rigid. A coupler may join two structures either directly by connecting directly to one structure and/or directly to the other or indirectly by connecting indirectly (by way of one or more intermediary structures) to one structure, to the other structure, or to both structures.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

Standard medical planes of reference and descriptive terminology are employed in this disclosure. While these terms are commonly used to refer to the human body, certain terms are applicable to physical objects in general. A standard system of three mutually perpendicular reference planes is employed. A sagittal plane divides a body into right and left portions. A coronal plane divides a body into anterior and posterior portions. A transverse plane divides a body into superior and inferior portions. A mid-sagittal, mid-coronal, or mid-transverse plane divides a body into equal portions, which may be bilaterally symmetric. The intersection of the sagittal and coronal planes defines a superior-inferior or cephalad-caudal axis. The intersection of the sagittal and transverse planes defines an anterior-posterior axis. The intersection of the coronal and transverse planes defines a medial-lateral axis. The superior-inferior or cephalad-caudal axis, the anterior-posterior axis, and the medial-lateral axis are mutually perpendicular.

Anterior means toward the front of a body. Posterior means toward the back of a body. Superior or cephalad means toward the head. Inferior or caudal means toward the feet or tail. Medial means toward the midline of a body, particularly toward a plane of bilateral symmetry of the body. Lateral means away from the midline of a body or away from a plane of bilateral symmetry of the body. Axial means toward a central axis of a body. Abaxial means away from a central axis of a body. Ipsilateral means on the same side of the body. Contralateral means on the opposite side of the body from the side which has a particular condition or structure. Proximal means toward the trunk of the body. Proximal may also mean toward a user, viewer, or operator. Distal means away from the trunk. Distal may also mean away from a user, viewer, or operator. Dorsal means toward the top of the foot or other body structure. Plantar means toward the sole of the foot or toward the bottom of the body structure.

Antegrade means forward moving from a proximal location/position to a distal location/position or moving in a forward direction. Retrograde means backward moving from a distal location/position to a proximal location/position or moving in a backwards direction. Sagittal refers to a midline of a patient's anatomy, which divides the body into left or right halves. The sagittal plane may be in the center of the body, splitting it into two halves. Prone means a body of a person lying face down. Supine means a body of a person lying face up.

"Patient-specific guide" refers to a guide designed, engineered, and/or fabricated for use with a specific patient. In one aspect, a patient-specific guide is unique to a patient and may include features unique to the patient such as a surface contour or other features.

"Patient-specific cutting guide" refers to a cutting guide designed, engineered, and/or fabricated for use with a specific patient. In one aspect, a patient-specific cutting guide is unique to a patient and may include features unique to the patient such as a surface contour or other features.

"Patient-specific resection guide" refers to a guide designed, engineered, and/or fabricated for use in resection for a specific patient. In one aspect, a patient-specific resection guide is unique to a patient and may include features unique to the patient such as a surface contour or other features.

"Patient-specific tendon trajectory guide" refers to a tendon trajectory guide designed, engineered, and/or fabricated for use with a specific patient. In one aspect, a patient-specific tendon trajectory guide is unique to a single patient and may include features unique to the patient such as a surface contour or other features.

"Patient-matched" refers to a feature, aspect, attribute, characteristic, instrument, and/or device that is selected from a set of predetermined, predefined, precalculated, preconfigured, prearranged, and/or pre-fabricated structures, apparatuses, devices, instruments or devices to satisfactorily service a user based on a set of characteristics, such as size of an anatomical structure, deformity, fracture, laceration, opening, angles for certain landmarks, angles for a deformity, type of deformity, size of the bone, and the like. In certain embodiments, patient-matched is different from patient-specific.

As used herein, "implant" refers to a medical device manufactured to replace a missing biological structure, support a damaged biological structure, or enhance an existing biological structure. Often medical implants are man-made devices, but implants can also be natural occurring structures. The surface of implants that contact the body may be made of, or include a biomedical material such as titanium, cobalt chrome, stainless steel, carbon fiber, another metallic alloy, silicone, polymer, Synthetic polyvinyl alcohol (PVA) hydrogels, biomaterials, biocompatible polymers such as PolyEther Ether Ketone (PEEK) or a polylactide polymer (e.g. PLLA) and/or others, or apatite, or any combination of these depending on what is functional and/or economical. Implants can have a variety of configurations and can be wholly, partially, and/or include a number of components that are flexible, semiflexible, pliable, elastic, supple, semi-rigid, or rigid. In some cases, implants contain electronics, e.g. artificial pacemaker and cochlear implants. Some implants are bioactive, such as subcutaneous drug delivery devices in the form of implantable pills or drug-eluting stents. Orthopedic implants may be used to alleviate issues with bones and/or joints of a patient's body. Orthopedic implants can be used to treat bone fractures, osteoarthritis, scoliosis, spinal stenosis, discomfort, and pain. Examples of orthopedic implants include, but are not limited to, a wide variety of pins, rods, screws, anchors, spacers, sutures, all-suture implants, ball all-suture implants, self-locking suture implants, cross-threaded suture implants, plates used to anchor fractured bones while the bones heal or fuse together, and the like. (Search "implant (medicine)" on Wikipedia.com May 26, 2021. CC-BY-SA 3.0 Modified. Accessed Jun. 30, 2021.)

As used herein, a "body" refers to a main or central part of a structure. The body may serve as a structural component to connect, interconnect, surround, enclose, and/or protect one or more other structural components. A body may be made from a variety of materials including, but not limited to, metal, plastic, nylon, nylon 12, ceramic, wood, fiberglass, acrylic, carbon, biocompatible materials, biodegradable materials or the like. A body may be formed of any biocompatible materials, including but not limited to biocompatible metals such as Titanium, Titanium alloys, stainless steel alloys, cobalt-chromium steel alloys, nickel-titanium alloys, shape memory alloys such as Nitinol, biocompatible ceramics, and biocompatible polymers such as Polyether ether ketone (PEEK) or a polylactide polymer (e.g. PLLA) and/or others.

A body can be two-dimensional or three-dimensional and can have a variety of geometric shapes and/or cross-sectional shapes, including, but not limited to a rectangle, a square, or other polygon, as well as a circle, an ellipse, an ovoid, or other circular or semi-circular shape.

In one embodiment, a body may include a housing or frame, or framework for a larger system, component, structure, or device. A body may include a modifier that identifies a particular function, location, orientation, operation, and/or a particular structure relating to the body. Examples of such modifiers applied to a body, include, but are not limited to, "inferior body," "superior body," "lateral body," "medial body," and the like.

As used herein, "bone engagement surface" refers to a surface of an object, instrument, or apparatus, such as an implant that is oriented toward or faces one or more bones of a patient. In one aspect, the bone engagement surface may abut, touch, or contact a surface of a bone. In another aspect, the bone engagement surface or parts of the bone engagement surface may be close to, but not abut, touch, or contact a surface of the bone. In certain aspects, the bone engagement surface can be configured to engage with a surface of one or more bones. Such a bone engagement surface may include projections and recesses that correspond to and match projections and recesses of the one or more bone surfaces.

As used herein, "bone-facing side" refers to a side of an object, structure, instrument, or apparatus, such as an implant or instrument that is oriented toward or faces one or more bones of a patient. In one aspect, the bone-facing side may abut, touch, or contact a surface of a bone. In another aspect, the bone-facing side or parts of the bone-facing side may be close to, but not abut, touch, or contact a surface of the bone.

As used herein, a "deploy" or "deployment" refers to an act, action, process, system, method, means, or apparatus for inserting an implant or prosthesis into a part, body part, and/or patient. "Deploy" or "deployment" can also refer to an act, action, process, system, method, means, or apparatus for placing something into therapeutic use. A device, system, component, medication, drug, compound, or nutrient may be deployed by a human operator, a mechanical device, an automated system, a computer system or program, a robotic system, or the like.

"Joint" or "Articulation" refers to the connection made between bones in a human or animal body which link the skeletal system to form a functional whole. Joints may be biomechanically classified as a simple joint, a compound joint, or a complex joint. Joints may be classified anatomically into groups such as joints of hand, elbow joints, wrist joints, axillary joints, sternoclavicular joints, vertebral articulations, temporomandibular joints, sacroiliac joints, hip joints, knee joints, articulations of foot, and the like. (Search "joint" on Wikipedia.com Dec. 19, 2021. CC-BY-SA 3.0 Modified. Accessed Jan. 20, 2022.)

"Topographical" refers to the physical distribution of parts, structures, or features on the surface of, or within, an organ or other anatomical structure, or organism. (Search "define topographical" on google.com. Oxford Languages, Copyright 2022. Oxford University Press. Web., Modified. Accessed 15 Feb. 2022.)

"Window" refers to an opening and/or a plurality of openings in a body, side, wall, side door, roof, vehicle, system, component, or other structure that allows the passage of electromagnetic radiation including radio ways, x-rays, visible light, light, and the like. A window may also permit passage of sound, gases, fluids, liquids, or other elements. (Search "window" on Wikipedia.com Aug. 31, 2022. Modified. Accessed Sep. 21, 2022.). A window can be opaque, semi-opaque, translucent, radiolucent, or transparent. A window can include a single opening having a single geometric shape or a plurality of openings each of a single geometric shape or combination of a variety of geometric shapes. In certain embodiments, a window may be referred to as a radiolucent window. A radiolucent window may permit passage of some or all radio ways through the window and may include an opening or may be a solid structure.

"Radiolucent" refers to any structure, apparatus, surface, device, system, feature, or aspect that permits radio waves to pass from one side of the radiolucent structure to the opposite side. The radio waves can be any radio wave including light, x-rays, and the like. A radiolucent structure, apparatus, surface, device includes structures that define an opening or hole (e.g., a structural opening) in the structure, apparatus, surface, device such that radio waves from one side of the structure, apparatus, surface, device pass through one or more openings or holes to an opposite side of the structure, apparatus, surface, device. A radiolucent structure, apparatus, surface, device also includes structures that comprise a solid material (e.g., no holes or openings, not a structural opening) that is configured to permit passage of one type of radio wave but not another type of radio wave. For example, a radiolucent structure, apparatus, surface, device may be made of a material such as a plastic or polymer which may prevent passage of one radio wave, such as light, from one side of the structure, apparatus, surface, device to the other, but may permit passage of another radio wave, such as X-rays from one side of the structure, apparatus, surface, device to the other.

"Landmark registration features" or "Landmark" refers to a structure configured to engage with a feature, aspect, attribute, or characteristic of a first object to orient and/or position a second object that includes the landmark registration feature with respect to the first object. A variety of structures can serve as a landmark registration feature. For example, a landmark registration feature may include a protrusion, a projection, a tuberosity, a cavity, a void, a divot, a tab, an extension, a hook, a curve, or the like. In the context of bones of a patient a landmark registration feature can include any protuberance, void, divot, concave section, sesamoid, bone spur or other feature on, or extending from, a bone of a patient.

"Bone attachment feature" refers to a structure, feature, component, aspect configured to securely connect, couple, attach, and/or engage a structure, component, object, or body with a bone and/or a bone fragment. A bone attachment feature may enable temporary engagement with a bone or bone fragment or permanent engagement with a bone or bone fragment. Examples of a bone attachment feature, include, but are not limited to, a pin, K-wire, screw, or other fastener alone, or a fastener in combination with, a hole, passage, and/or opening, an adhesive, a cement, a barb, a prong, or the like.

As used herein, "patient specific osteotomy procedure" refers to an osteotomy procedure that has been adjusted, tailored, modified, or configured to specifically address the anatomy, physiology, condition, abnormalities, needs, or desires of a particular patient. In certain aspects, one patient specific osteotomy procedure may be useable in connection with only one patient. In other aspects, one patient specific osteotomy procedure may be useable with a number of patients having a particular class of characteristics. In certain aspects, a patient specific osteotomy procedure may refer to a non-patient specific osteotomy procedure that includes one or more patient specific implants and/or instrumentation. In another aspects, a patient specific osteotomy procedure may refer to a patient specific osteotomy procedure that includes one or more patient specific implants, patient specific surgical steps, and/or patient specific instrumentation.

As used herein, a "stop" refers to an apparatus, instrument, structure, member, device, component, system, or assembly structured, organized, configured, designed, arranged, or engineered to prevent, limit, impede, stop, or restrict motion or movement and/or operation of the another object, member, structure, component, part, apparatus, system, or assembly.

As used herein, a "fastener", "fixation device", or "fastener system" refers to any structure configured, designed, or engineered to join two structures. Fasteners may be made of a variety of materials including metal, plastic, composite materials, metal alloys, plastic composites, and the like. Examples of fasteners include, but are not limited to screws, rivets, bolts, nails, snaps, hook and loop, set screws, bone screws, nuts, posts, pins, thumb screws, and the like. Other examples of fasteners include, but are not limited to wires, Kirschner wires (K-wire), anchors, bone anchors, plates, bone plates, intramedullary nails or rods or pins, implants, sutures, soft sutures, soft anchors, tethers, interbody cages, fusion cages, and the like.

In certain embodiments, the term fastener may refer to a fastener system that includes two or more structures configured to combine to serve as a fastener. An example of a fastener system is a rod or shaft having external threads and an opening or bore within another structure having corresponding internal threads configured to engage the external threads of the rod or shaft.

In certain embodiments, the term fastener may be used with an adjective that identifies an object or structure that the fastener may be particularly configured, designed, or engineered to engage, connect to, join, contact, or couple together with one or more other structures of the same or different types. For example, a "bone fastener" may refer to an apparatus for joining or connecting one or more bones, one or more bone portions, soft tissue and a bone or bone portion, hard tissue and a bone or bone portion, an apparatus and a bone or portion of bone, or the like.

In certain embodiments, a fastener may be a temporary fastener. A temporary fastener is configured to engage and serve a fastening function for a relatively short period of time. Typically, a temporary fastener is configured to be used until another procedure or operation is completed and/or until a particular event. In certain embodiments, a user may remove or disengage a temporary fastener. Alternatively, or in addition, another structure, event, or machine may cause the temporary fastener to become disengaged.

"Soft tissue" refers to tissue of a patient (i.e., human or animal) Examples of soft tissue include but are not limited to skin, ligament, tendon, fascia, fat muscle, fibrous tissue, blood vessels, lymph vessels, brain tissue, and/or nerves.

"Hard tissue" refers to any human or animal tissue that is not soft tissue. Examples of hard tissue include bone, teeth, tooth enamel, dentin, cementum, cartilage, or the like.

As used herein, a "fixator" refers to an apparatus, instrument, structure, device, component, member, system, assembly, or module structured, organized, configured, designed, arranged, or engineered to connect two bones or bone fragments or a single bone or bone fragment and another fixator to position and retain the bone or bone fragments in a desired position and/or orientation. Examples of fixators include both those for external fixation as well as those for internal fixation and include, but are not limited to pins, wires, Kirschner wires, screws, anchors, bone anchors, plates, bone plates, intramedullary nails or rods or pins, implants, interbody cages, fusion cages, and the like.

As used herein, an "anchor" refers to an apparatus, instrument, structure, member, part, device, component, system, or assembly structured, organized, configured, designed, arranged, or engineered to secure, retain, stop, and/or hold, an object to or at a fixed point, position, or location. An anchor may be coupled and/or connected to a flexible member such as a tether, chain, rope, wire, thread, suture, suture tape, or other like object. Alternatively, or in addition, an anchor may also be coupled, connected, and/or joined to a rigid object or structure. In certain embodiments, an anchor can be a fixation device. Said another way, a fixation device can function as an anchor. For example, an anchor pin is a pin, fastener, or K-wire that cooperates with a rigid structure to provide an anchor.

"Connector" refers to any structure configured, engineered, designed, adapted, and/or arranged to connect one structure, component, element, or apparatus to another structure, component, element, or apparatus. A connector can be rigid, pliable, elastic, flexible, and/or semiflexible. Examples of a connector include but are not limited to any fastener.

As used herein, a "sleeve" refers to structure that is narrow and longer longitudinally than the structure is wide. In certain embodiments, a sleeve serves to surround, enclose, wrap, and/or contain something else. In certain embodiments, a sleeve may surround, enclose, wrap, and/or contain a passage or void. (Search "sleeve" on wordhippo- .com. WordHippo, 2021. Web. Accessed 15 Nov. 2021. Modified.) In certain embodiments, the term sleeve may be preceded by an adjective that identifies the structure, implement, component or instrument that may be used with, inserted into or associated with the sleeve. For example, a "pin sleeve" may be configured to accept a pin or wire such as a K-wire, a "drive sleeve" may be configured to accept a drill or drill bit, a "fixation member sleeve" may be configured to accept a fastener or fixation member.

As used herein, a "long bone" refers to a bone of a patient having a length greater than a width of the bone. Long bone is one of five types of bones: long, short, flat, irregular and sesamoid. Long bones, especially the femur and tibia, can be subjected to most of the load during daily activities. Long bones grow primarily by elongation of the diaphysis, with an epiphysis at each end of the growing bone. The ends of epiphyses are covered with hyaline cartilage ("articular cartilage"). The longitudinal growth of long bones is a result of endochondral ossification at the epiphyseal plate. The long bone category type includes the femur, tibia, and fibula of the legs; the humerus, radius, and ulna of the arms; metacarpals and metatarsals of the hands and feet, the phalanges of the fingers and toes, and the clavicles or collar bones in humans or other patients. The outside of the long bone consists of a layer of connective tissue called the periosteum. Additionally, the outer shell of the long bone is compact bone, then a deeper layer of cancellous bone (spongy bone) which includes a medullary cavity that includes bone marrow. (Search "long bone" on Wikipedia-.com May 14, 2021. CC-BY-SA 3.0 Modified. Accessed Jul. 26, 2021.)

"Talar dome" refers to part of a talus bone. Specifically, the talar dome refers to the superior convex surface and/or area of the talus. The talar dome may also be referred to as a trochlea of the talus. The talar dome is part of the talus body.

"Bone fragment" or "fragment" refers to a part of a bone that is normally part of another bone of a patient. A bone fragment may be separate from another bone of a patient due to a deformity or trauma. In one aspect, the bone the bone fragment is normally connected or joined with is referred to as a parent bone.

As used herein, "manufacturing tool" or "fabrication tool" refers to a manufacturing or fabrication process, tool, system, or apparatus which creates an object, device, apparatus, feature, or component using one or more source materials. A manufacturing tool or fabrication tool can use a variety of manufacturing processes, including but not limited to additive manufacturing, subtractive manufacturing, forging, casting, and the like. The manufacturing tool can use a variety of materials including polymers, thermoplastics, metals, biocompatible materials, biodegradable materials, ceramics, biochemicals, and the like. A manufacturing tool may be operated manually by an operator, automatically using a computer numerical controller (CNC), or a combination of these techniques.

As used herein, "osteotomy procedure" or "surgical osteotomy" refers to a surgical operation in which one or more bones are cut to shorten or lengthen them or to change their alignment. The procedure can include removing one or more portions of bone and/or adding one or more portions of bone or bone substitutes. (Search "osteotomy" on Wikipedia.com Feb. 3, 22, 2021. CC-BY-SA 3.0 Modified. Accessed Feb. 15, 2022.)

As used herein, "patient-specific osteotomy procedure" refers to an osteotomy procedure that has been adjusted, tailored, modified, or configured to specifically address the anatomy, physiology, condition, abnormalities, needs, or desires of a particular patient. In certain aspects, one patient-specific osteotomy procedure may be useable in connection with only one patient. In other aspects, one patient-specific osteotomy procedure may be useable with a number of patients having a particular class of characteristics. In certain aspects, a patient-specific osteotomy procedure may refer to a non-patient-specific osteotomy procedure that includes one or more patient-specific implants and/or instrumentation. In another aspects, a patient-specific osteotomy procedure may refer to a patient-specific osteotomy procedure that includes one or more patient-specific implants, patient-specific surgical steps, and/or patient-specific instrumentation.

"Register" or "Registration" refers to an act of aligning, mating, contacting, engaging, or coupling one or more parts and/or surfaces of one object in relation to one or more parts and/or surfaces of another object. Often, the one or more parts and/or surfaces of one object include protrusions and/or depressions that are the inverse or mirror configuration of protrusions and/or depressions of one or more parts and/or surfaces of the other object.

"Remediation procedure" refers to any designed or performed for the purpose of remediating a condition of a patient and/or a condition of one or more parts of a body of a patient.

"Wedge osteotomy" refers to an osteotomy procedure in which one or more wedges are used as part of the procedure. Generally, wedge osteotomies can be of one of two types, open wedge and closing wedge. The type of osteotomy refers to how the procedure changes the relation between two parts of a bone involved in the osteotomy. In an open wedge osteotomy, a wedge of bone or graft or other material is inserted in between two parts of a bone. Consequently, a wedge shape is "opened" in the bone. In a close wedge osteotomy or closing wedge osteotomy a wedge of bone is removed from a bone. Consequently, a wedge shape formed in the bone is "closed."

As used herein, an "opening" refers to a gap, a hole, an aperture, a port, a portal, a slit, a space or recess in a structure, a void in a structure, or the like. In certain embodiments, an opening can refer to a structure configured specifically for receiving something and/or for allowing access. In certain embodiments, an opening can pass through a structure. In such embodiments, the opening can be referred to as a window. In other embodiments, an opening can exist within a structure but not pass through the structure. In other embodiments, an opening can initiate on a surface or at an edge or at a side of a structure and extend into the structure for a distance, but not pass through or extend to another side or edge of the structure. In other embodiments, an opening can initiate on a surface or at an edge or at a side of a structure and extend into the structure until the opening extends through or extends to another side or edge of the structure.

An opening can be two-dimensional or three-dimensional and can have a variety of geometric shapes and/or cross-sectional shapes, including, but not limited to a rectangle, a square, or other polygon, as well as a circle, an ellipse, an ovoid, or other circular or semi-circular shape. As used herein, the term "opening" can include one or more modifiers that define specific types of "openings" based on the purpose, function, operation, position, or location of the "opening." As one example, a "fastener opening" refers to an "opening" adapted, configured, designed, or engineered to accept or accommodate a "fastener."

"Hole" refers to a gap, an opening, an aperture, a port, a portal, a space or recess in a structure, a void in a structure, or the like. In certain embodiments, a hole can refer to a structure configured specifically for receiving something and/or for allowing access. In certain embodiments, a hole can pass through a structure. In other embodiments, an opening can exist within a structure but not pass through the structure. A hole can be two-dimensional or three-dimensional and can have a variety of geometric shapes and/or cross-sectional shapes, including, but not limited to a rectangle, a square, or other polygon, as well as a circle, an ellipse, an ovoid, or other circular or semi-circular shape. As used herein, the term "hole" can include one or more modifiers that define specific types of "holes" based on the purpose, function, operation, position, or location of the "hole." As one example, a "fastener hole" refers to an "hole" adapted, configured, designed, or engineered to accept or accommodate a "fastener." A "blind hole" is a hole with an opening on one side that does not extend all the way through a structure. In certain embodiments, a hole, including a blind hole, has a circular longitudinal cross-section. Alternatively, or in addition, a hole can have a cross-section of a variety of geometric shapes include a circle, an oval, a square, a rectangle, a slot with rounded ends, a triangle, or the like.

As used herein, "anatomic data" refers to data identified, used, collected, gathered, and/or generated in connection with an anatomy of a human or animal. Examples of anatomic data may include location data for structures, both independent, and those connected to other structures within a coordinate system. Anatomic data may also include data that labels or identifies one or more anatomical structures. Anatomic data can include volumetric data, material composition data, and/or the like. Anatomic data can be generated based on medical imaging data or measurements using a variety of instruments including monitors and/or sensors. Anatomic data can be gathered, measured, or collected from anatomical models and/or can be used to generate, manipulate, or modify anatomical models.

A "bone model" or "anatomic model" refers to a model of a bone of a person. The bone model may model a single bone or a plurality of bones. The modeled bone and/or bones may be positioned in standard anatomical form and/or may be positioned relative to other bones (e.g., models of bones) of a person such that the positions of the bones in the bone model are the same or substantially the same as corresponding bones of a person, such as a patient. A bone model or anatomic model of a patient's body or body part(s) may be generated by computing devices that analyze medical imaging images. Structures of a patient's body can be determined using a process called segmentation.

"Patient specific" refers to a feature, an attribute, a characteristic, a structure, function, structure, device, guide, tool, instrument, apparatus, member, component, system, assembly, module, or subsystem or the like that is adjusted, tailored, modified, organized, configured, designed, arranged, engineered, and/or fabricated to specifically address the anatomy, physiology, condition, abnormalities, needs, or desires of a particular patient or surgeon serving the particular patient. In one aspect, a patient specific attribute or feature is unique to a single patient and may include features unique to the patient such as a number of cut channels, a number of bone attachment features, a number of bone engagement surfaces, a number of resection features, a depth of one or more cutting channels, an angle for one or more resection channels, a surface contour, component position, component orientation, a trajectory for an instrument, implant, or anatomical part of a patient, a lateral offset, and/or other features.

"Trajectory guide" or "trajectory indicator" or "targeting guide" refers to any structure, apparatus, surface, device, system, feature, or aspect configured to indicate, identify, guide, place, position, or otherwise assist in marking or deploying a fastener or other structure along a desired trajectory for one or more subsequent steps in a procedure.

"Trajectory" refers to a path a body travels or a path configured for a body to travel through space. (Search "trajectory" on wordhippo.com. WordHippo, 2023. Web. Modified. Accessed 13 Jun. 2023.)

As used herein, "side" refers to a structure or part of a structure including, but not limited to one of a longer bounding surfaces or lines of an object especially contrasted with the ends, a line or surface forming a border or face of an object, either surface of a thin object, a bounding line or structure of a geometric figure or shape, and the like. (search "side" on Merriam-Webster.com. Merriam-Webster, 2021. Web. 3 Aug. 2021. Modified.) A side can also refer to a geometric edge of a polygon (two-dimensional shape) and/or a face or surface of a polyhedron (three-dimensional shape). (Search "side" on Wikipedia.com Jul. 21, 2021. CC-BY-SA 3.0 Modified. Accessed Aug. 3, 2021.) Side can also refer to a location on a structure. For example, a side can be a location on a structure at, or near, a furthest position away from a central axis of the structure. As used herein, the term "side" can include one or more modifiers that define and/or orient and/or distinguish the side of an object from others based on based on where and/or how the object is deployed within or in relation to a second object. For example, in the context of an implant for a patient, sides of the implant may be labeled based on where the sides are relative to the patient when the implant is deployed. As one example, an "anterior side" of an implant, instrument, anatomical structure, or other structure refers to a side that is anterior to other sides of the structure in relation to a patient when the structure is deployed in the patient. As another example, in the context of an instrument used with a patient, sides of the instrument may be labeled based on where the sides are when the instrument is being used for its purpose. As one example, a "front side" of an instrument refers to a side that is facing a user of the instrument when the instrument is in use.

As used herein, a "guard" refers to an apparatus, instrument, structure, member, device, component, system, or assembly structured, organized, configured, designed, arranged, or engineered to prevent, limit, impede, stop, or restrict motion, action, or movement and/or operation of the another object, member, structure, component, part, apparatus, system, or assembly beyond a certain parameter such as a boundary. Said another way, a "guard" refers to an apparatus, instrument, structure, member, device, component, system, or assembly structured, organized, configured, designed, arranged, or engineered to retain, maintain, hold, keep, or restrict motion, action, or movement and/or operation of the another object, member, structure, component, part, apparatus, system, or assembly within or at one or more parameters such as a boundary.

As used herein, "artificial intelligence" refers to intelligence demonstrated by machines, unlike the natural intelligence displayed by humans and animals, which involves consciousness and emotionality. The distinction between artificial intelligence and natural intelligence categories is often revealed by the acronym chosen. 'Strong' AI is usually labelled as artificial general intelligence (AGI) while attempts to emulate 'natural' intelligence have been called artificial biological intelligence (ABI). Leading AI textbooks define the field as the study of "intelligent agents": any device that perceives its environment and takes actions that maximize its chance of achieving its goals. The term "artificial intelligence" can also be used to describe machines that mimic "cognitive" functions that humans associate with the human mind, such as "learning" and "problem solving". (Search "artificial intelligence" on Wikipedia.com Jun. 25, 2021. CC-BY-SA 3.0 Modified. Accessed Jun. 25, 2021.)

As used herein, "segmentation" or "image segmentation" refers to the process of partitioning an image into different meaningful segments. These segments may correspond to different tissue classes, organs, pathologies, bones, or other biologically relevant structures. Medical image segmentation accommodates imaging ambiguities such as low contrast, noise, and other imaging ambiguities.

Certain computer vision techniques can be used or adapted for image segmentation. For example, the techniques and or algorithms for segmentation may include, but are not limited to: Atlas-Based Segmentation: For many applications, a clinical expert can manually label several images; segmenting unseen images is a matter of extrapolating from these manually labeled training images. Methods of this style are typically referred to as atlas-based segmentation methods. Parametric atlas methods typically combine these training images into a single atlas image, while nonparametric atlas methods typically use all of the training images separately. Atlas-based methods usually require the use of image registration in order to align the atlas image or images to a new, unseen image.

Image registration is a process of correctly aligning images; Shape-Based Segmentation: Many methods parametrize a template shape for a given structure, often relying on control points along the boundary. The entire shape is then deformed to match a new image. Two of the most common shape-based techniques are Active Shape Models and Active Appearance Models; Image-Based Segmentation: Some methods initiate a template and refine its shape according to the image data while minimizing integral error measures, like the Active contour model and its variations; Interactive Segmentation: Interactive methods are useful when clinicians can provide some information, such as a seed region or rough outline of the region to segment. An algorithm can then iteratively refine such a segmentation, with or without guidance from the clinician. Manual segmentation, using tools such as a paint brush to explicitly define the tissue class of each pixel, remains the gold standard for many imaging applications. Recently, principles from feedback control theory have been incorporated into segmentation, which give the user much greater flexibility and allow for the automatic correction of errors; Subjective surface Segmentation: This method is based on the idea of evolution of segmentation function which is governed by an advection-diffusion model. To segment an object, a segmentation seed is needed (that is the starting point that determines the approximate position of the object in the image). Consequently, an initial segmentation function is constructed. With the subjective surface method, the position of the seed is the main factor determining the form of this segmentation function; and Hybrid segmentation which is based on combination of methods. (Search "medical image computing" on Wikipedia.com Jun. 24, 2021. CC-BY-SA 3.0 Modified. Accessed Jun. 24, 2021.)

As used herein, "medical imaging" refers to a technique and process of imaging the interior of a body for clinical analysis and medical intervention, as well as visual representation of the function of some organs or tissues (physiology). Medical imaging seeks to reveal internal structures hidden by the skin and bones, as well as to diagnose and treat disease. Medical imaging may be used to establish a database of normal anatomy and physiology to make possible identification of abnormalities. Medical imaging in its widest sense, is part of biological imaging and incorporates radiology, which uses the imaging technologies of X-ray radiography, magnetic resonance imaging, ultrasound, endoscopy, elastography, tactile imaging, thermography, medical photography, nuclear medicine functional imaging techniques as positron emission tomography (PET) and single-photon emission computed tomography (SPECT). Another form of X-ray radiography includes computerized tomography (CT) scans in which a computer controls the position of the X-ray sources and detectors. Magnetic Resonance Imaging (MRI) is another medical imaging technology. Measurement and recording techniques that are not primarily designed to produce images, such as electroencephalography (EEG), magnetoencephalography (MEG), electrocardiography (ECG), and others, represent other technologies that produce data susceptible to representation as a parameter graph vs. time or maps that contain data about the measurement locations. In certain embodiments bone imaging includes devices that scan and gather bone density anatomic data. These technologies may be considered forms of medical imaging in certain disciplines. (Search "medical imaging" on Wikipedia.com Jun. 16, 2021. CC-BY-SA 3.0 Modified. Accessed Jun. 23, 2021.) Data, including images, text, and other data associated with medical imaging is referred to as patient imaging data. As used herein, "patient imaging data" refers to data identified, used, collected, gathered, and/or generated in connection with medical imaging and/or medical imaging data. Patient imaging data can be shared between users, systems, patients, and professionals using a common data format referred to as Digital Imaging and Communications in Medicine (DICOM) data. DICOM data is a standard format for storing, viewing, retrieving, and sharing medical images.

As used herein, "medical image computing" or "medical image processing" refers to systems, software, hardware, components, and/or apparatus that involve and combine the fields of computer science, information engineering, electrical engineering, physics, mathematics and medicine. Medical image computing develops computational and mathematical methods for working with medical images and their use for biomedical research and clinical care. One goal for medical image computing is to extract clinically relevant information or knowledge from medical images. While closely related to the field of medical imaging, medical image computing focuses on the computational analysis of the images, not their acquisition. The methods can be grouped into several broad categories: image segmentation, image registration, image-based physiological modeling, and others. (Search "medical image computing" on Wikipedia.com Jun. 24, 2021. CC-BY-SA 3.0 Modified. Accessed Jun. 24, 2021.) Medical image computing may include one or more processors or controllers on one or more computing devices. Such processors or controllers may be referred to herein as medical image processors. Medical imaging and medical image computing together can provide systems and methods to image, quantify and fuse both structural and functional information about a patient in vivo. These two technologies include the transformation of computational models to represent specific subjects/patients, thus paving the way for personalized computational models. Individualization of generic computational models through imaging can be realized in three complementary directions: definition of the subject-specific computational domain (anatomy) and related subdomains (tissue types); definition of boundary and initial conditions from (dynamic and/or functional) imaging; and characterization of structural and functional tissue properties. Medical imaging and medical image computing enable the translation of models to the clinical setting with both diagnostic and therapeutic applications. (Id.) In certain embodiments, medical image computing can be used to generate a bone model, a patient-specific model, and/or a patent specific instrument from medical imaging and/or medical imaging data.

As used herein, "model" refers to an informative representation of an object, person or system. Representational models can be broadly divided into the concrete (e.g. physical form) and the abstract (e.g. behavioral patterns, especially as expressed in mathematical form). In abstract form, certain models may be based on data used in a computer system or software program to represent the model. Such models can be referred to as computer models. Computer models can be used to display the model, modify the model, print the model (either on a 2D medium or using a 3D printer or additive manufacturing technology). Computer models can also be used in environments with models of other objects, people, or systems. Computer models can also be used to generate simulations, display in virtual environment systems, display in augmented reality systems, or the like. Computer models can be used in Computer Aided Design (CAD) and/or Computer Aided Manufacturing (CAM) systems. Certain models may be identified with an adjective that identifies the object, person, or system the model represents. For example, a "bone" model is a model of a bone, and a "heart" model is a model of a heart. (Search "model" on Wikipedia.com Jun. 13, 2021. CC-BY-SA 3.0 Modified. Accessed Jun. 23, 2021.)

As used herein, "additive manufacturing" refers to a manufacturing process in which materials are joined together in a process that repeatedly builds one layer on top of another to generate a three-dimensional structure or object. Additive manufacturing may also be referred to using different terms including additive processes, additive fabrication, additive techniques, additive layer manufacturing, layer manufacturing, freeform fabrication, ASTM F2792 (American Society for Testing and Materials), and 3D printing. Additive manufacturing can build the three-dimensional structure or object using computer-controlled equipment that applies successive layers of the material(s) based on a three-dimensional model that may be defined using Computer Aided Design (CAD) software. Additive manufacturing can use a variety of materials including polymers, thermoplastics, metals, ceramics, biochemicals, and the like. Additive manufacturing may provide unique benefits, as an implant together with the pores and/or lattices can be directly manufactured (without the need to generate molds, tool paths, perform any milling, and/or other manufacturing steps).

"Repository" refers to any data source or dataset that includes data or content. In one embodiment, a repository resides on a computing device. In another embodiment, a repository resides on a remote computing or remote storage device. A repository may comprise a file, a folder, a directory, a set of files, a set of folders, a set of directories, a database, an application, a software application, content of a text, content of an email, content of a calendar entry, and the like. A repository, in one embodiment, comprises unstructured data. A repository, in one embodiment, comprises structured data such as a table, an array, a queue, a look up table, a hash table, a heap, a stack, or the like. A repository may store data in any format including binary, text, encrypted, unencrypted, a proprietary format, or the like.

As used herein, "registration" or "image registration" refers to a method, process, module, component, apparatus, and/or system that seeks to achieve precision in the alignment of two images. As used here, "image" may refer to either or both an image of a structure or object and another image or a model (e.g., a computer-based model or a physical model, in either two dimensions or three dimensions). In the simplest case of image registration, two images are aligned. One image may serve as the target image and the other as a source image; the source image is transformed, positioned, realigned, and/or modified to match the target image. An optimization procedure may be applied that updates the transformation of the source image based on a similarity value that evaluates the current quality of the alignment. An iterative procedure of optimization may be repeated until a (local) optimum is found. An example is the registration of CT and PET images to combine structural and metabolic information. Image registration can be used in a variety of medical applications: Studying temporal changes; Longitudinal studies may acquire images over several months or years to study long-term processes, such as disease progression. Time series correspond to images acquired within the same session (seconds or minutes). Time series images can be used to study cognitive processes, heart deformations and respiration; Combining complementary information from different imaging modalities. One example may be the fusion of anatomical and functional information.

Since the size and shape of structures vary across modalities, evaluating the alignment quality can be more challenging. Thus, similarity measures such as mutual information may be used; Characterizing a population of subjects. In contrast to intra-subject registration, a one-to-one mapping may not exist between subjects, depending on the structural variability of the organ of interest. Inter-subject registration may be used for atlas construction in computational anatomy. Here, the objective may be to statistically model the anatomy of organs across subjects; Computer-assisted surgery: in computer-assisted surgery pre-operative images such as CT or MRI may be registered to intra-operative images or tracking systems to facilitate image guidance or navigation. There may be several considerations made when performing image registration: The transformation model. Common choices are rigid, affine, and deformable transformation models. B-spline and thin plate spline models are commonly used for parameterized transformation fields. Non-parametric or dense deformation fields carry a displacement vector at every grid location; this may use additional regularization constraints. A specific class of deformation fields are diffeomorphisms, which are invertible transformations with a smooth inverse; The similarity metric. A distance or similarity function is used to quantify the registration quality. This similarity can be calculated either on the original images or on features extracted from the images. Common similarity measures are sum of squared distances (SSD), correlation coefficient, and mutual information. The choice of similarity measure depends on whether the images are from the same modality; the acquisition noise can also play a role in this decision. For example, SSD may be the optimal similarity measure for images of the same modality with Gaussian noise. However, the image statistics in ultrasound may be significantly different from Gaussian noise, leading to the introduction of ultrasound specific similarity measures.

Multi-modal registration may use a more sophisticated similarity measure; alternatively, a different image representation can be used, such as structural representations or registering adjacent anatomy; The optimization procedure. Either continuous or discrete optimization is performed. For continuous optimization, gradient-based optimization techniques are applied to improve the convergence speed. (Search "medical image computing" on Wikipedia.com Jun. 24, 2021. CC-BY-SA 3.0 Modified. Accessed Jun. 25, 2021.)

As used herein, a "resection" refers to a method, procedure, or step that removes tissue from another anatomical structure or body. A resection is typically performed by a surgeon on a part of a body of a patient. (Search "surgery" on Wikipedia.com May 26, 2021. CC-BY-SA 3.0 Modified. Accessed May 26, 2021.) Resection may be used as a noun or a verb. In the verb form, the term is "resect" and refers to an act of performing, or doing, a resection. Past tense of the verb resect is resected.

"Minimally invasive surgery" or "minimal invasive surgery" (MIS surgery) refers to one or more surgical techniques that limits the size of incisions needed for a surgical procedure, thereby reducing wound healing time, associated pain, and risk of infection. Surgery by definition is invasive, and many operations requiring incisions of some size are referred to as open surgery. (Search "minimally invasive surgery" on Wikipedia.com Jan. 29, 2023. CC-BY-SA 3.0 Modified. Accessed Jan. 30, 2023.)

"Bone condition" refers to any of a variety of conditions of bones of a patient. Generally, a bone condition refers to an orientation, position, and/or alignment of one or more bones of the patient relative to other anatomical structures of the body of the patient. Bone conditions may be caused by or result from deformities, misalignment, malrotation, fractures, joint failure, and/or the like. A bone condition includes, but is not limited to, any angular deformities of one or more bone segments in either the lower or upper extremities (for example, tibial deformities, calcaneal deformities, femoral deformities, and radial deformities). Alternatively, or in addition, "bone condition" can refer to the structural makeup and configuration of one or more bones of a patient. Thus bone condition may refer to a state or condition of regions, a thickness of a cortex, bone density, a thickness and/or porosity of internal regions (e.g. whether it is calcaneus or solid) of the bone or parts of the bone such as a head, a base, a shaft, a protuberance, a process, a lamina, a foramen, and the like of a bone, along the metaphyseal region, epiphysis region, and/or a diaphyseal region. "Malrotation" refers to a condition in which a part, typically a part of a patient's body has rotated from a normal position to an unnormal or uncommon position.

An "active compression instrument" refers to a mechanical device, apparatus, member, object, body, component, or structure, which is organized, configured, designed, arranged, or engineered to maintain two objects in a compressed state one against the other while a user performs one or more other operations, method steps, or activities. One example of an active compression instrument is a compressor or an instrument that can function as both a compressor and a distractor.

"Compressor" refers to any apparatus, device, or system that can function as an active compression instrument. A compressor functions to bring two objects closer to or in contact with each other. "Distractor" refers to any apparatus, device, or system that can function as an active distraction instrument. An active distraction instrument performs an opposite function to that of an active compression instrument, an active distraction instrument functions to separate two objects from each other. In certain embodiments, an active distraction instrument can serves as both an active distraction instrument and an active compression instrument.

As used herein, a "guide" refers to a part, component, member, or structure designed, adapted, configured, or engineered to guide or direct one or more other parts, components, or structures. A guide may be part of, integrated with, connected to, attachable to, or coupled to, another structure, device, or instrument. In one embodiment, a guide may include a modifier that identifies a particular function, location, orientation, operation, type, and/or a particular structure of the guide. Examples of such modifiers applied to a guide, include, but are not limited to, "pin guide" that guides or directs one or more pins, a "cutting guide" that guides or directs the making or one or more cuts, a placement, deployment, or insertion guide that guides or directs the placement, positioning, orientation, deployment, installation, or insertion of a fastener and/or implant, a "cross fixation guide" that guides deployment of a fastener or fixation member, an "alignment guide" that guides the alignment of two or more objects or structures, a "navigation guide" that guides a user in navigating a course or process or procedure such as a surgical procedure, a "resection guide" that serves to guide resection of soft or hard tissue, such as in an osteotomy, a "reduction guide" can serve to guide reduction of one or more bone segments or fragments, an "placement guide" that serves to identify how an object can be placed in relation to another object or structure, and the like. Furthermore, guides may include modifiers applied due to the procedure or location within a patient for which the guide is to be used. For example, where a guide is used at a joint, the guide may be referred to herein as an "arthrodesis guide".

As used herein, "feature" refers to a distinctive attribute or aspect of something. (Search "feature" on google.com. Oxford Languages, 2021. Web. 20 Apr. 2021.) A feature may include one or more apparatuses, structures, objects, systems, sub-systems, devices, or the like. A feature may include a modifier that identifies a particular function or operation and/or a particular structure relating to the feature. Examples of such modifiers applied to a feature, include, but are not limited to, "attachment feature," "securing feature," "placement feature," "protruding feature," "engagement feature," "disengagement feature," "resection feature", "guide feature", "alignment feature", and the like.

"View" refers to a sight, scene, or prospect that can be taken in by the eye from a particular place. (Search "view" on wordhippo.com. WordHippo, 2023. Web. Modified. Accessed 8 Jan. 2024.)

"Crosshair" refers to a pair of perpendicular lines or wires of an instrument. A crosshair aids in focusing and alignment by providing a central reference point. (© ChatGPT August 3.5 Version, Modified, accessed chat.openai.com/chat Jan. 8, 2024).

"Cortical bone" refers to a type of bone tissue. Cortical bone is a type of bone tissue typically found between an external surface of a bone and an interior area of the bone. Cortical bone is more dense and typically stronger structurally than other types of bone tissue. "Cortical surface" refers to a surface of cortical bone.

"Transosseous placement feature" refers to a placement feature that extends through one or more bones and that enables, or facilitates, placement of another device, apparatus, or instrument.

"Patient specific feature" refers to a feature, function, structure, device, guide, tool, instrument, apparatus, member, component, system, assembly, module, or subsystem that is adjusted, tailored, modified, organized, configured, designed, arranged, engineered, and/or fabricated to specifically address the anatomy, physiology, condition, abnormalities, needs, or desires of a particular patient or surgeon serving the particular patient. In one aspect, a patient specific feature is unique to a single patient and may include features unique to the patient such as a number of cut channels, a number of bone attachment features, a number of bone engagement surfaces, a number of resection features, a depth of one or more cutting channels, an angle for one or more resection channels, a surface contour, component position, component orientation, and/or other features. "Medial resection guide" refers to a resection guide designed, engineered, fabricated, or intended for use with, one, in, or about a medial part, section, surface, portion, or aspect of an anatomical structure such as a bone, digit, limb, or other anatomical structure for one or more steps of a resection procedure. "Lateral resection guide" refers to a resection guide designed, engineered, fabricated, or intended for use with, one, in, or about a lateral part, section, surface, portion, or aspect of an anatomical structure such as a bone, digit, limb, or other anatomical structure for one or more steps of a resection procedure.

"Cut surface" refers to a surface of an object that is created or formed by the removal of one or more parts of the object that includes the original surface. Cut surfaces can be created using a variety of methods, tools, or apparatuses and may be formed using a variety of removal actions, including, but not limited to, fenestrating, drilling, abrading, cutting, sawing, chiseling, digging, scrapping, and the like. Tools and/or methods used for forming a cut surface can include manual, mechanical, motorized, hydraulic, automated, robotic, and the like. In certain embodiments, the cut surface(s) are planar.

"Orientation" refers to a direction, angle, position, condition, state, or configuration of a first object, component, part, apparatus, system, or assembly relative to another object, component, part, apparatus, system, assembly, reference point, reference axis, or reference plane.

"Longitudinal axis" refers to an axis of a structure, device, object, apparatus, or part thereof that extends from one end of a longest dimension to an opposite end. Typically, a longitudinal axis passes through a center of the structure, device, object, apparatus, or part thereof along the longitudinal axis. The center point used for the longitudinal axis may be a geometric center point and/or a mass center point.

Those of skill in the art will appreciate that a resection feature may take a variety of forms and may include a single feature or one or more features that together form the resection feature. In certain embodiments, the resection feature may take the form of one or more slots. Alternatively, or in addition, a resection feature may be referenced using other names including, but not limited to, channel, cut channels, and the like.

"Cutting tool" refers to any tool that can be used to cut or resect another object. In particular, a cutting tool can refer to a manual or power tool for cutting or resecting tissue of a patient. Examples of cutting tools include, but are not limited to, a burr, an oscillating saw, a reciprocating saw, a grater saw, a drill, a mill, a side-cutting burr, a pivoting burr, a pivoting resection guide, a pivoting drill bit, or the like.

"Resection guide feature" refers to any guide feature configured, designed, engineered and/or intended to facilitate resection. Examples of a resection guide feature include but are not limited to, a cut channel, a cut slot, a slot, a pivoting cut guide, a pivoting resection guide, an opening, a hole, or the like.

As used herein, an "indicator" refers to an apparatus, device, component, system, assembly, mechanism, hardware, software, firmware, circuit, module, set of data, text, number, code, symbol, a mark, or logic structured, organized, configured, programmed, designed, arranged, or engineered to convey information or indicate a state, condition, mode, context, location, or position to another apparatus, device, component, system, assembly, mechanism, hardware, software, firmware, circuit, module, and/or a user of an apparatus, device, component, system, assembly, mechanism, hardware, software, firmware, circuit, module that includes, or is associated with the indicator. The indicator can include one or more of an audible signal, a token, a presence of a signal, an absence of a signal, a tactile signal, a visual signal or indication, a visual marker, a visual icon, a visual symbol, a visual code, a visual mark, and/or the like. In certain embodiments, "indicator" can be used with an adjective describing the indicator. For example, a "mode indicator" is an indicator that identifies or indicates a mode.

"Position" refers to a place or location. (Search "position" on wordhippo.com. WordHippo, 2024. Web. Accessed 8 Jan. 2024.) A position may be defined in a virtual environment such as in a model or set of models defined by and presented by a computing device. In addition, a position may be a place or location in a tangible physical environment such as in a space, on land, within or on a system, assembly, component, or other structure.

"Position indicator" refers to any apparatus, structure, device, system, and/or component organized, configured, designed, engineered, and/or arranged to serve as an indicator of a position for one or more things, objects, structures, apparatuses, systems, features, aspects, attributes or the like. Examples of a position indicator include, but are not limited to, a crosshair, cross hairs, a pin, a wire, a fastener, a hole, an opening, a post, a prong, a probe, a needle, an arrow, a marking, or the like. In certain embodiments, an indicator may communicate a position of one structure or component or system in relation to another. A position indicator may indicate a position of one object relative to another, may indicate a relationship between two objects, may indicate a trajectory of one object relative to another, or the like.

As used herein, a "marking" or "marker" refers to a symbol, letter, lettering, word, phrase, icon, design, color, diagram, indicator, figure, or combination of these designed, intended, structured, organized, configured, programmed, arranged, or engineered to communication information and/or a message to a user receiving, viewing, or encountering the marking. The marking can include one or more of a tactile signal, a visual signal or indication, an audible signal, and the like. In one embodiment, a marking may comprise a number or set letters, symbols, or words positioned on a surface, structure, color, color scheme, or device to convey a desired message or set of information.

"Reference" refers to any apparatus, structure, device, system, component, marking, and/or indicator organized, configured, designed, engineered, and/or arranged to serve as a source of information or a point of comparison used to support or establish knowledge, truth, or quality. (© ChatGPT January 9 Version, Modified, accessed chat.openai.com/chat Jan. 28, 2023). In certain embodiments, a reference can serve as a starting point or initial position for one or more steps in a surgical procedure.

As used herein, "edge" refers to a structure, boundary, or line where an object, surface, or area begins or ends. An edge can also refer to a boundary or perimeter between two structures, objects, or surfaces. An edge can also refer to a narrow part adjacent to a border. (search "edge" on Merriam-Webster.com. Merriam-Webster, 2021. Web. 3 Aug. 2021. Modified.) In certain embodiments, an edge can be a one dimensional or a two-dimensional structure that joins two adjacent structures or surfaces. Furthermore, an edge may be at a perimeter of an object or within a perimeter or boundary of an object.

As used herein, "end" refers to a part or structure of an area or span that lies at the boundary or edge. An end can also refer to a point that marks the extent of something and/or a point where something ceases to exist. An end can also refer to an extreme or last part lengthwise of a structure or surface. (search "end" on Merriam-Webster.com. Merriam-Webster, 2021. Web. 4 Aug. 2021. Modified.)

"Anatomical structure" refers to any part or portion of a part of a body of a person, animal, or other patient. Examples of anatomical structures, include but are not limited to, a bone, bones, soft tissue, a joint, joints, skin, hard tissue, teeth, mouth, eyes, hair, nails, fingers, toes, legs, arms, torso, vertebrae, ligaments, tendons, organs, or the like.

"Anatomical reference" refers to any reference that is, or is on, or is in, is part of, is connected to, is coupled to, or is otherwise associated with an anatomical structure. Examples of anatomical structures, include but are not limited to, a bone, bones, soft tissue, a joint, joints, skin, hard tissue, teeth, mouth, eyes, hair, nails, fingers, toes, legs, arms, torso, vertebrae, ligaments, tendons, organs, a hole, a post, a plurality of holes, a plurality of posts, or the like. An anatomical reference can be used as a reference or landmark for one or more steps, stages, and/or aspects, or activities in connection with a procedure, including, but not limited to, a surgical procedure.

As used herein, an "interface," "user interface," or "engagement interface" refers to an area, a boundary, structure, or a place at which two separate and/or independent structures, members, apparatus, assemblies, components, and/or systems join, connect, are coupled, or meet and act on, or communicate, mechanically and/or electronically, with each other. In certain embodiments, "interface" may refer to a surface forming a common boundary of two bodies, spaces, structures, members, apparatus, assemblies, components, or phases. (search "interface" on Merriam-Webster.com. Merriam-Webster, 2021. Web. 15 Nov. 2021. Modified.) In certain embodiments, the term interface may be used with an adjective that identifies a type or function for the interface. For example, an engagement or coupling interface may refer to one or more structures that interact, connect, or couple to mechanically join or connect two separate structures, each connected to a side of the interface. In another example, a user interface may refer to one or more mechanical, electrical, or electromechanical structures that interact with or enable a user to provide user input, instructions, input signals, data, or data values and receive output, output data, or feedback.

The present disclosure discloses surgical systems and methods by which a bone condition, which can include a deformity, may be corrected or otherwise addressed. Known methods of addressing bone conditions are often limited to a finite range of discretely sized instruments. A patient with an unusual condition, or anatomy that falls between instrument sizes, may not be readily treated with such systems.

Furthermore, patient-specific guides may be used for various other procedures on the foot, or on other bones of the musculoskeletal system. For example, patient-specific guides may be used for various procedures involving determining ligament or tendon attachment or anchoring points, determining where to form bone tunnels or position anchors, tendon or graft deployment, and the like.

FIG. 1A is a flowchart diagram depicting a method 100 for correcting a bone condition, according to one embodiment. The method 100 may be used for any of a wide variety of bone conditions, including but not limited to deformities, fractures, joint failure, and/or the like. Further, the method 100 may provide correction with a wide variety of treatments, including but not limited to arthroplasty, arthrodesis, fracture repair, and/or the like.

As shown, the method 100 may begin with a step 102 in which a CT scan (or another three-dimensional image, also referred to as medical imaging) of the patient's anatomy is obtained. The step 102 may include capturing a scan of only the particular bone(s) to be treated, or may include capture of additional anatomic information, such as the surrounding tissues. Additionally, or alternatively, the step 102 may include receiving a previously captured image, for example, at a design and/or fabrication facility. Performance of the step 102 may result in possession of a three-dimensional model of the patient's anatomy, or three-dimensional surface points that can be used to construct such a three-dimensional model.

After the step 102 has been carried out, the method 100 may proceed to a step 104 in which a CAD model of the patient's anatomy (including one or more bones) is generated. The CAD model may be one example of a bone model. The CAD model may be of any known format, including but not limited to SolidWorks, Catia, AutoCAD, or DXF. In some embodiments, customized software may be used to generate the CAD model from the CT scan. The CAD model may only include the bone(s) to be treated and/or may include surrounding tissues. In alternative embodiments, the step 104 may be omitted, as the CT scan may capture data that can directly be used in future steps without the need for conversion.

In one embodiment, the CAD model generated and/or patient-specific instrumentation, implants, and/or plan for conducting an operative procedure, may be enhanced by the use of advanced computer analysis system, machine learning, and/or automated/artificial intelligence. For example, these technologies may be used to revise a set of steps for a procedure such that a more desirable outcome is achieved.

In a step 106, the CAD model and/or CT scan data may be used to model patient-specific instrumentation that can be used to correct the condition, as it exists in the patient's anatomy. In some embodiments, any known CAD program may be used to view and/or manipulate the CAD model and/or CT scan and generate one or more instruments that are matched specifically to the size and/or shape of the patient's bone(s). In some embodiments, such instrumentation may include a targeting guide, trajectory guide, drill guide, resection guide, cutting guide, tendon trajectory guide, capital fragment positioning guide, or similar guide that can be attached to one or more bones, with one or more features that facilitate work on the one or more bones pursuant to a procedure such as arthroplasty or arthrodesis. In some embodiments, performance of the step 106 may include modelling an instrument with a bone engagement surface that is shaped to match the contour of a surface of the bone, such that the bone engagement surface can lie directly on the corresponding contour.

In a step 108, the model(s) may be used to manufacture patient-specific instrumentation and/or implants. This may be done via any known manufacturing method, including casting, forging, milling, additive manufacturing, and/or the like. Additive manufacturing may provide unique benefits, as the model may be directly used to manufacture the instrumentation and/or implants (without the need to generate molds, tool paths, and/or the like beforehand). Such instrumentation may optionally include a targeting guide, trajectory guide, drill guide, resection guide, dissection guide, cutting guide, positioner, positioning guide, tendon trajectory guide, or the like.

In addition to, or in the alternative to the step 108, the model(s) may be used to select from available sizes of implants and/or instruments or instruments having various attributes and advise the surgeon accordingly. For example, where a range of guides are available for a given procedure, analysis of the CAD data may facilitate pre-operative selection of the optimal guide and/or optimal placement of the guide on the bone. Similarly, if a range of implants and/or instruments may be used for a given procedure, analysis of the CAD data may facilitate pre-operative selection of the optimal implant(s). More particularly, properly-sized spacers, screws, bone plates, and/or other hardware may be pre-operatively selected.

Thus, the result of the step 108 may provision, to the surgeon, of one or more of the following: (1) one or more patient-specific instruments; (2) one or more patient-specific implants; (3) an instrument, selected from one or more available instrument sizes and/or configurations; (4) an implant, selected from one or more available implant sizes and/or configurations; (5) instructions for which instrument(s) to select from available instrument sizes and/or configurations; (6) instructions for which implant(s) to select from available implant sizes and/or configurations; (7) instructions for proper positioning or anchorage of one or more instruments to be used in the procedure; and (8) instructions for proper positioning or anchorage of one or more implants to be used in the procedure. These items may be provided to the surgeon directly, or to a medical device company or representative, for subsequent delivery to the surgeon.

In a step 110, the manufactured instrumentation may be used in surgery to facilitate treatment of the condition. In some embodiments, this may include placing the modelled bone engagement surface against the corresponding contour of the bone used to obtain its shape, and then using the resection feature(s) to guide resection of one or more bones. Then the bone(s) may be further treated, for example, by attaching one or more joint replacement implants (in the case of joint arthroplasty), or by attaching bone segments together (in the case of arthrodesis or fracture repair). Prior to completion of the step 110, the instrumentation may be removed from the patient, and the surgical wound may be closed.

As mentioned previously, the method 100 may be used to correct a wide variety of bone conditions. One example of the method 100 will be shown and described in connection with FIG. 1B, for correction of a bunion deformity of the foot.

In certain embodiments, one or more of a method, apparatus, and/or system of the disclosed solution can be used for training a surgeon to perform a patient-specific procedure or technique. In one embodiment, the CAD model generated and/or patient-specific instrumentation, implants, and/or plan for conducting an operative procedure can be used to train a surgeon to perform a patient-specific procedure or technique.

In one example embodiment, a surgeon may submit a CT scan of a patient's foot to an apparatus or system that implements the disclosed solution. Next, a manual or automated process may be used to generate a CAD model and for making the measurements and correction desired for the patient. In the automated process, an advanced computer analysis system, machine learning and automated/artificial intelligence may be used to generate a CAD model and/or one or more patient-specific instruments and/or operation plans. For example, a patient-specific instrument may be fabricated that is registered to the patient's anatomy using a computer-aided machine (CAM) tool. In addition, a CAM tool may be used to fabricate a 3D structure representative of the patient's anatomy, referred to herein as a patient-specific synthetic cadaver. (e.g., one or more bones of a patient's foot). Next, the patient-specific instrument and the patient-specific synthetic cadaver can be provided to a surgeon who can then rehearse an operation procedure in part or in full before going into an operating room with the patient.

In certain embodiments, the patient-specific instrument or instrument can be used to preposition and/or facilitate pre-drilling holes for a plate system for fixation purposes. Such plate systems may be optimally placed, per a CT scan, after a correction procedure for optimal fixation outcome. In another embodiment, the CAD model and/or automated process such as advanced computer analysis, machine learning and automated/artificial intelligence may be used to measure a depth of through a patient-specific resection guide for use with robotics apparatus and/or systems which would control the depth of each cut within the guide to protect vital structures below or adjacent to a bone being cut. In another embodiment, the CAD model and/or automated process such as advanced computer analysis, machine learning and automated/artificial intelligence may be used to define desired fastener (e.g. bone screw) length and/or trajectories through a patient-specific instrument and/or implant. The details for such lengths, trajectories, and components can be detailed in a report provided to the surgeon preparing to perform a procedure.

FIG. 1B is a flowchart diagram depicting a method 120 for correcting or remediating a bone condition, according to one embodiment. The method 120 may be used to prepare for an orthopedic procedure which corrects or remediates a bone, muscle, deformity, and/or tendon condition of a patient.

As shown, the method 120 may begin with a step 122 in which a CT scan (or another three-dimensional image) of the patient's foot is obtained. The step 122 may include capturing a scan of select bones of a patient or may include capturing additional anatomic information, such as the entire foot. Additionally, or alternatively, the step 122 may include receipt of previously captured image data. Capture of the entire foot in the step 122 may facilitate proper alignment of the first metatarsal with the rest of the foot (for example, with the second metatarsal). Performance of the step 122 may result in generation of a three-dimensional model of the patient's foot, or three-dimensional surface points that can be used to construct such a three-dimensional model.

After the step 122 has been carried out, the method 120 may proceed to a step 124 in which a CAD model of the relevant portion of the patient's anatomy is generated. The CAD model may optionally include the bones of the entire foot, like the CT scan obtained in the step 122. In alternative embodiments, the step 124 may be omitted in favor of direct utilization of the CT scan data, as described in connection with the step 104.

In a step 126, the CAD model and/or CT scan data may be used to model patient-specific instrumentation that can be used to correct or remediate a bone condition. Such instrumentation may include a guide. In one example, the guide can seat or abut or contact a surface of a bone and including an opening that guides a trajectory for a fastener for a procedure. In some embodiments, performance of the step 126 may include modelling the guide with a bone engagement surface that is shaped to match contours of the surfaces of the bone, such that the bone engagement surface can lie directly on the corresponding contours of the bone.

In a step 128, the model(s) may be used to manufacture patient-specific instrumentation and/or instruments. This may include manufacturing an instrument with the bone engagement surface and/or other features as described above. As in the step 108, the step 128 may additionally or alternatively involve provision of one or more instruments and/or implants from among a plurality of predetermined configurations or sizes. Further, the step 128 may additionally, or alternatively, involve provision of instructions for placement and/or anchorage of one or more instruments and/or instruments to carry out the procedure.

In a step 130, the manufactured instrument may be used in surgery to facilitate treatment of the condition. In certain embodiments, a bone engagement surface of the instrument may be placed against the corresponding contours of the bone. The instrument may include an opening and/or trajectory guide to guide insertion of a trajectory guide such as a temporary fastener such as a K-wire. The instrument may then be removed, and the remaining steps of a surgical procedure performed.

Method 100 and method 120 are merely exemplary. Those of skill in the art will recognize that various steps of the method 100 and the method 120 may be reordered, omitted, and/or supplemented with additional steps not specifically shown or described herein.

As mentioned previously, the method 120 is one species of the method 100; the present disclosure encompasses many different procedures, performed with respect to many different bones and/or joints of the body. Exemplary steps and instrumentation for the method 120 will further be shown and described in connection with the present disclosure. Those of skill in the art will recognize that the method 120 may be used in connection with different instruments; likewise, the instruments of the present disclosure may be used in connection with methods different from the method 100 and the method 120.

FIG. 2A is a perspective dorsal view of a foot 200. The foot 200 may have a medial cuneiform 202, an intermediate cuneiform 204, lateral cuneiform 206, a first metatarsal 208, a second metatarsal 210, third metatarsal 212, fourth metatarsal 214, fifth metatarsal 216, navicular 218, cuboid 220, talus 222, and calcaneus 224, among others. The medial cuneiform 202 and the intermediate cuneiform 204 may be joined together at a first metatarsocuneiform joint, and the first metatarsal 208 and the second metatarsal 210 may be joined together at a second metatarsocuneiform joint. The foot 200 includes a set of proximal phalanges numbered first through fifth (230, 232, 234, 236, 238) and a set of distal phalanges numbered first through fifth (240, 242, 244, 246, 248) and a set of middle phalanges numbered second through fifth (250, 252, 254, 256).

FIG. 2B is a perspective lateral view of a foot 200, with bones of the foot labeled.

Figure 2C:
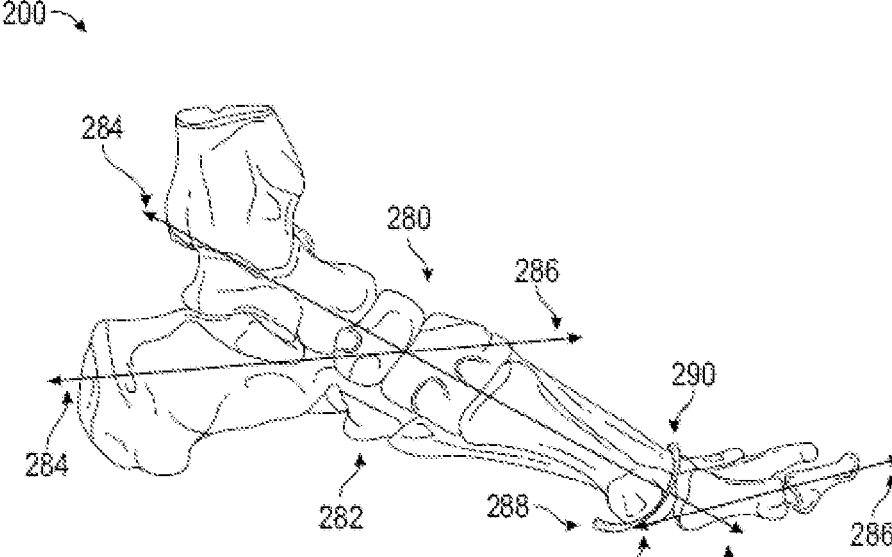
FIG. 2C is a lateral perspective view of bones of a foot.

FIG. 2C is a perspective medial view of a foot illustrating a dorsal side 280 and a plantar side 282. The foot 200, as illustrated, may have a tibia 226 and a fibula 228, among others. Dorsal refers to the top of the foot. Plantar refers to the bottom of the foot. Proximal 284 is defined as "closer to the primary attachment point". Distal 286 is defined as "further away from the attachment point". Plantarflex or plantarflexion 288 means movement toward the plantar side 282 of a foot or hand, toward the sole or palm. Dorsiflex or dorsiflexion 290 means movement toward the dorsal side 280 of a foot or hand, toward the top.

Figure 2D:
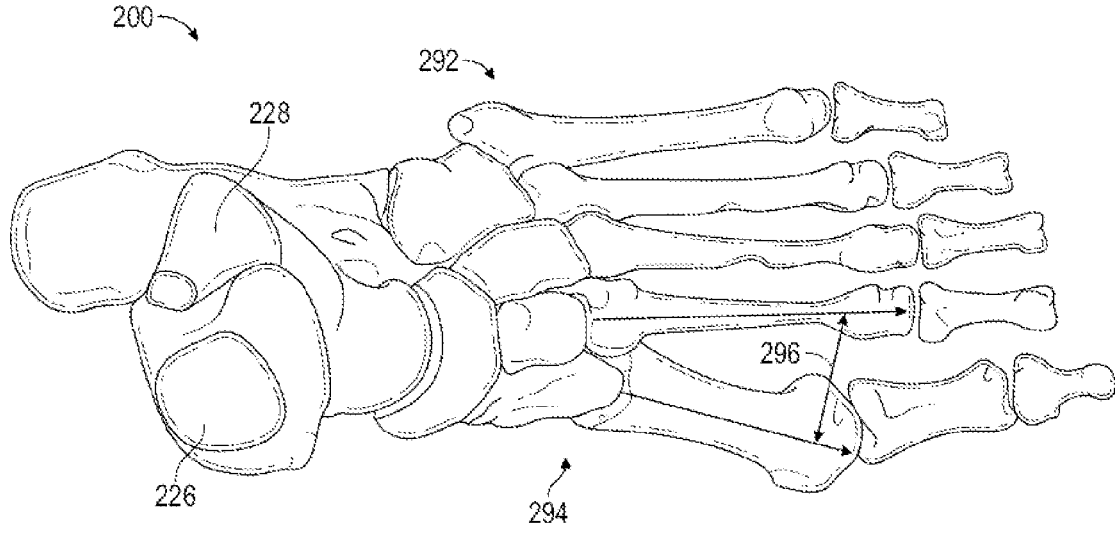
FIG. 2D is a dorsal perspective view of bones of a foot.

FIG. 2D is a perspective dorsal view of the foot 200. A transverse plane is the plane that shows the top of the foot. A lateral side 292 means a side furthest away from the midline of a body, or away from a plane of bilateral symmetry of the body. A medial side 294 means a side closest to the midline of a body, or toward a plane of bilateral symmetry of the body. For a Lapidus procedure, the inter-metatarsal (IM) angle 296 is the angle to be corrected to remove the hallux valgus (bunion) deformity.

Figure 2E:
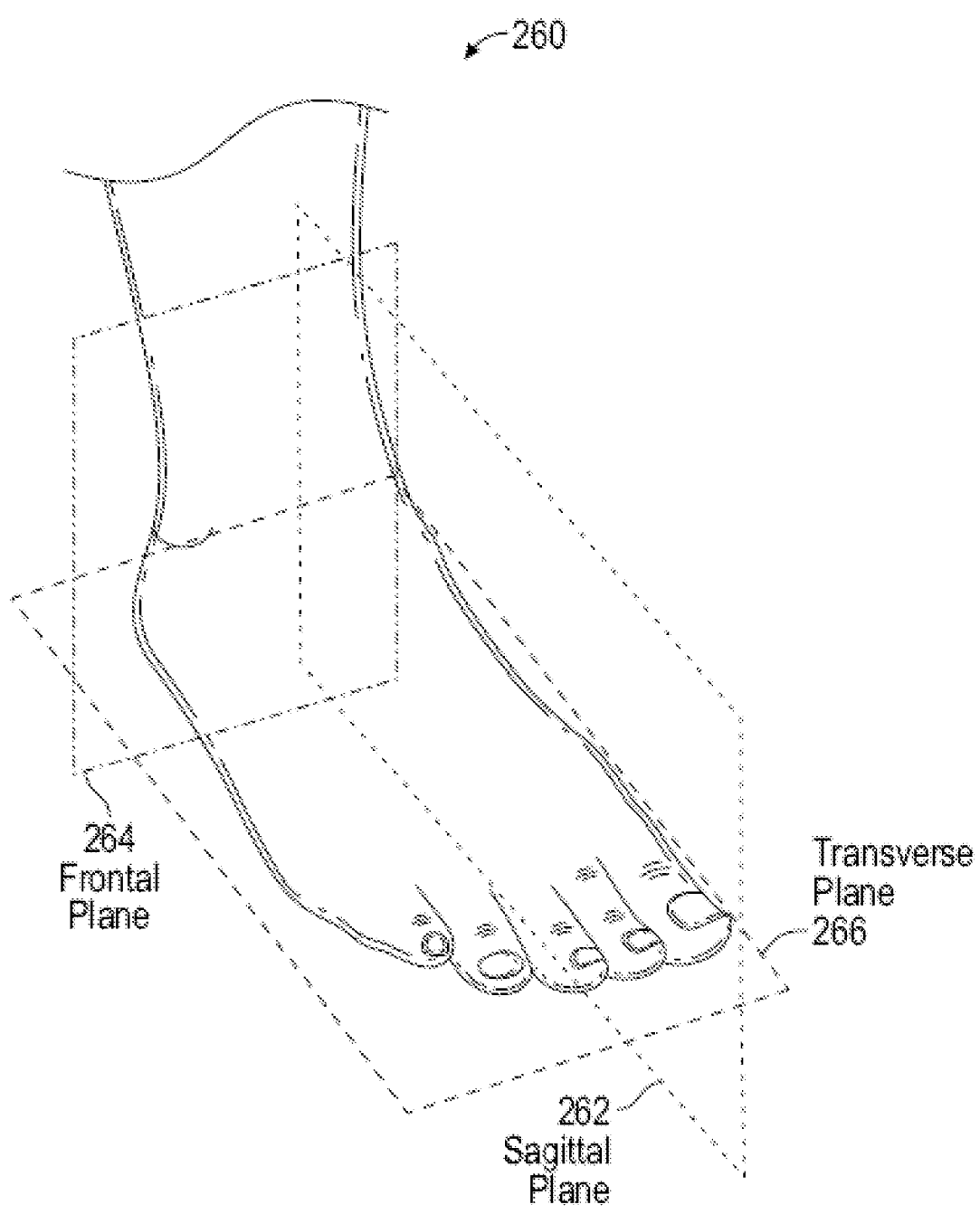
FIG. 2E is a view of a foot illustrating common planes of reference for a human foot.

FIG. 2E is a view of a foot illustrating common planes 260 of reference for a human foot. FIG. 2E illustrates a sagittal plane 262 that divides the foot into a right section and a left section half. The sagittal plane 262 is perpendicular to frontal or coronal plane 264 and the transverse plane 266. In the foot, the frontal plane 264 generally runs vertically through the ankle and the transverse plane 266 generally runs horizontally through the midfoot and toes of the foot.

Every patient and/or condition is different; accordingly, the degree of angular adjustment needed in each direction may be different for every patient. Use of a patient-specific instrument may help the surgeon obtain an optimal realignment, target, or position a bone tunnel, position one or more resections and/or fasteners and the like. Thus, providing patient-specific instruments, jigs, and/or instrumentation may provide unique benefits.

The present patient-specific instrumentation may be used to correct a wide variety of conditions. Such conditions include, but are not limited to, angular deformities of one bone in either the lower or upper extremities (for example, tibial deformities, calcaneal deformities, femoral deformities, and radial deformities). The present disclosure may also be used to treat an interface between two bones (for example, the ankle joint, metatarsal cuneiform joint, lisfranc's joint, complex Charcot deformity, wrist joint, knee joint, etc.). As one example, an angular deformity or segmental malalignment in the forefoot may be treated, such as is found at the metatarsal cuneiform level, the midfoot level such as the navicular cuneiform junction, hindfoot at the calcaneal cuboid or subtalar joint or at the ankle between the tibia and talar junction. Additionally, patient-specific instruments could be used in the proximal leg between two bone segments or in the upper extremity such as found at the wrist or metacarpal levels.

Figure 3:
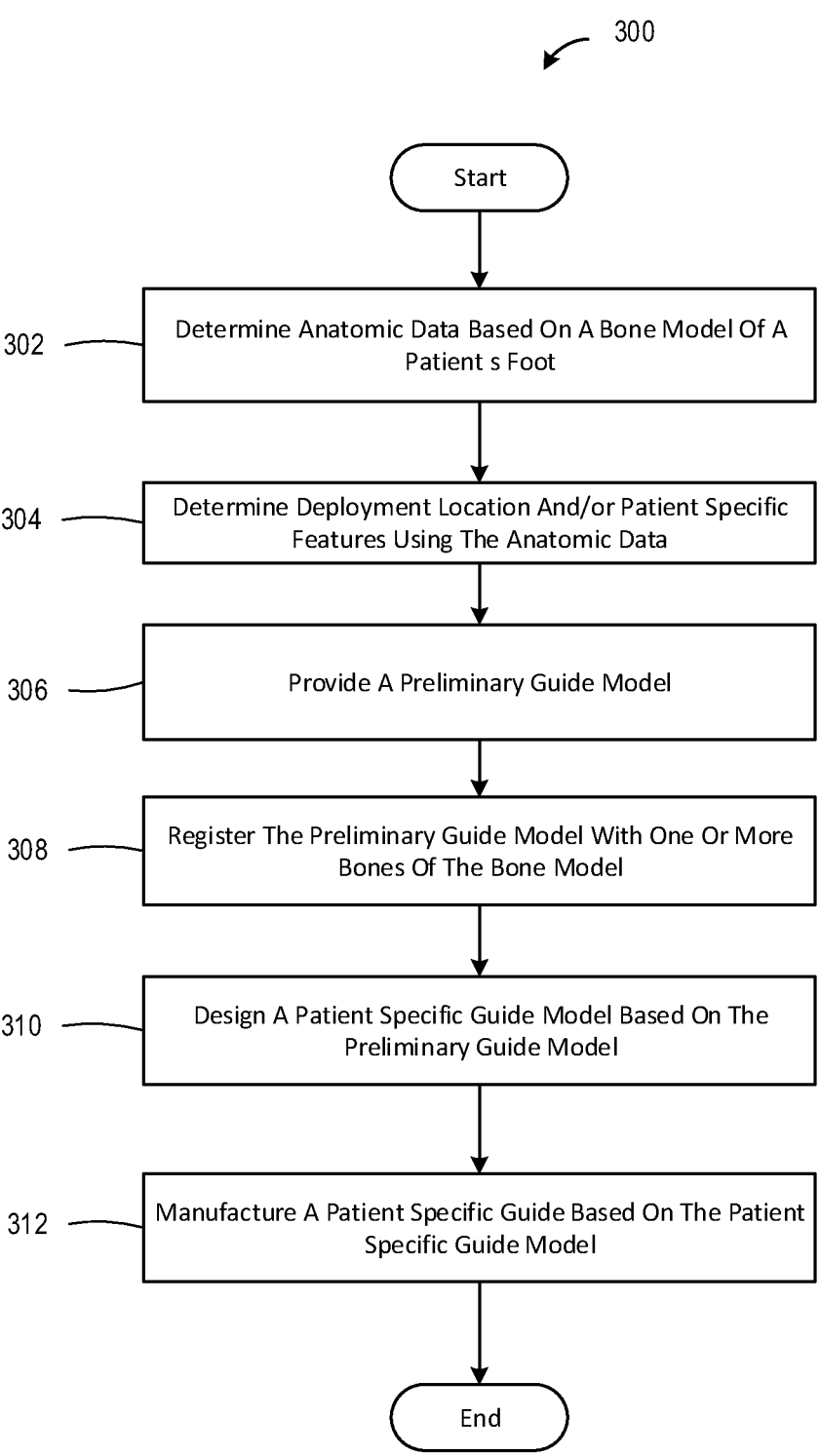
FIG. 3 is a flowchart diagram depicting a method for generating one or more patient-specific instruments configured to address a bone condition, according to one embodiment.

FIG. 3 illustrates a flowchart diagram depicting a method 300 for generating one or more patient-specific instruments configured to correct or address a bone or foot condition, according to one embodiment. Prior to steps of the method 300, a bone model (also referred to as CAD model above) is generated. The bone model may be generated using medical imaging of a patient's foot and may also be referred to as an anatomic model. The medical imaging image(s) may be used by computing devices to generate patient imaging data. The patient imaging data may be used to measure and account for orientation of one or more structures of a patient's anatomy. In certain embodiments, the patient imaging data may serve, or be a part of, anatomic data for a patient.

In one embodiment, the method 300 begins after a bone model of a patient's body or body part(s) is generated. In a first step 302, the method 300 may review the bone model and data associated with the bone model to determine anatomic data of a patient's foot.

After step 302, the method 300 may determine 304 a recommended location and/or a trajectory angle and/or patient-specific features for a procedure using the anatomic data. "Recommended location" refers to a location for deployment of guide or instrument on, in, between, or within one or more body parts (e.g., bones) of a patient. "Trajectory angle" refers to a recommended angle for deployment of an instrument, graft, body part, or resection feature angle relative to a bone of a patient for a procedure. In certain embodiments, determining the recommended location may employ advanced computer analysis system, expert systems, machine learning, and/or automated/artificial intelligence. In another embodiment, the method 300 may include determining one or more alternative locations and/or trajectory angles for tendon deployment.

Next, the method 300 may proceed and a preliminary guide model is provided 306 from a repository of template tendon trajectory models. A preliminary guide model is a model of a preliminary guide.

As used herein, "preliminary guide" refers to a guide configured, designed, and/or engineered to serve as a template, prototype, archetype, or starting point for creating, generating, or fabricating a patient-specific guide. In one aspect, the preliminary guide may be used, as-is, without any further changes, modifications, or adjustments and thus become a patient-specific guide. In another aspect, the preliminary guide may be modified, adjusted, or configured to more specifically address the goals, objectives, or needs of a patient or a surgeon and by way of the modifications become a patient-specific guide. The patient-specific guide can be used by a user, such as a surgeon, to guide steps in a surgical procedure, such as an osteotomy and/or a tendon transfer procedure. Accordingly, a preliminary guide model can be used to generate a patient-specific guide. The patient-specific guide model may be used in a surgical procedure to facilitate one or more steps of the procedure and may be used to generate a patient-specific guide that can be used in a surgical procedure for the patient.

In certain embodiments, the preliminary guide model may be generated based on anatomic data and/or a bone model or a combination of these, and no model or predesigned structure, template, or prototype. Alternatively, or in addition, the preliminary guide model may be, or may originate from, a template guide model selected from a set of template guide models. Each model in the set of template guide models may be configured to fit an average patient's foot. The template guide model may subsequently be modified or revised by an automated process or manual process to generate the preliminary guide model used in this disclosure.

As used herein, "template guide" refers to a guide configured, designed, and/or engineered to serve as a template for creating, generating, or fabricating a patient-specific guide. In one aspect, the template guide may be used, as-is, without any further changes, modifications, or adjustments and thus become a patient-specific guide. In another aspect, the template guide may be modified, adjusted, or configured to more specifically address the goals, objectives, or needs of a patient or a surgeon and by way of the modifications become a patient-specific guide. The patient-specific guide can be used by a user, such as a surgeon, to guide making one or more resections of a structure, such as a bone for a procedure. Accordingly, a template guide model can be used to generate a patient-specific guide model. The patient-specific guide model may be used in a surgical procedure to address, correct, or mitigate effects of the identified deformity and may be used to generate a patient-specific guide that can be used in a surgical procedure for the patient.

Next, the method 300 may register 308 the preliminary guide model with one or more bones of the bone model. This step 308 facilitates customization and modification of the preliminary guide model to generate a patient-specific guide model from which a patient-specific guide can be generated. The registration step 308 may combine two models and/or patient imaging data and positions both models for use in one system and/or in one model.

Next, the method 300 may design 310 a patient-specific guide model based on the preliminary guide model. The design step 310 may be completely automated or may optionally permit a user to make changes to a preliminary guide model or partially completed patient-specific guide model before the patient-specific guide model is complete. A preliminary guide model and patient-specific guide model are two examples of an instrument model. As used herein, "instrument model" refers to a model, either physical or digital, that represents an instrument, tool, apparatus, or device. Examples of an instrument model can include a cutting guide model, a resection guide model, an alignment guide model, a reduction guide model, a patient-specific tendon trajectory guide model, and the like. In one embodiment, a patient-specific guide and a patient-specific guide model may be unique to a particular patient and that patient's anatomy and/or condition.

The method 300 may conclude by a step 312 in which patient-specific guide may be manufactured based on the patient-specific guide model. Various manufacturing tools, devices, systems, and/or techniques can be used to manufacture the patient-specific guide.

Figure 4:
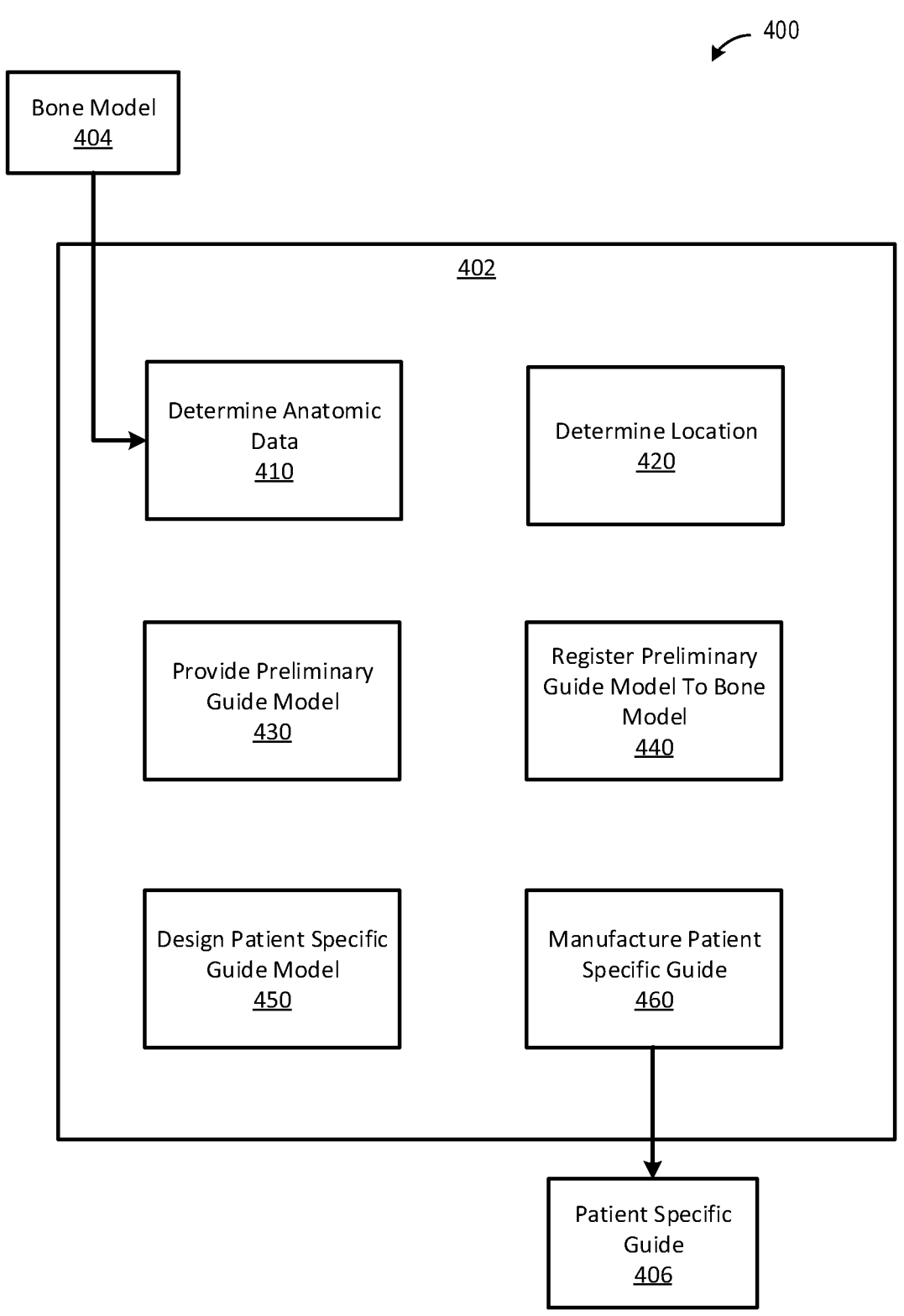
FIG. 4 illustrates an exemplary system configured to generate one or more patient-specific instruments configured to address a bone condition, according to one embodiment.

FIG. 4 illustrates an exemplary system 400 configured to generate one or more patient-specific instruments configured to facilitate surgical procedures, according to one embodiment. The system 400 may include an apparatus 402 configured to accept, review, receive or reference a bone model 404 and provide a patient-specific guide 406. In one embodiment, the apparatus 402 is a computing device. In another embodiment, the apparatus 402 may be a combination of computing devices and/or software components or a single software component such as a software application.

The apparatus 402 may include a determination module 410, a location module 420, a provision module 430, a registration module 440, a design module 450, and a manufacturing module 460. Each of which may be implemented in one or more of software, hardware, or a combination of hardware and software.

The determination module 410 determines anatomic data 412 from a bone model 404. In certain embodiments, the system 400 may not include a determination module 410 if the anatomic data is available directly from the bone model 404. In certain embodiments, the anatomic data for a bone model 404 may include data that identifies each anatomic structure within the bone model 404 and attributes about the anatomic structure. For example, the anatomic data may include measurements of the length, width, height, and density of each bone in the bone model. Furthermore, the anatomic data may include position information that identifies where each structure, such as a bone is in the bone model 404 relative to other structures, including bones. The anatomic data may be in any suitable format and may be stored separately or together with data that defines the bone model 404.

In one embodiment, the determination module 410 may use advanced computer analysis system such as image segmentation to determine the anatomic data. The determination module 410 may determine anatomic data from one or more sources of medical imaging data, images, files, or the like. Alternatively, or in addition the determination module 410 may use software and/or systems that implement one or more artificial intelligence methods (e.g., machine learning and/or neural networks) for deriving, determining, or extrapolating, anatomic data from medical imaging or the bone model. In one embodiment, the determination module 410 may perform an anatomic mapping of the bone model 404 to determine each unique aspect of the intended osteotomy procedure and/or bone resection and/or bone translation. The anatomic mapping may be used to determine coordinates to be used for an osteotomy procedure, position and manner of resections to be performed either manually or automatically or using robotic surgical assistance, a width for bone cuts, an angle for bone cuts, a predetermined depth for bone cuts, dimensions and configurations for resection instruments such as saw blades, milling bit size and/or speed, saw blade depth markers, and/or instructions for automatic or robotic resection operations.

In one embodiment, the determination module 410 may use advanced computer analysis system such as image segmentation to determine the anatomic data. The determination module 410 may determine anatomic data from one or more sources of medical imaging data, images, files, or the like. The determination module 410 may perform the image segmentation using 3D modeling systems and/or artificial intelligence (AI) segmentation tools. In certain embodiments, the determination module 410 is configured to identify and classify portions of bone based on a condition of the bone, based on the bone condition. Such classifications may include identifying bone stability, bone density, bone structure, bone deformity, bone structure, bone structure integrity, and the like. Accordingly, the determination module 410 may identify portions or sections or one or more bones based on a quality metric for the bone. Advantageously, that determination module 410 can identify high quality bone having a viable structure, integrity, and/or density versus lower quality bone having a nonviable structure, integrity, and/or density and a plurality of bone quality levels in between.

Accordingly, the determination module 410 can guide a surgeon to determine which areas of one or more bones of a patient are within a "soft tissue envelope" (bone of undesirable quality) as that bone relates to a particular deformity or pathology. Identifying the quality of one or more bones of the patient can aid a surgeon in determining what type of correction or adjustment is needed. For example, an ulceration that occurs due to a boney deformity can be mapped using the determination module 410 in a way that a correction can be performed to correct the deformity and reduce pressure to an area and address the structures that were causing the pressure ulceration/skin breakdown.

In addition, the determination module 410 and/or another component of the apparatus 402 can be used to perform anatomic mapping which may include advanced medical imaging, such as the use of CT scan, ultrasound, MRI, and bone density scans can be combined to effectively create an anatomic map that determines the structural integrity of the underlying bone.

Identifying the structural integrity of the underlying bone can help in determining where bone resections can be performed to preserve the densest bone in relation to conditions such as Charcot neuropathic, arthropathy where lesser dense bone can fail and collapse. It is well documented in the literature that failure to address and remove such lesser dense bone can ultimately lead to failure of a reconstruction and associated hardware.

The present disclosure provides, by way of at least the exemplary system 400, an anatomic map that can be part of anatomic data. The anatomic map can combine structural, deformity, and bone density information and can be utilized to determine the effective density of bone and help to determine where bone should be resected in order to remove the lesser dense bone while maintaining more viable bone to aid in the planning of the osteotomy/bone resection placement.

The location module 420 determines or identifies one or more recommended locations and/or trajectory angles for deployment of an instrument, graft, and/or soft tissue based on the anatomic data 412 and/or the bone model 404. In one embodiment, the location module 420 may compare the anatomic data 412 to a general model that is representative of most patient's anatomies and may be free from deformities or anomalies. The location module 420 can operate autonomously and/or may facilitate input and/or revisions from a user. The location module 420 may be completely automated, partially automated, or completely manual. A user may control how automated or manual the determining of the location and/or trajectory angles is.

The provision module 430 is configured to provide a preliminary guide model 438. The provision module 430 may use a variety of methods to provide the preliminary guide model. In one embodiment, the provision module 430 may generate a preliminary guide model. In the same, or an alternative embodiment, the provision module 430 may select a template guide model for a tendon (or tendon substitute) deployment procedure configured to enable locating the position and/or providing the trajectory provided by the location module 420. In one embodiment, the provision module 430 may select a template guide model from a set of template guide models (e.g., a library, set, or repository of template guide models).

The registration module 440 registers the preliminary guide model with one or more bones or other anatomical structures of the bone model 404. As explained above, registration is a process of combining medical imaging data, patient imaging data, and/or one or more models such that the preliminary guide model can be used with the bone model 404.

The design module 450 designs a patient-specific guide (or patient-specific guide model) based on the preliminary guide model. The design operation of the design module 450 may be completely automated, partially automated, or completely manual. A user may control how automated or manual the designing of the patient-specific guide (or patient-specific guide model) is.

The manufacturing module 460 may manufacture a patient-specific guide 406 using the preliminary guide model. The manufacturing module 460 may use a patient-specific guide model generated from the preliminary guide model. The manufacturing module 460 may provide the patient-specific guide model to one or more manufacturing tools and/or fabrication tool. The patient-specific guide model may be sent to the tools in any format such as an STL file or any other CAD modeling or CAM file or method for data exchange. In one embodiment, a user can adjust default parameters for the patient-specific guide such as types and/or thicknesses of materials, dimensions, and the like before the manufacturing module 460 provides the patient-specific guide model to a manufacturing tool.

Effective connection of the guide to one or more bones can ensure that surgical steps are performed in desired locations and/or with desired orientations and mitigate undesired surgical outcomes.

Figure 5:
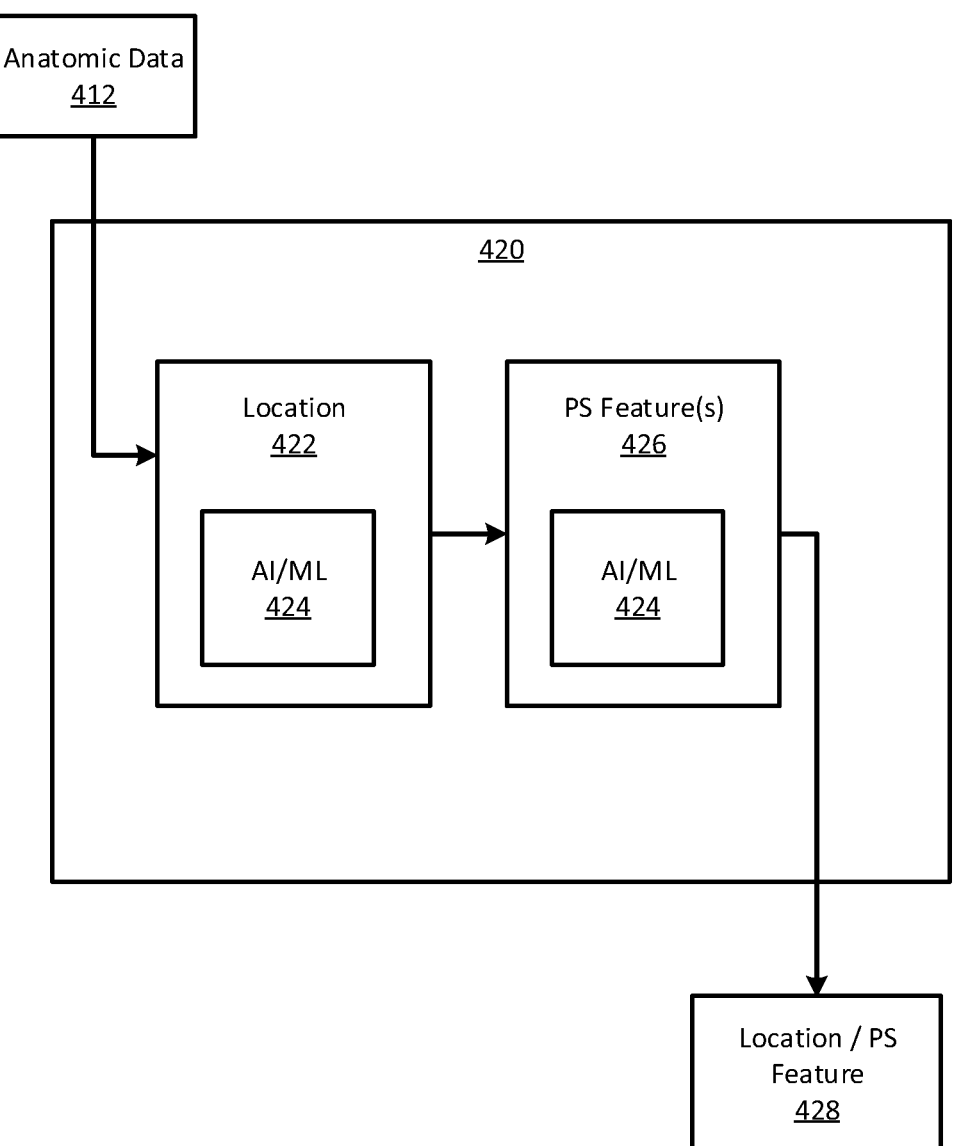
FIG. 5 illustrates an exemplary apparatus configured to determine a location and/or a trajectory, according to one embodiment.

FIG. 5 illustrates an exemplary location module 420 configured to determine a location and/or trajectory for tendon deployment, according to one embodiment. The location module 420 may factor in one or more landmarks on one or more surfaces of one or more bones of a patient of the bone model 404. The location module 420 may be completely automated, partially automated, or completely manual. A user may control how automated or manual the determination of the location is. The user may provide instructions to the location module 420 to facilitate automatic or partially automated determination of one or more locations.

The location module 420 may include a location module 422. The location module 422 may be configured for automated determination of a location for tendon or tendon substitute deployment. For example, in one embodiment, the location module 422 includes an artificial intelligence or machine learning module 424. The artificial intelligence or machine learning module 424 is configured to implement one or more of a variety of artificial intelligence modules that may be trained for identifying bones in the bone model 404, determining surfaces and/or sides of one or more bones, determining landmarks (both natural and/or abnormalities), determining axes of a bone, such as a longitudinal axis and/or a horizontal axis of a bone based on anatomic data 412 and/or a bone model 404. In another embodiment, the location module 420 may receive patient imaging data, a bone model, a CAD model or the like and use these inputs to determine a location and/or trajectory in relation to one or more bones of a patient.

In one embodiment, the artificial intelligence or machine learning module 424 may be trained using a large data set of anatomic data 412 for healthy bones and a large data set of anatomic data 412 for bones with abnormalities and/or landmarks in which the abnormalities and/or landmarks have been previously identified and labeled in the dataset. The artificial intelligence or machine learning module 424 may implement, or use, a neural network configured according to the training such that as the artificial intelligence or machine learning module 424 accepts the anatomic data 412 for a particular patient, the artificial intelligence or machine learning module 424 is able to determine what one or more locations (e.g., a recommended location and one or more alternative locations for the guide.

The location module 422 may interact with a patient specific feature module 426. The patient specific feature module 426 may take one or more locations provided by the location module 422 and the bone model 404 and/or anatomic data 412 and determine suitable patient specific features. In certain embodiments, the patient specific features provided by the patient specific feature module 426 may include a number of resection features, an angle or trajectory for one or more resection features, a number, size, and/or position of bone attachment features, a number, size, or position of alignment guides or a combination of these. In certain embodiments, the patient specific feature module 426 may focus on resection features.

As with the location module 420, the patient specific feature module 426 may be completely automated, partially automated, or completely manual. A user may control how automated or manual the determination of the trajectory is. The user may provide instructions to the patient specific feature module 426 to facilitate automatic or partially automated determination of one or more trajectories. In one embodiment, the location module 422 includes an artificial intelligence or machine learning module 424 that facilitates determining one or more trajectories.

The location module 420 outputs a location/patient specific feature 428 for an orthopedic surgical procedure.

Figure 6:
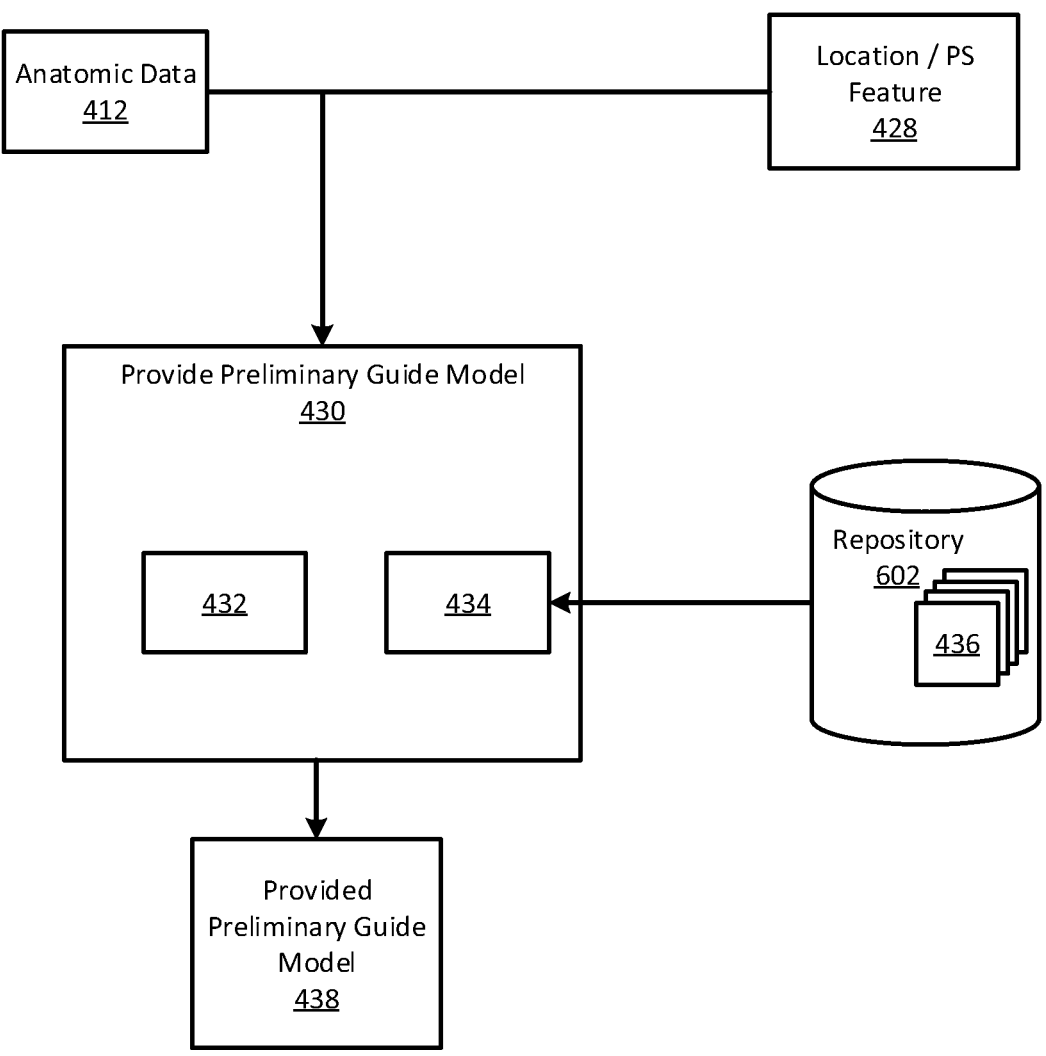
FIG. 6 illustrates an exemplary provision module configured to provide a preliminary guide model, according to one embodiment.

FIG. 6 illustrates an exemplary provision module 430 configured to provide a preliminary guide model, according to one embodiment. The provision module 430 may accept anatomic data 412 and a location/patient specific feature 428. In the illustrated embodiment, the provision module 430 may generate a preliminary guide model 438 (e.g., generate from 'scratch') or the provision module 430 may select a template guide model 436 automatically from a set of template guide models 436 stored in a repository 602. The provision module 430 may incorporate a variety of parameters in order to provision, generate, determine, or select a template guide model 436. For example, in addition to the anatomic data 412, the provision module 430 may include patient imaging data, deformity parameters for a variety of angular deformities (in all 3 planes) of the midfoot or hind foot and ankle where tendon deployment procedure could be used, patient preferences, and/or surgeon input parameters.

In one embodiment, the provision module 430 may include a generator 432 and/or a selection module 434. In one embodiment, the generator 432 is configured to generate a preliminary guide model 438. In certain embodiments, the generator 432 may generate or create the preliminary guide model based on anatomic data and/or a bone model or a combination of these and no other inputs. (e.g. no model or predesigned structure, template, or prototype). Alternatively, or in addition, the generator 432 may generate or create the preliminary guide model using a standard set of features or components that can be combined to form the preliminary guide model. The generated preliminary guide model may subsequently be modified or revised by an automated process, and/or manual process, to generate the preliminary guide model used in this disclosure.

The selection module 434 may be configured to select a template guide model 436 for an osteotomy procedure configured to correct the deformity identified by the location module 420. In one embodiment, the provision module 430 may select a template guide model 436 from a set of template guide models 436 (e.g., a library, set, or repository of template guide models 436). In one embodiment, the template guide model 436 may include digital models. In another embodiment, the template guide model 436 may include physical models. In such an embodiment, the repository 602 may be a warehouse or other inventory repository. Where the template guide model 436 are physical models, the systems, modules, and methods of this disclosure can be used and the physical model may be milled or machined (e.g., a CNC machine) to form a patient-specific guide that conforms to the bone surfaces of the patient.

Selection of a suitable template guide model 436 may be completely automated and/or may be partially automated and/or may depend on confirmation from a user before a generated preliminary guide model or a proposed template guide model 436 becomes the preliminary guide model 438. In another embodiment, the selection module 434 may facilitate a manual selection by a user of a template guide model 436 that would become the preliminary guide model 438. The selection module 434 may use the anatomic data 412 or the bone model 404 or a combination of these to select a suitable template guide model that would become the preliminary guide model 438.

In another embodiment, the generator 432 may facilitate revisions or edits by a user of a generated guide model that will become the preliminary guide model 438. The selection module 434 may use the anatomic data 412 or the bone model 404 or a combination of these to select a suitable template guide model that would become the preliminary guide model 438.

The repository 602 may include any number of, and/or a variety of template guide models 436. The template guide models 436 may be distinguished based on a gender or age of the patient, which joint of a midfoot, hind foot, or ankle will be cut, which material will be used for the template guide, and the like. The template guide model 436 may differ from each other in what degree of deformity correction the template guide model 436 is designed to provide. In addition, the template guide models 436 may be distinguished based on how one or more features of the template guide model 436 are positioned, arranged, and/or configured relative to each other. For example, in certain template guide models 436, the number, position, and/or configuration of alignment features and/or bone attachment features (e.g., holes) may vary based on needs or preferences of patients, the nature of the deformity, and/or surgeon preferences.

In certain embodiments, the template guide models 436 may vary in how the slots (e.g., resection features) for the cuts are positioned, angled, and oriented relative to each other and/or to a longitudinal axis of respective bones at a joint for use with the template guide model 436. For example, in one template guide model 436 the slot 1352 for a resection of a metatarsal bone may be perpendicular to a longitudinal axis of the metatarsal bone and the slot 1350 may be angled relative to a longitudinal axis of the cuneiform or cuboid bone such that once the two bones are brought together the deformity is corrected. Alternatively, in another template guide model 436 the slot for a resection of a metatarsal bone may be angled relative to a longitudinal axis of the metatarsal bone and the slot 1350 may be perpendicular to a longitudinal axis of the cuneiform or cuboid bone such that once the two bones are brought together the deformity is corrected.

The selection module 434 may be configured to automatically select a template guide model 436 and/or provide an automatic template guide model 436 recommendation that can be changed by a user, such as a surgeon. For example, in one embodiment, the provision module 430 and/or selection module 434 includes an artificial intelligence or machine learning module. The artificial intelligence or machine learning module is configured to implement one or more of a variety of artificial intelligence modules that may be trained for selecting a template guide model 436 based on anatomic data 412 and/or other input parameters. In one embodiment, the artificial intelligence or machine learning module may be trained using a large data set of anatomic data 412 for suitable template guide models 436 identified and labeled in the dataset by professionals for use to treat a particular deformity. The artificial intelligence or machine learning module may implement, or use, a neural network configured according to the training such that the artificial intelligence or machine learning module is able to select a suitable template guide model 436. The template guide model 436 selected by the selection module 434 can become the preliminary guide model 438.

Figure 7:
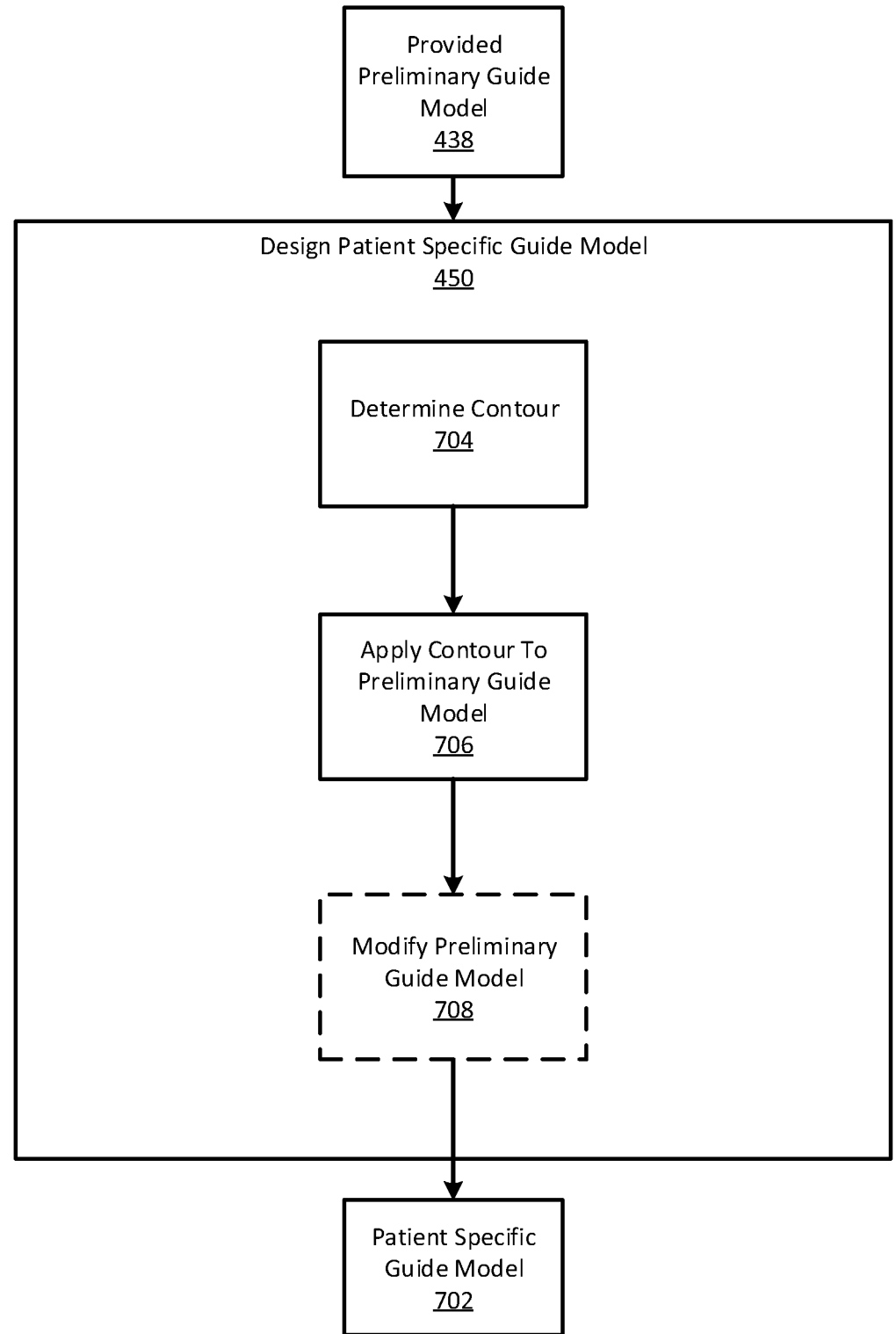
FIG. 7 illustrates an exemplary design module configured to design a patient-specific guide model, according to one embodiment.

FIG. 7 illustrates an exemplary design module 450 configured to design a patient-specific guide model, according to one embodiment. The design module 450 may accept a preliminary guide model 438 and generate a patient-specific guide model 702. In one embodiment, the design module 450 includes a contour module 704, an application module 706, and/or an optional modification module 708.

Referring now to FIG. 7, the design module 450 may modify the preliminary guide model 438 such that the bone-facing and/or bone-contacting surfaces of the preliminary guide model 438 match a contour of the surfaces and/or joint of one or more bones where a step of an orthopedic procedure will be performed using the preliminary guide model 438.

The contour module 704 may determine a contour of the bones that will contact the preliminary guide model 438. The contour module 704 may use a bone model 404 and/or anatomic data 412 to determine the contour. For example, the contour module 704 may determine the shape of a dorsal surface of a calcaneus 222.

The application module 706 may apply the contour to the provided preliminary guide model 438 to custom contour a bone engagement surface of the preliminary guide model 438 to match the shape, contour, and/or one or more landmarks of a bone, such as a dorsal surface of a calcaneus 222. Applying the contour to the preliminary guide model 438 may convert the preliminary guide model 438 to a patient-specific guide model 702.

Generation of the contours of bone engagement surface of the preliminary guide model 438 may be performed in various CAD programs. In some embodiments, the shapes of the corresponding surface dorsal surface of a calcaneus 222 may be obtained directly from the bone model 404, anatomic data 412, CAD models and/or CT scan data, and simply copied onto the preliminary guide model 438. Various operations may be used to copy surfaces from one object to another. Additionally or alternatively, various Boolean operations, such as a Boolean subtraction operation, may be used to remove material from a model for the body of the preliminary guide model 438 with a shape that matches the dorsal surface of a calcaneus 222.

In certain embodiments, the design module 450 may include an optional module, such as a modification module 708. The modification module 708 may enable a user such as a technician or surgeon to make additional modifications to the design and configuration of the preliminary guide model 438. In one embodiment, the user can change any of the features, trajectories, fixation holes, handle engagement holes, angles, configurations, or parameters of the preliminary guide model 438. For example, a surgeon may be aware of other concerns or anatomic aspects of a patient, for example on an opposite foot or in connection with a hip or other orthopedic joint which motivate the surgeon to adjust an angle of one of more trajectories of the preliminary guide model 438.

Alternatively, or in addition, a user may use the modification module 708 to modify a predefined tendon deployment procedure. The user may add, remove, or modify steps and the instrumentation used in the tendon deployment procedure to create a patient-specific tendon deployment procedure. In this manner, a user may configure features of a preliminary guide model 438 or modified preliminary guide model and/or tendon deployment procedure specific to a patient-specific osteotomy procedure the surgeon is planning for the patient.

The user may review the preliminary guide model 438 and make adjustments or revisions or make no adjustments or revisions. The output of the modification module 708 and/or the application module 706 is a patient-specific guide model 702.

Figure 8:
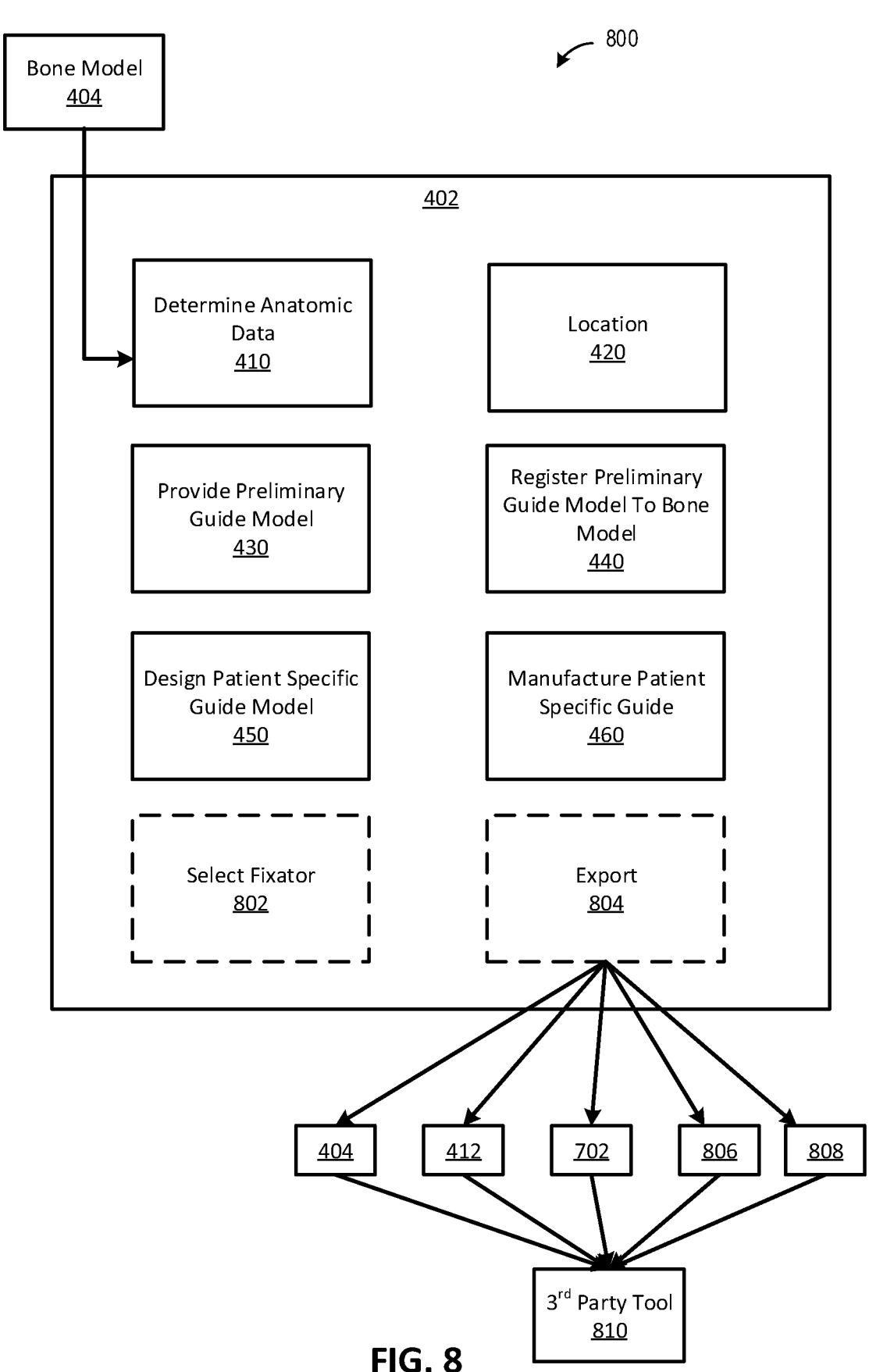
FIG. 8 illustrates an exemplary system configured to generate one or more patient-specific instruments configured to address a bone condition, according to one embodiment.

FIG. 8 illustrates an exemplary system 800 configured to generate one or more patient-specific instruments configured to correct a bone condition, according to one embodiment. The system 800 may include similar components or modules to those described in relation to FIG. 4. In addition, the system 800 may include a fixator selector 802 and/or an export module 804.

The fixator selector 802 enables a user to determine which fixator(s) to use for a tendon deployment procedure planned for a patient. In one embodiment, the fixator selector 802 may recommend one or more fixators based on the bone model 404, the location, the trajectory, or input from a user or a history of prior tendon deployment procedures performed. The fixator selector 802 may select a fixator model from a set of predefined fixator models or select a physical fixator from a set of fixators. The fixators may include a plate and associated accessories such as screws, anchors, and the like.

In one embodiment, the fixator selector 802 includes an artificial intelligence or machine learning module. The artificial intelligence or machine learning module is configured to implement one or more of a variety of artificial intelligence modules that may be trained for selecting fixator(s) based on anatomic data 412 and/or other input parameters. In one embodiment, the artificial intelligence or machine learning module may be trained using a large data set of anatomic data 412 for suitable fixator(s) identified and labeled in the dataset by professionals for use to treat a particular condition. The artificial intelligence or machine learning module may implement, or use, a neural network configured according to the training such that the artificial intelligence or machine learning module is able to select or recommend suitable fixator(s).

The export module 804 is configured to enable exporting of a patient-specific guide model 702 for a variety of purposes including, but not limited to, fabrication/manufacture of a patient-specific guide 406 and/or fixator(s), generation of a preoperative plan, generation of a physical bone model matching the bone model 404, and the like. In one embodiment, the export module 804 is configured to export the bone model 404, anatomic data 412, a patient-specific guide model 702, a preoperative plan 806, a fixator model 808, or the like. In this manner the custom instrumentation and/or procedural steps for a tendon deployment procedure can be used in other tools. The preoperative plan 806 may include a set of step by step instructions or recommendation for a surgeon or other staff in performing a tendon deployment procedure such as patient-specific tendon deployment procedure. The preoperative plan 806 may include images and text instructions and may include identification of instrumentation to be used for different steps of the tendon deployment procedure. The instrumentation may include the patient-specific guide 406 and/or one or more fixators. In one embodiment, the export module 804 may provide a fixator model which can be used to fabricate a fixator for the tendon deployment procedure.

The exports (404, 412, 702, 806, and 808) may be inputs for a variety of 3rd party tools 810 including a manufacturing tool, a simulation tool, a virtual reality tool, an augmented reality tool, an operative procedure simulation tool, a robotic assistance tool, and the like. A surgeon can then use these tools when performing a tendon deployment procedure or for rehearsals and preparation for the tendon deployment procedure. For example, a physical model of the bones, patient-specific guide 406, and/or fixators can be fabricated, and these can be used for a rehearsal operative procedure. Alternatively, a surgeon can use the bone model 404, preliminary guide model 438, and/or a fixator model to perform a simulated tendon deployment procedure using an operative procedure simulation tool.

Figure 9:
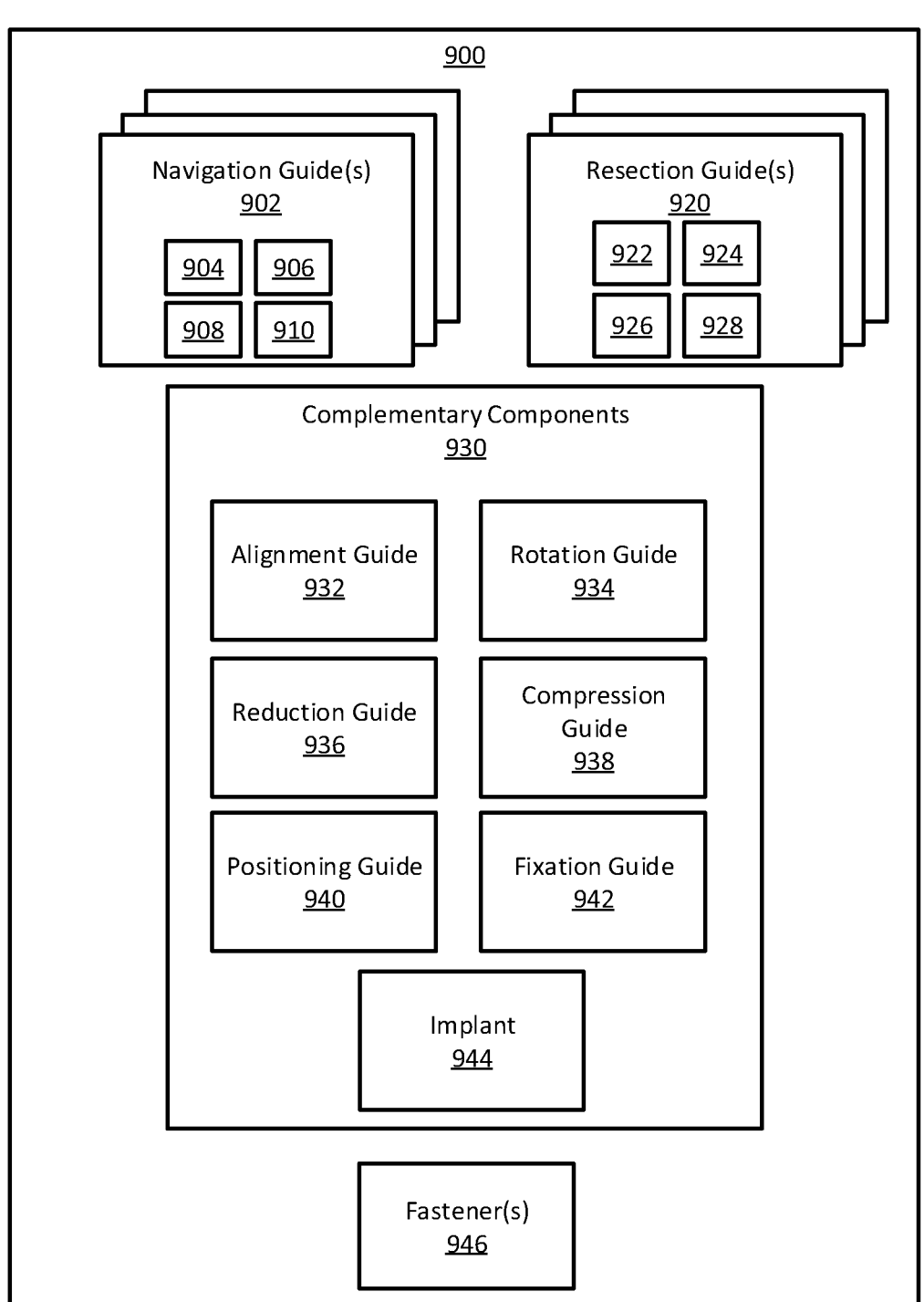
FIG. 9 illustrates an exemplary system, according to one embodiment.

FIG. 9 illustrates an exemplary system 900, according to one embodiment. The system 900 can include one or more navigation guides 902, one or more resection guides 920, one or more complementary components 930, and one or more fasteners 946. While a system 900 can be used for a variety of procedures, one or more features, components, and/or aspects of the system 900 may be particularly suited for one or more osteotomies on one or more bones of a patient's anatomy such as a patient's foot, ankle, wrist, hand, shoulder, or the like.

A navigation guide 902 can serve to guide a surgeon during one or more stages of a surgical procedure. In one embodiment, the navigation guide 902 can provide a guide or a template for a surgeon for where to form, provide, position, and/or orient one or more reference features. "Reference feature" refers to a feature configured for use as a point, plane, axis, or line of reference (aka a reference). A reference or reference feature can be used to position, measure, orient, fixate, couple, engage, and/or align one object or structure with another object or structure. In certain embodiments, a reference or reference feature can serve as a baseline, a ground truth, a waypoint, a control point, a landmark, and/or the like. A reference feature can facilitate moving from one coordinate system or frame of reference in a virtual environment to a position, location, frame of reference, environment, or orientation on, or in, an actual object, structure, device, apparatus, anatomical structure, or the like. Advantageously, a reference feature can coordinate objects, models, or structures in a digital or virtual model or representation with corresponding objects or structures (e.g., anatomical structures) of actual physical objects or structures. Said another way, a reference feature can serve to map from a virtual or modeled object to an actual or physical object.

As used herein, "feature" refers to a distinctive attribute or aspect of something. (Search "feature" on google.com. Oxford Languages, 2021. Web. 20 Apr. 2021.) A feature may include one or more apparatuses, structures, objects, systems, sub-systems, devices, or the like. A feature may include a modifier that identifies a particular function or operation and/or a particular structure relating to the feature. Examples of such modifiers applied to a feature, include, but are not limited to, "attachment feature," "bone attachment feature," "securing feature," "placement feature," "protruding feature," "engagement feature," "disengagement feature," "resection feature", "guide feature", "alignment feature", and the like. Thus, a guide feature may be a structure that facilitates and/or enables guiding an instrument or stage. A resection feature may be a structure that facilitates and/or enables resection.

In the present disclosure, a reference feature(s) can provide a preoperative feature or intraoperative feature that can enable a surgeon to model patient anatomy, model instrumentation, model implants, and/or practice a surgical procedure either virtually or using physical models, and then during the surgery configure, position, orient and/or register instrumentation, implants, and/or other surgical components to perform the surgery using the registered instrumentation, implants, and/or other surgical components developed, designed, and/or refined in a virtual or simulated procedure. In one example embodiment, a reference feature can be realized by a hole, tunnel, or other opening, in a bone or other hard tissue and/or in soft tissue. In another example embodiment, a reference feature can be realized by a hole, tunnel, or other opening, in a bone or other hard tissue and/or in soft tissue together with another structure such as a fastener such as a bone screw, a K-wire, or the like.

"Reference feature guide" refers to a guide that serves to aid in forming and/or deploying one or more reference features. Examples of reference feature guides include but are not limited to a hole, a round hole, a channel, a slot, a plurality of holes, a fence, a backstop, a guard, a fastener, a pilot hole, a blind hole, a chute, a ramp, or the like.

Advantageously, the navigation guide 902 facilitates providing, forming, establishing, and/or configuring one or more reference features for a surgical procedure. The navigation guide 902 can include a body 904, an opening 906, and one or more position indicators 908. In certain embodiments, a navigation guide 902 may include a bone attachment feature 910. In such embodiments, the bone attachment feature 910 can be used to secure the navigation guide 902 to a bone or bone fragment, at least temporarily.

The one or more resection guides 920 assist a surgeon in performing one or more different resection steps for an osteotomy procedure. In certain embodiments, a resection guide 920 includes one or more resection features 922 and one or more bone attachment features 924. The resection features 922 can take a variety of forms and/or embodiments. Similarly, the bone attachment features 924 can take a variety of forms and/or embodiments. The bone attachment features 924 may be similar to, the same as, or different from, the bone attachment feature 910 that can be used with the navigation guide 902. The resection features 922 provide a guide for a surgeon using a cutting tool to resect a bone, one or more bones, or other tissues of a patient. The bone attachment features 924 serve to secure the resection guide 920 to one or more bones, one or more bone fragments, and/or one or more other structures. In one example, a bone attachment feature 924 can include a hole in the resection guide 920 together with a temporary fastener such as a K-wire or pin.

The bone attachment features 924 can be used to engage or connect or attach a resection guide 920 to one or more bones, or bone fragments, of a patient. The bone attachment features 924 may include any of a wide variety of fasteners including, but not limited to, holes, prongs, spikes, fastening devices, and/or the like. Effective engagement or connection of the resection guide 920 to one or more bones along a single bone, across a single joint, across a plurality of joints, or the like, can ensure that cut surfaces are formed in desired locations and orientations and mitigate removal of hard tissue and/or soft tissue in undesired locations.

In certain embodiments, a resection guide 920 may include one or more bone engagement surfaces 926 and/or one or more landmark registration features 928. In certain embodiments, a landmark registration feature 928 may extend from one or more sides of the resection guide 920 and engage with one or more landmarks of a bone of a patient. Registration of the landmark registration feature 928 to the landmark of the bone can serve to confirm that a surgeon has located a desired placement and/or orientation for a resection guide 920. In certain embodiments, the navigation guide 902 can include one or more bone engagement surfaces 926 on a surface of the navigation guide 902 that faces a bone or bone fragment. In other embodiments, a resection guide 920 may include no bone engagement surface 926 or landmark registration feature 928.

In certain embodiments, the bone engagement surfaces 926 are patient-specific: contoured to match a surface of one or more bones the resection guide 920 contacts during the procedure. Alternatively, or in addition, the bone engagement surface 926 may not be patient-specific and may, or may not, contact a bone surface during use of the resection guide 920. Those of skill in the art appreciate that one or more sides of any of the members of the system 900 may include one or more bone engagement surfaces 926. Consequently, one or more sides of the navigation guide 902, the resection guide(s) 920, the complementary components 930, fasteners 946, and/or the implants 996 may include one or more bone engagement surfaces 926.

The complementary components 930 can serve to assist a surgeon during one or more steps of a procedure. Those of skill in the art appreciate that a number of components can serve as complementary components 930. One or more of the features, functions, or aspects of the complementary components 930 can include patient-specific features.

Examples of complementary components 930 include, but are not limited to, an alignment guide 932, a rotation guide 934, a reduction guide 936, a compression guide 938, a positioning guide 940, a fixation guide 942, and/or one or more implants 944. In general, the complementary components 930 serve to assist a surgeon in performing the function included in the name of the complementary component 930. Thus, an alignment guide 932 can help a surgeon align bones, parts of bones, anatomical body parts, or other parts of a patient as part of a procedure. A rotation guide 934 can help a surgeon rotate one or more bones, parts of bones, or other body parts of a patient as part of a procedure.

A reduction guide 936 can help a surgeon position and/or orient one or more bones, bone fragments, or other parts of a patient as part of a procedure in order to reduce the bone, bones, bone fragments, or other parts and/or in order to position and/or orient the bone, bones, bone fragments, or other parts to a desired position and/or orientation. A compression guide 938 can help a surgeon compress one or more bones, bone fragments, or other parts of a patient together or against an implant as part of a procedure. A positioning guide 940 can help a surgeon position one or more bones, parts of bones, other parts of a patient, instruments, or other structures as part of a procedure.

In certain embodiments, the positioning guide 940 may be designed and fabricated to be patient-specific. The patient-specific aspects can include a patient-specific bone engagement surface, a predefined angle for reorienting one or more bone or bone parts within one or more planes, a predefined position for bone attachment features 924 or fasteners 946, or the like. Alternatively, or in addition, the positioning guide 940 may be selected from a kit, collection, or repository of a number of positioning guides 940: each having a different configuration for one or more aspects/attributes of the positioning guide 940. For example, each member of the repository/kit may include a different positioning angle (repositioning or correction angle), the angles may differ by two or five degrees for example. In such an embodiment, each positioning guide 940 may not be patient-specific to a particular patient but may provide the desired amount of positioning to meet the goals of the surgeon. In certain embodiments, a preoperative plan generated based on the present disclosure may include a recommendation for the positioning guide 940 to be used, even if the recommended positioning guide 940 is not patient-specific to the particular patient.

A fixation guide 942 can help a surgeon in completing one or more temporary or permanent fixation steps for one or more bones, parts of bones, or other parts of a patient as part of a procedure. The fixation guide 942 may include and/or may use one or more components of a fastener or fixation system including implant hardware of the fastener or fixation system.

One example of a complementary components 930 may include a compressor/distractor, which is one example of a compression guide 938. The compressor/distractor can be used to compress and/or distract bones or parts of bones involved in a procedure.

Advantageously, the system 900 can help a surgeon overcome one or more of the challenges in performing an osteotomy procedure, particularly on bones of a hand or of a foot of a patient, such as on the forefoot, midfoot, or hindfoot. One challenge during an osteotomy procedure can be maintaining control of, and/or position, and/or orientation of a bone, one or more bones, and/or bone pieces/fragments, particularly once a resection or dissection is performed. Advantageously, the navigation guide 902, resection guide(s) 920, and/or complementary components 930 can be configured to assist in overcoming this challenge.

Advantageously, the system 900 can help a surgeon in positioning, placing, and/or orienting a instruments for the procedure accurately. Modern techniques may include pre-operative planning, simulation, or even practice using computer models, 3D printed models, virtual reality systems, augmented reality systems or the like. However, simulations and models are still different from actually positioning a one or more instruments on a patient's bone, joint, or body part during the procedure. The system 900 can include a number of features, including for example the reference features, patient-specific features (which can include reference features), to assist the surgeon with the positioning.

Advantageously, the system 900 can help a surgeon in securing guides of the osteotomy system 900, as well as how to readily remove the instrumentation without disturbing a reduction, shifting, reorienting, or repositioning one or more bones or parts of bones while removing the guide. In certain embodiments, the system 900 is configured to permit removal of instrumentation while keeping temporary fasteners in place for use in subsequent steps of an osteotomy procedure. Alternatively, or in addition, the system 900 facilitates positioning of temporary or permanent fasteners during one step of the osteotomy procedure for use in a subsequent step of the osteotomy procedure. For example, holes or openings formed in the bone during one step of the osteotomy procedure can serve as pilot or starter holes for subsequent permanent fasteners and/or other hardware. Removal of instrumentation during an osteotomy procedure can be particularly challenging where translation and/or rotation of the bones involved in the osteotomy procedure is required for the success of the osteotomy procedure. Advantageously, the system 900 accommodates translation and/or rotation of the bones during the osteotomy procedure while facilitating a successful outcome for the osteotomy procedure.

Advantageously, the components of the system 900 can be specifically designed for a particular patient. Alternatively, or in addition, the components of the system 900 can be specifically designed for a class of patients. Each of the components of the system 900 can be designed, adapted, engineered and/or manufactured such that each feature, attribute, or aspect of the component is specifically designed to address one or more specific indications present in a patient. Advantageously, cuts made for the osteotomy procedure can be of a size, position, orientation, and/or angle that provides from an optimal osteotomy and/or outcome with minimal risk of undesirable resection. In one embodiment, the components of the system 900 can be configured such that an osteotomy is performed that enables a correction in more than one plane in relation to the parts of the body of the patient. For example, cut channels a resection guide 920 can be oriented and configured such that when the bones are fused/fixated the correction results from translation, rotation, and/or movement of bones or bone parts in two or more planes (e.g., sagittal and transverse).

In certain embodiments, the one or more fasteners 946 can include both, one or more permanent fasteners and one or more temporary fasteners. Typically, the fasteners 946 may be used during a variety of different steps of a procedure. Temporary fasteners are often used because they can securely hold bone or bone fragments while steps of the procedure are conducted. A common temporary fastener that can be used with system 900 is a K-wire, also referred to as a pin.

In certain embodiments, the exemplary system 900 may include a plurality of navigation guides 902, resection guides 920, complementary components 930, and/or fasteners 946. For example, a surgeon may plan to resect a plurality of wedge segments from one or more bone(s) in order to accomplish a desired correction. One or more wedge segments may be resected from a medial side of a patient's foot and another one or more wedge segments may be resected from a lateral side of the patient's foot. These wedge segments may extend part way into the foot, or through from one side of the foot to the other. Of course, multiple wedge segments may be formed on one side of the foot as well.

A plurality of wedge segments may be formed using the same resection guide 920 or a plurality of resection guides 920. By using two or more wedge segments, a surgeon may combine the effect of the two or more wedge segments to create a single correction angle that is in a single plane, in two planes, in three planes, or the like. Accordingly, the exemplary system 900 may include multiple navigation guides 902, resection guides 920, complementary components 930, and/or fasteners 946. Alternatively, or in addition, the apparatuses, systems, and/or methods of the present disclosure can be used to provide an osteotomy guide that is a biplanar osteotomy guide. A biplanar osteotomy guide can include a guide in which one or more or each of the resection cuts made are in one, two, or three planes.

Additionally, a surgeon may use one or more components in an exemplary system 900 to make multiple cuts in the bone(s). The multiple cuts may be centered over or around an apex of a deformity or positioned at other locations within the foot such that when the multiple cuts are made, any resected segments removed, or added bone void fillers introduced, and/or bones and/or bone fragments translated and/or rotated the combined angles, surfaces, removed segments, and/or added portions cooperate to provide a desired correction. Each of the components of the exemplary system 900 can be identified, defined, and reviewed using the apparatuses, systems, and/or methods of the present disclosure.

In certain embodiments, the components of the system 900 may be made as small as possible to minimize the amount of soft tissue that is opened or disturbed in the patient for the osteotomy procedure. Alternatively, or in addition, walls and/or sides of the components may be beveled and/or angled to avoid contact with other hard tissue or soft tissues in the operating field for the osteotomy procedure and/or to facilitate handlings and positioning by a user.

Those of skill in the art will appreciate that for certain osteotomy procedures a particular complementary component 930 may not be needed or a particular complementary component 930 may be optional for use in the osteotomy procedure. Similarly, those of skill in the art will appreciate that certain features of the navigation guide 902, resection guides 920, complementary components 930, fasteners 946 can be combined into one or more of apparatus or devices or may be provided using a plurality of separate devices.

Figure 10:
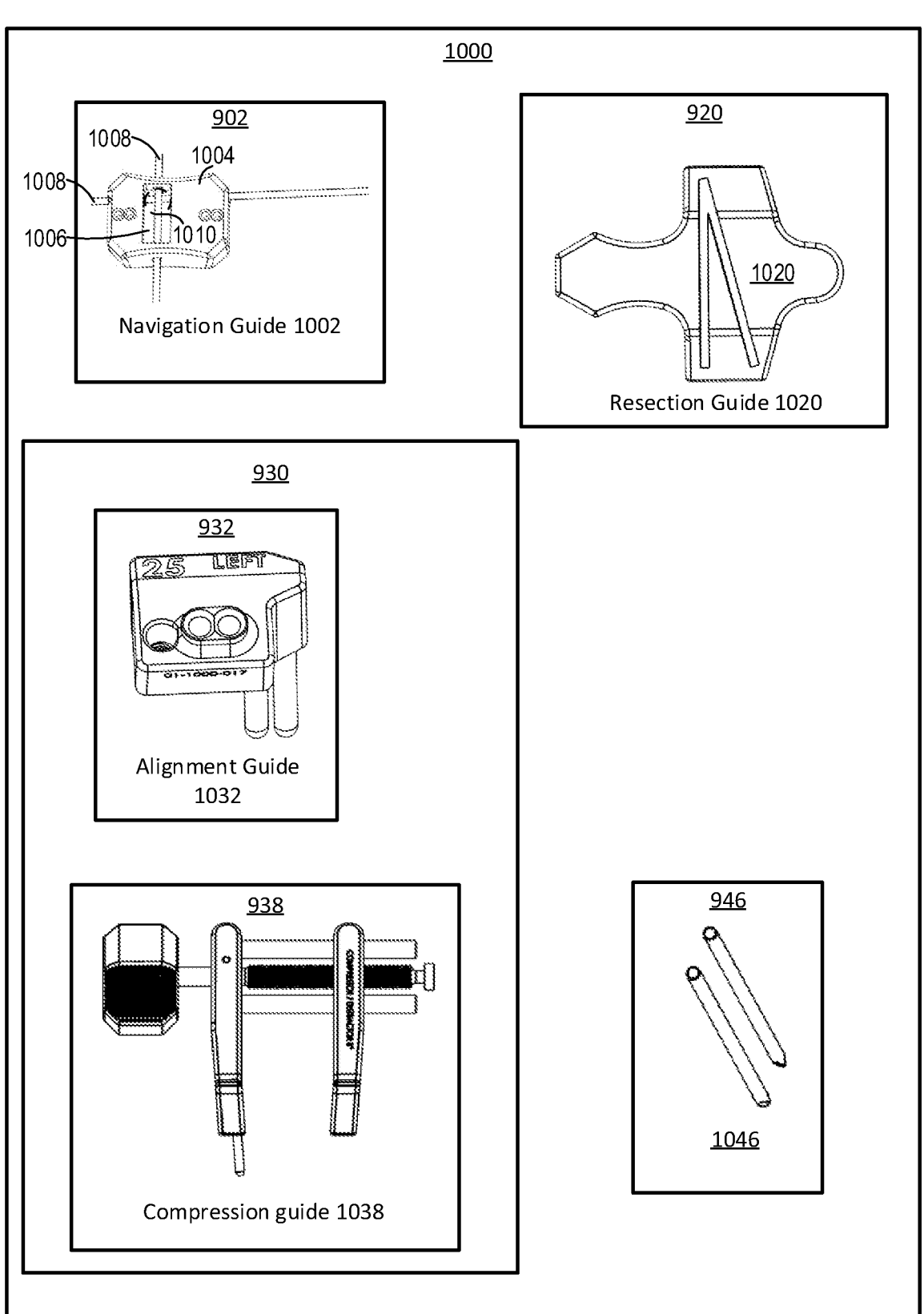
FIG. 10 illustrates an exemplary system for a surgical procedure, according to one embodiment.

FIG. 10 illustrates an exemplary osteotomy system 1000, according to one embodiment. The osteotomy system 1000 may include a navigation guide 902, one example of which is navigation guide 1002, one or more resection guides 920, one example of which is resection guide 1020, one or more other complementary components 930, such as alignment guide 932, one example of which is alignment guide 1032 and/or a compression guide 938, one example of which is compression guide 1038, and one or more fasteners 946, such as fasteners 1046. The osteotomy system 1000 can be used for a variety of surgical procedures.

In certain embodiments, the navigation guide 1002 can be used to create, form, establish, or provide one or more reference features. In particular, the reference features may be formed, created, established, or provided within a single bone, within or on one or more bones, one or more bones of a joint, one or more bones of a plurality of joints, or the like. Initially, the navigation guide 1002 may be positioned before reference features are formed, created, established, or provided.

In the illustrated embodiment, the navigation guide 1002 includes one or more position indicators 1008. Position indicators 1008 serve to indicate a position of one or more objects in relation to another one or more objects. In the illustrated embodiment, two position indicators 1008 work together to indicate position information about one or more objects. Position indicators 1008 are described in more detail herein.

In one embodiment, a user may position the navigation guide 1002 before reference features are formed, created, established, or provided. Alternatively, or in addition, the navigation guide 1002 can be used to form, create, establish, or provide the reference features. In one embodiment, a user, such as a surgeon may initially position the navigation guide 1002 in an approximate position for where the reference features are to be established. Next, the surgeon may use medical imaging, such as fluoroscopy, to determine where the navigation guide 1002 is in relation to one or more bones of a patient, and/or in relation to one or more bones and one or more joints of a patient and/or one or more anatomical references and/or anatomical landmarks. In the illustrated embodiment, the position indicators 1008 can be made of a material that is visible under fluoroscopy. One example material is metal.

Advantageously, the navigation guide 1002 can include two position indicators 1008 that overlap to form a crosshair 1010 within an opening of the navigation guide 1002. A surgeon can visually compare a position of the crosshair 1010 to one or more anatomical structures and/or anatomical references of a patient.

In one example embodiment, a surgeon may position the crosshair 1010 relative to a joint, a plurality of joints, one or more bones, or another anatomical reference of the patient to form, create, establish, or provide one or more reference features for a surgical procedure. By comparing the crosshair 1010 to an initial approximate position, a surgeon can determine if the initial placement of the navigation guide 1002 is in a desired position. If the initial placement, is not in the desired position, a surgeon may adjust the position of the navigation guide 1002 and check the crosshair 1010 again visually or with the help of medical imaging, such as fluoroscopy, to determine if the navigation guide 1002 is now in a desired position. If not, this process of repositioning and rechecking can be repeated until the surgeon positions one or more of the crosshair 1010, a first position indicator 1008, and/or a second position indicator 1008 in a desired position for form, create, establish, or provide one or more reference features.

The osteotomy system 1000 includes resection guide 1020. The resection guide 1020 facilitates resection of hard tissue and/or soft tissue of a patient for a surgical procedure. In one embodiment, the resection guide 1020 can be a stand-alone, separate apparatus. In another embodiment, the resection guide 1020 can be an apparatus that couples to, integrates with, and/or cooperates with a navigation guide 1002 to assist a surgeon in resection of patient tissue.

The osteotomy system 1000 includes a plurality of complementary components 930. The osteotomy system 1000 includes an alignment guide 1032 that facilitates aligning one bone or bone fragment in relation to another bone, a bone fragment, another joint, a plurality of joints, or another anatomical reference or anatomical feature. The osteotomy system 1000 includes compression guide 1038 that facilitates compressing one bone or bone fragment toward or to contact another bone, a bone fragment, a joint, a plurality of joints, or another anatomical reference or anatomical feature. In certain embodiments, the compression guide 1038 can also be used to distract one bone or bone fragment away from another bone, a bone fragment, joint, a plurality of joints, or another anatomical reference or anatomical feature.

In certain embodiments, the one or more fasteners 1046 can include one or more permanent fasteners and/or one or more temporary fasteners. Typically, the fasteners 1046 may be used during a variety of different steps of a procedure. Temporary fasteners are often used because they can securely hold bone or parts/fragments of bones while steps of the procedure are conducted. A common temporary fastener that can be used with osteotomy system 1000 is a K-wire, also referred to as a pin or guide pin.

The osteotomy system 1000 for remediating a bone condition present in a patient includes a navigation guide 1002. The navigation guide 1002 includes a body 1004 that includes a proximal side, a distal side, a medial side, a lateral side, an inferior side, and a superior side. The navigation guide 1002 also includes an opening 1006 that extends from one side of the body 1004 to an opposite side of the body 1004. The opening 1006 can be configured to provide a view of an anatomical reference near the body 1004. The navigation guide 1002 also includes at least one position indicator 1008 that indicates a position of the navigation guide 1002 in relation to one or more anatomical references.

In one embodiment, the navigation guide 1002 also includes an instrument configured to participate in addressing the bone condition present in the patient. The instrument can be used in addressing the bone condition present in the patient. Examples of the instrument include, but are not limited to, a resection guide 1020, a resection insert, a resection adapter, an alignment guide 1032, a compression guide 1038, a fastener 1046, or the like.

The navigation guide 1002 also includes at least one reference feature configured to interface between an instrument and a bone and/or a bone fragment. In one embodiment, the navigation guide 1002 is configured to accept the at least one position indicator 1008. For example, the navigation guide 1002 may include one or more holes or openings that accept one or more position indicators 1008. In one embodiment, the at least one position indicator 1008 extends across an opening 1006 from a first side of the opening 1006 to a second side of the opening 1006, the at least one position indicator 1008 can be configured to align with the anatomical reference or another anatomical reference or an anatomical structure. The osteotomy system 1000 can also include a second position indicator 1008 configured to indicate a trajectory of a first bone, or bone fragment, in relation to a second bone, or bone fragment, after one or more steps of a surgical procedure for addressing a bone condition present in a patient.

In certain embodiments, the osteotomy system 1000 includes at least one position indicator 1008 and a second position indicator 1008 that traverse each other within the opening 1006. In this manner, the least one position indicator 1008 and a second position indicator 1008 may form a crosshair 1010. The osteotomy system 1000 can include at least one resection guide 1020, an alignment guide 1032, and/or a compression guide 1038, in one embodiment.

FIGS. 11A-11G are top perspective, top, bottom, front elevation, rear elevation, left, and right views respectively, of a navigation guide 1102 according to one embodiment. The navigation guide 1102 can be an alternative embodiment of the navigation guide 1002 for use with an osteotomy system. The navigation guide 1102 may have many structures, features, and functions, operations, and/or configuration similar or identical to those of embodiments described herein, such as navigation guide 1002, like parts are, or can be, identified with similar reference numerals. Thus, the navigation guide 1102 includes a body 1104, an opening 1106, and one or more position indicators 1108 (See FIG. 16B).

The body 1104 provides the structural integrity for the navigation guide 1102. The body 1104 can be of a variety of shapes and sizes. The size, shape, and configuration of the navigation guide 1102 may be determined by the surgical procedure the navigation guide 1102 will be used with, by the preferences of a surgeon, by patient-specific features of a patient, a combination of these factors, or the like. Similarly, the size, shape, and configuration of the opening 1106 may be determined by the surgical procedure the navigation guide 1102 will be used with, by the preferences of a surgeon, by patient-specific features of a patient, a combination of these factors, or the like. In certain embodiments, the navigation guide 1102 is patient-specific: fabricated, designed, and/or contoured for the needs of a specific patient and/or preferences of a surgeon and/or can be patient-matched.

In one embodiment, an osteotomy system according to the present disclosure may include a plurality of navigation guides 1102 (e.g., in a kit) to enable use of a navigation guide 1102 that is patient-matched. Each navigation guide 1102 of the plurality may have a different set of configurations, positions, angles, and/or features that may be patient-specific and/or may be generic, and/or meet a surgeon's preferences. The plurality of navigation guides 1102 can be used intraoperatively by a surgeon for a surgical procedure.

In one embodiment, the body 1104 may be as small as possible to serve its function and still be readily handled by a user. In certain embodiments, a body 1104 can include one or more bevels 1110 that can facilitate handling and positioning of the navigation guide 1102 by a user. In another embodiment, the body 1104 may include one or more chamfers instead of bevels 1110 and/or together with one or more bevels 1110. As used herein, "bevel" refers to an edge of a structure that is not perpendicular to the faces of the piece, the edge has a slope or slant or angled profile and can refer to a sloped surface. Often a cutting tool such as a blade or tooth can have a beveled edge that facilitates the cutting edge in cutting into a target material. "bevel" and "chamfer" can be used interchangeably herein. (Search "bevel" on Wikipedia.com May 17, 2021. CC-BY-SA 3.0; search "bevel" on Merriam-Webster.com. Merriam-Webster, 2021. Web.; search "bevel" on wordhippo.com. WordHippo, 2021. Web.; Accessed 4 Aug. 2021. Modified.)

The body 1104 includes a proximal side 1112, distal side 1114, medial side 1116, lateral side 1118, superior side 1120, and an inferior side 1122. The opening 1106 can be configured to provide a view of an anatomical reference near the navigation guide 1102. In one embodiment, the opening 1106 extends from the superior side 1120 to the inferior side 1122. In one embodiment, the opening 1106 has a rectangular shape. Alternatively, or in addition, the opening 1106 can have a round or circular perimeter or a perimeter of a variety of geometric shapes. Alternatively, or in addition, an opening 1106 be of a variety of different sizes. A surgeon may use the opening 1106 to visually check a location of the navigation guide 1102 relative to one or more anatomical references (e.g., using fluoroscopy to position position indicators 1108 relative to anatomical references).

In one embodiment, the opening 1106 can be referred to as a "window". The window 1106 may extend from one side of the body 1104 to an opposite side of the body 1104. The window 1106 is configured to enable a user to view an anatomical reference when the apparatus (e.g., navigation guide 1102) is in use. In one embodiment, the window 1106 extends from the superior side 1120 to the inferior side 1122. The window 1106 may have a square, rectangular, circular, round, oval, or combination of these, shape. In one embodiment, the window 1106 extends from near the medial side 1116 to near the lateral side 1118 to provide a surgeon with as large a view and/or opening as possible to see anatomical structures during a surgical procedure.

In another embodiment, the body 1104 may be transparent and the navigation guide 1102 may not include an opening 1106 because a surgeon may be able to view the position indicators 1108 through the body 1104.

The navigation guide 1102 includes or is configured to accept one or more position indicators 1108. At least one position indicator 1108 is positioned, configured, and/or arranged to indicate a position of the navigation guide 1102 in relation to an anatomical reference. For example, the position indicator 1108 may indicate a position of the navigation guide 1102 relative to a joint (e.g., anatomical reference) of a patient.

In one embodiment, the navigation guide 1102 can include one or more fasteners or couplers configured to engage with a position indicator 1108 and hold the position indicator 1108 in a predetermined position and/or orientation/trajectory. For example, in one embodiment, the fasteners or couplers may be snap-fit couplers/fasteners. In one embodiment, the navigation guide 1102 can include a semi-circular snap fit coupler that includes a semi-circular receiving part that is sized to accept and/or snap around part of the circumference of a position indicator 1108 such as a cylindrical position indicator 1108. Such snap-fit couplers/fasteners can be strategically positioned on one or more sides of the body 1104.

In one embodiment, the navigation guide 1102 may include one or more holes 1124 that extend into the body 1104. The one or more holes 1124 are configured to accommodate one or more of the position indicators 1108. In one embodiment, a plurality of holes 1124 may be configured to accommodate a single position indicator 1108. In certain embodiments, the holes 1124 may be referred to as position indicator holes because they serve to accept and/or retain position indicators 1108. The holes 1124 can be configured to accept position indicators 1108 of different lengths, widths, diameters, and the like.

In the illustrated embodiment, the one or more holes 1124 may be embodied as passages that extend from one side of the body 1104 to the other. For example, one hole 1124*a* may extend from the medial side 1116 to the lateral side 1118 and another hole 1124*b* may extend from the proximal side 1112 to the distal side 1114. Alternatively, or in addition, the one or more holes 1124 may extend into, connect with, or extend through the opening 1106. In another embodiment, the holes 1124 may extend part way into the body 1104 but not all the way through to an opposite side.

Where the navigation guide 1102 includes one or more holes 1124 that connect external sides to internal sides of the opening 1106, the one or more holes 1124 can enable a position indicators 1108 to extend from a first side of the opening 1106 to a second side of the opening 1106. In one embodiment, a position indicator 1108 that extends across the opening 1106 can be configured (e.g., based on where one or more holes 1124 are positioned in the body 1104) to align with an anatomical structure.

In certain embodiments, an osteotomy system can include a first position indicator 1108 that traverses the opening 1106 and a second position indicator 1108 that traverses the opening 1106. The first position indicator 1108 may indicate where the navigation guide 1102 is in relation to an anatomical reference and/or an anatomical structure and the second position indicator 1108 may indicate a trajectory of a first bone, or bone fragment, in relation to a second bone, or bone fragment, after one or more steps for addressing a bone condition present in a patient. Alternatively, or in addition, in one embodiment, a first position indicator 1108 may traverse a second position indicator 1108 within the opening 1106. In certain embodiments, the first position indicator 1108 may traverse the position indicators 1108 and thereby form a crosshair that can be seen using medical imaging such as fluoroscopy.

In certain embodiments, an osteotomy system includes the navigation guide 1102 and the navigation guide 1102 includes one or more guides that can be used to provide, determine, deploy, install, configure, and/or establish at least one reference feature. The at least one reference feature can serve as an interface between an instrument used for a surgical procedure and a bone or a bone fragment of a patient. Those of skill in the art will appreciate that a reference feature may be implemented and/or embodied in a variety of different ways and/or with a variety of different apparatus, devices, structures, and/or systems, each of which is considered within the scope of the present disclosure. In one embodiment, a reference feature may comprise one or more bone tunnels.

In the illustrated embodiment, the at least one reference feature can be embodied as a hole or opening in one or more bones and/or one or more bone fragments. In another embodiment, the at least one reference feature can be embodied as a protrusion or other structure (e.g., a pin, post, bone screw, etc.) connected to or engaged with one or more bones and/or one or more bone fragments.

Advantageously, the navigation guide 1102 can be used to provide one or more different types of reference features. In one embodiment, the navigation guide 1102 includes one or more openings or holes. These openings or holes serve as reference feature guides. Examples of reference feature guides include proximal holes 1126 and/or distal holes 1128). The reference feature guides serve to facilitate and/or to create or provide a reference feature (either or both holes in bone and/or posts or protrusions that extend from bone).

These reference feature guides are configured to guide a user in providing and/or forming and/or creating one or more reference features.

In the illustrated embodiment, one example of a reference feature guide is a hole in the body 1104 that extends from a bone-facing side (e.g., inferior side 1122) of the body 1104 to an opposite side (e.g., superior side 1120) of the body 1104 when the apparatus is used. Of course, reference feature guides may be implemented as holes that connect any two sides of the body 1104.

In the illustrated embodiment, the reference feature guide is a hole having a circle or circular cross section. Alternatively, or in addition, the reference feature guide can have a cross section of a variety of shapes, including geometric shapes such as a square, a rectangle, an oval, or the like. In one embodiment, the reference feature guide may have a capsule shaped cross section that includes a generally oval shape in which two opposite sides of the oval are straight and parallel to each other. Such a cross section may be described as a slot shape. Reference features having a capsule cross section shape can be used in place of multiple holes because use of a capsule or slot shape for a fastener in bone can prevent rotation of the bone and/or a correspondingly shaped instrument that engages a reference feature with a capsule cross section.

In the illustrated embodiment, the one or more openings or holes (e.g., reference feature guides) may extend from a superior side 1120 to an inferior side 1122 of the navigation guide 1102. In one example, holes in the body 1104 (e.g., proximal holes 1126 and distal holes 1128) can be used to drill holes into a bone facing the inferior side 1122. Alternatively, or in addition, in another example, holes in the body 1104 (e.g., proximal holes 1126 and distal holes 1128) can be used to deploy fasteners 1046 into a bone. In each example, the holes in the bone and/or fasteners 1046 in the bone can serve as reference features.

In the illustrated embodiment, the navigation guide 1102 includes a set of proximal holes 1126 and a set of distal holes 1128. Those of skill in the art will appreciate that the navigation guide 1102 can include zero, one, or more proximal holes 1126 and zero, one, or more distal holes 1128. Furthermore, those of skill in the art will appreciate that the proximal holes 1126 and/or distal holes 1128 can be positioned in a variety of locations within the body 1104. Advantageously, the number, size, position, and orientation of the proximal holes 1126 and/or distal holes 1128 can be patient-specific, patient-matched, and/or can be determined or ordered by a surgeon based on the needs of the patient and/or surgeon preferences using the apparatuses, systems, and/or methods of the present disclosure. The illustrated embodiment includes two proximal holes 1126 near a proximal end 1130 and two distal holes 1128 near a distal end 1132. The two proximal holes 1126 can be adjacent to each other, can be spaced, can be aligned, or can have a variety of configurations that can assist a surgeon in performing a surgical procedure. The two distal holes 1126 can be adjacent to each other, can be spaced, can be aligned, or can have a variety of configurations that can assist a surgeon in performing a surgical procedure.

Advantageously, the proximal holes 1126 and/or the distal holes 1128 give the surgeon options for what kind of reference features the surgeon wants to use. In one embodiment, the surgeon may deploy pins or other fasteners through the proximal holes 1126 and/or distal holes 1128 and use the pins as reference features for one or more other steps of a surgical procedure. Alternatively, a surgeon may drill holes into one or more bones positioned adjacent to the navigation guide 1102 that align with the proximal holes 1126 and/or distal holes 1128 and use the holes in the one or more bones as reference features for one or more other steps of a surgical procedure.

Where proximal holes 1126 and/or distal holes 1128 are used to form reference features, the holes formed using the proximal holes 1126 and/or distal holes 1128 can be referred to as anchor holes. Alternatively, or in addition, a surgeon may do a combination of deploying pins and/or drilling holes in one or more bones such that hole reference features and protrusion reference features are provided for one or more other steps of a surgical procedure. In one embodiment, a navigation guide 1102 can include a single proximal hole 1126 and two or more distal holes 1128. In another embodiment, a navigation guide 1102 can include a single distal hole 1128 and two or more proximal holes 1126.

A surgeon can use the navigation guide 1102 to establish or provide one or more reference features for use in one or more steps or stages of a surgical procedure. In one embodiment, the one or more reference features interface, or provide an interface, between one or more bones and/or bone fragments and an instrument that is configured to participate in addressing a bone condition of a patient. Said another way, the instrument is configured to engage with, couple to, register off of, or otherwise associate with or use the reference features as the instrument performs its function for a surgical procedure.

The instrument can be any instrument that can make use of one or more reference features. In one embodiment, the instrument is a resection guide 1020. In another embodiment, the instrument is a resection guide 1202. In another embodiment, the instrument is an alignment guide 1302. In another embodiment, the instrument is a resection guide insert 1820. In another embodiment, the instrument is a complementary component 930 such as a compression guide 1038.

Figures 11A, 11B, 11C, 11D, 11E, 11F, 11G:
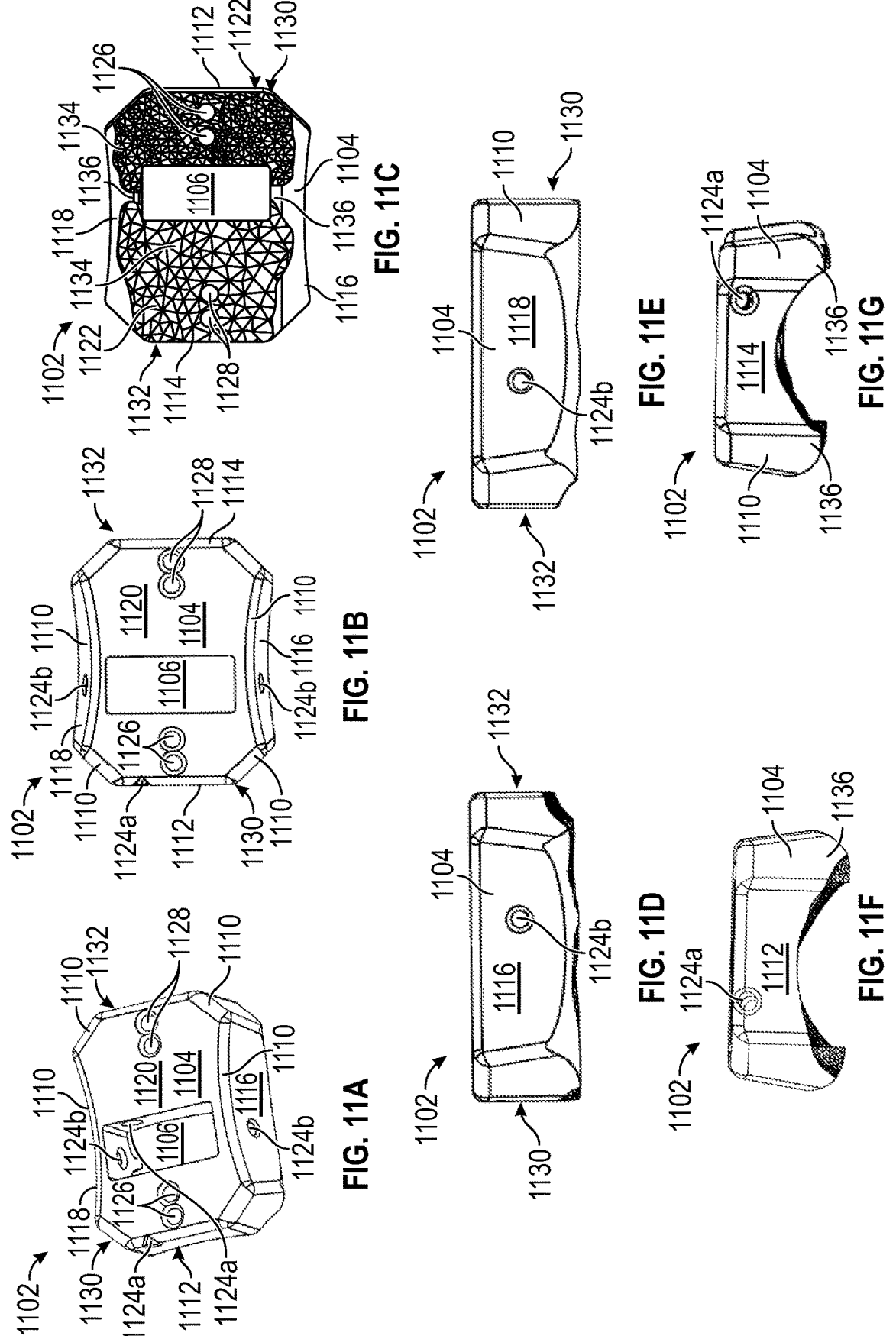
FIGS. 11A-11G are top perspective, top, bottom, front elevation, rear elevation, left, and right views respectively, of a navigation guide according to one embodiment.

FIG. 11A is a top perspective view of one embodiment of a navigation guide 1102. FIG. 11B is a top view of one embodiment of a navigation guide 1102. FIG. 11B illustrates that sides of the body 1104 can be angled between a superior side 1120 and an inferior side 1122.

FIG. 11C is a bottom view of one embodiment of a navigation guide 1102. In certain embodiments, the navigation guide 1102 may include a bone engagement surface 1134. In one embodiment, the bone engagement surface 1134 is on an inferior side 1122 of the body 1104. In one embodiment, the bone engagement surface 1134 is configured to engage with a bone of the patient when the body is in a desired position. In certain embodiments, this means that the bone engagement surface 1134 may be shaped, may be contoured, and/or may be otherwise configured such that each protrusion and/or recess in the bone engagement surface 1134 corresponds to a complementary protrusion and/or recess on the surface of the bone. Advantageously, the navigation guide 1102 is not in the desired position until the bone engagement surface 1134 engages the bone surface in the same way as a model navigation guide 1102 engaged with a bone model of the bone before the navigation guide 1102 was fabricated. Because the bone engagement surface 1134 of the navigation guide 1102 substantially matches the bone engagement surface 1134 of the model navigation guide 1102, moving the navigation guide 1102 to the desired position results in the bone engagement surface 1134 engaging the same protrusions and/or recesses of the bone surface. Thus, once the navigation guide 1102 is moved to where the bone engagement surface 1134 engages or registers with the bone surface, the user is assured that the navigation guide 1102 and its body 1104 is in a desired position.

The desired position may be a position defined for the body 1104 based at least in part on a bone model 404 of a bone of a patient that will be used with the navigation guide 1102. The bone model 404 may be based, at least in part, on anatomic data 412 and/or medical imaging of a patient.

Alternatively, or in addition, the navigation guide 1102 may include one or more bone engagement surfaces 1134. The bone engagement surface 1134 can be shaped based on a bone model of the patient's bones. The bone engagement surfaces 1134 can be defined based on anatomic data 412, medical imaging, bone models, any combination of these, or the like.

The body 1104 may be configured, designed, and/or fabricated to seat transverse to a joint (e.g., a TMT joint) with the bone engagement surface 1134 engaging a first surface of a first bone and a second surface of a second bone. Those of skill in the art will appreciate that the navigation guide 1102 can be used on a single bone, a set of bones, a single joint, and/or a set of joints.

In certain embodiments, the bone engagement surface 1134 can be used to position the navigation guide 1102 in a desired position against one or more bones and/or across one or more joints of a patient (a process referred to as registration, or registration to bone). Alternatively, or in addition, the navigation guide 1102 in certain embodiments may include a side that is configured to register to skin or muscle or other soft tissue of a patient. In either case, the surface contacting the patient anatomy can be contoured to mate with the patient anatomy. In certain embodiments, the navigation guide 1102 can include one or more landmark registration features 1136. In one embodiment, the landmark registration features 1136 may extend from the inferior side 1122. Those of skill in the art will appreciate that a bone engagement surface 1134 and/or landmark registration features 1136 can be positioned on any surface or side of the navigation guide 1102.

FIG. 11D is a front view of the navigation guide 1102. FIG. 11E is a rear view of the navigation guide 1102. FIG. 11F is a left view of the navigation guide 1102. FIG. 11G is a right view of the navigation guide 1102.

Figure 11H:
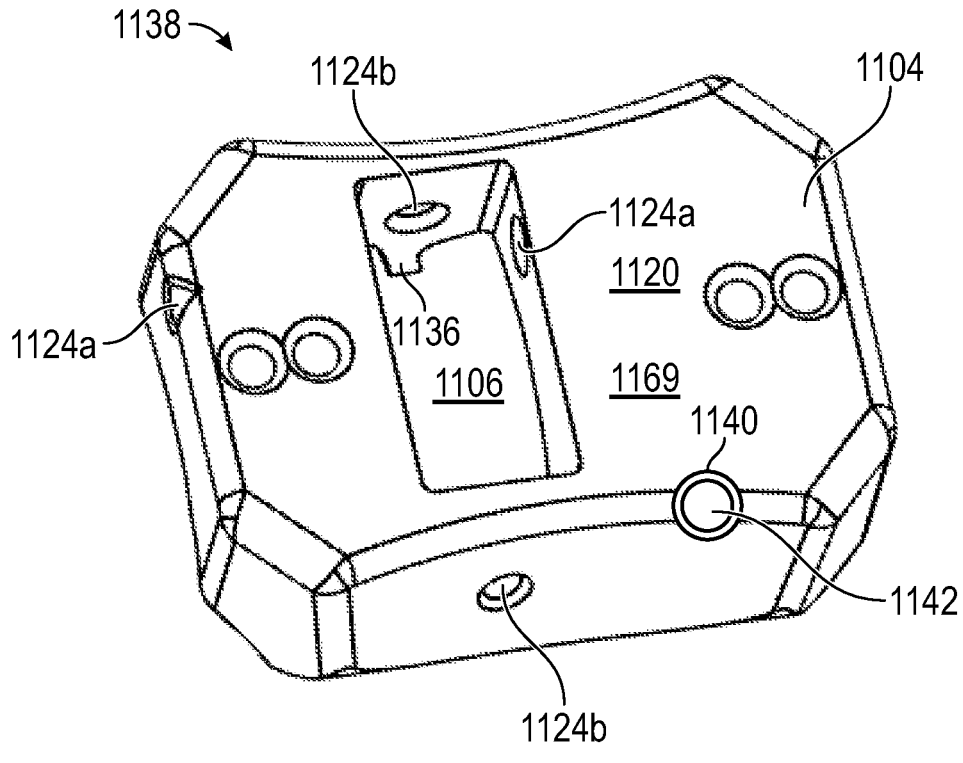
FIG. 11H is a top perspective view of a navigation guide according to one embodiment.

FIG. 11H is a top perspective view of a navigation guide 1138. The navigation guide 1138 is an alternative embodiment of navigation guide 1102. The navigation guide 1138 can include at least part of one or more bone attachment features 1140. The bone attachment feature 1140 may be embodied as a hole 1142 that extends from one side of the navigation guide 1138 to the other. The hole 1142 can be sized to accept a pin or other fastener. A fastener can be deployed through the hole 1142 to hold the navigation guide 1138 stably in place during one or more steps of a surgical procedure. In another embodiment, the bone attachment features 1140 is embodied as a hole 1142 together with a fastener 1046 deployed within the hole.

Figure 11I:
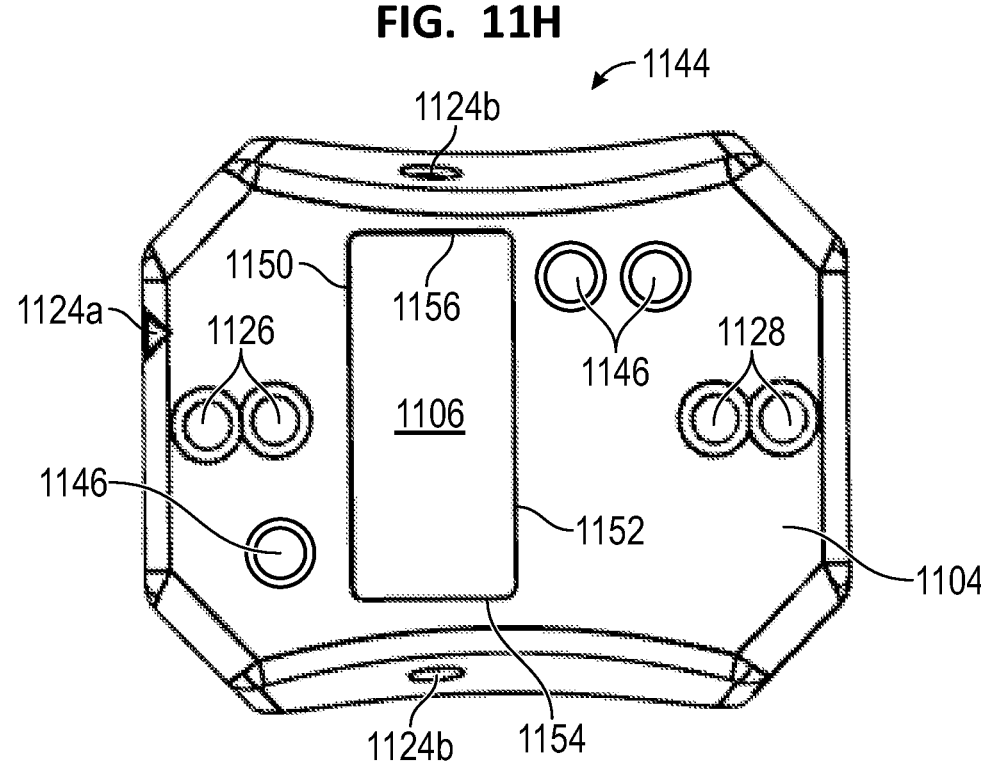
FIG. 11I is a front elevation view of a navigation guide according to one embodiment.

FIG. 11I is a top view of a navigation guide 1144. The navigation guide 1144 is an alternative embodiment of navigation guide 1102 and/or navigation guide 1138. The navigation guide 1144 illustrates another feature of proximal holes 1126 and/or distal holes 1128. In certain embodiments, the present disclosure can be used to recommend to a surgeon that any fasteners deployed through the proximal holes 1126 and/or distal holes 1128 be deployed to a predefined depth. Similarly, the present disclosure can be used to recommend to a surgeon that holes drilled in bone through the proximal holes 1126 and/or distal holes 1128 be drilled to a predefined depth. Alternatively, or in addition, the present disclosure may provide one or more stops that facilitate a surgeon deploying fasteners or drilling holes to a predefined depth.

The depth of holes formed in one or more bones as part of using the navigation guide 1144 can be predefined and planned such that the same holes can be used for more than one purpose during a surgical procedure. For example, drilled holes or holes left after using deployed fasteners can be reused for deployment of bone screws, compression screws, bone plate prongs, and/or other fixation hardware, or the like. Using holes in bones for more than one purpose can save a surgeon steps later on in a surgical procedure.

In the illustrated embodiment, the proximal holes 1126 and/or distal holes 1128 can be used for subsequent fixation of a bone, bones, or bone fragments of a patient. Alternatively, or in addition, the navigation guide 1144 can include one or more additional holes 1146 that can be used for fixation of bones of a patient as part of a surgical procedure. A surgeon may optionally deploy pins or other fasteners in the one or more additional holes 1146 or drill holes in bone using the one or more additional holes 1146. The holes in the bone can then be used for fixation hardware deployed by the surgeon. In this manner, the proximal holes 1126, distal holes 1128, and/or one or more additional holes 1146 of the navigation guide 1144 can be used as a template for temporary or permanent fixation of one or more bones and/or bone fragments.

FIG. 11I illustrates one example of a window 1106. The window 1106 may extend from a superior side 1120 to an inferior side 1122 of the body 1104. The window 1106 may include a proximal edge 1150, a distal edge 1152, a medial edge 1154, and a lateral edge 1156. The window 1106 is configured to enable a user to view an anatomical reference when the apparatus (e.g., navigation guide 1102) is in use. In one embodiment, the window 1106 extends from near the medial side 1116 to near the lateral side 1118 to provide a surgeon with as large a view and/or opening as possible to see anatomical structures during a surgical procedure. In certain embodiments, a surgeon may decide what shape, size, position, and/or configuration they would like for the window 1106.

FIGS. 12A-12G are top perspective, top, bottom, front elevation, rear elevation, left, and right views respectively, of a resection guide 1202 according to one embodiment. The resection guide 1202 can be an alternative embodiment of the resection guide 1020 for use with an osteotomy system. The resection guide 1202 may have many structures, features, and functions, operations, and/or configuration similar or identical to those of embodiments described herein, such as resection guide 1020, like parts are identified with the same or similar reference numerals.

Thus, the resection guide 1202 may have a body 1210 with a monolithic construction and the general shape of a rectangular shape. The body 1210 includes a proximal side 1212, a distal side 1214, a medial side 1216, a lateral side 1218, a superior side 1220, and an inferior side 1222. In the illustrated embodiment, the body 1210 may also include a proximal arm 1230 that extends from the body 1210 and a distal arm 1240 that extends from the body 1210. The proximal side 1212 is the side closest to the core of the patient when the resection guide 1202 is in use. A proximal end of the resection guide 1202 may be at or near the proximal side 1212. The distal side 1214 is the side furthest from the core of the patient when the resection guide 1202 is in use. A distal end of the resection guide 1202 may be at or near the distal side 1214. The medial side 1216 is the side facing medially or plantarly when the resection guide 1202 is in use. The lateral side 1218 is the side facing laterally or dorsally when the resection guide 1202 is in use. The superior side 1220 is the side facing up away from the bone(s) when the resection guide 1202 is in use. The inferior side 1222 is the side facing down, facing, and/or contacting the bone(s) (e.g., contacting a surface of one or more bones) when the resection guide 1202 is in use.

The inferior side 1222 (See FIG. 12C) may be custom contoured to match the shapes of one or more of the surfaces of two or more bones of a joint or a set of joints. In one embodiment, the inferior side 1222 is contoured to match a first cuneiform and/or a first metatarsal. In one embodiment, the inferior side 1222 may include a bone engagement surface 1224. The bone engagement surface 1224 can be shaped to match a first surface of a first bone and a second surface of a second bone of a joint, in one embodiment. In another embodiment, the inferior side 1222 may not be contoured and/or may not include one or more bone engagement surfaces 1224.

In one example, the bone engagement surface 1224 can be shaped such that the bone engagement surface 1224 matches a surface of a cuneiform bone and a surface of a metatarsal bone of a tarsometatarsal ("TMT") joint. The bone engagement surface 1224 can be so shaped because it is fabricated from a bone model of the patient's bones. The body 1210 may be configured, designed, and/or fabricated to seat transverse to a joint (e.g., a TMT joint) with the bone engagement surface 1224 engaging a first surface of a first bone and a second surface of a second bone. Those of skill in the art will appreciate that the resection guide 1202 can be used on a single bone, a set of bones, a single joint, and/or a set of joints.

FIGS. 12A-12G illustrate a resection guide 1202 that includes a body 1210, bone engagement surface 1224, and/or one or more arms (e.g., proximal arm 1230 and/or distal arm 1240) configured to couple to the bones and extend transverse to the joint, at least partially, if not completely, on the dorsal sides of the bones. Accordingly, the resection guide 1202 may be referred to as a dorsal resection guide.

In certain embodiments, the resection guide 1202 may not include a bone engagement surfaces 1224. Instead, the navigation guide 1102 and reference features provided for the resection guide 1202 may be sufficient to position the resection guide 1202. For example, the bone attachment feature 1280 may engage holes formed in bones using reference feature guides such that holes/reference features adequately position the resection guide 1202 for use. Alternatively, or in addition, the resection guide 1202 may include an inferior side 1222 that is sized and/or contoured to be patient-matched.

In addition, the resection guide 1202 may be configured to mitigate or avoid contact with soft tissue such as nerves, tendons, blood vessels, and the like that may run along a medial and/or a lateral side of a first metatarsal. Accordingly, the resection guide 1202 may be fabricated to seat transverse to the TMT joint such that the bone engagement surface contacts a dorsal surface of a first bone (e.g., first cuneiform 202) and/or a second bone (e.g., first metatarsal 230). For example, the proximal arm 1230 and/or distal arm 1240 may be positioned more towards a lateral side 1218.

In the illustrated embodiment, the body 1210 is configured to reside on the dorsal surfaces of the first cuneiform and the first metatarsal to provide proper alignment of the body 1210 with the metatarsocuneiform joint (e.g., the joint between the first metatarsal and the medial cuneiform bone, aka a TMT joint). In another embodiment, the body 1210 is configured to reside or sit between the medial surfaces and the dorsal surfaces for an osteotomy. The body 1210 may have only one stable position and orientation relative to the first cuneiform and the first metatarsal during a surgical osteotomy for correcting the condition.

Advantageously, the fidelity of the patient imaging data enables the bone model, preliminary resection guide model, and patient specific instrument (e.g., patient specific resection guide, patient specific pin guide, patient specific alignment guide, etc.) to uniquely match a particular patient. Consequently, the bone engagement surface 1224 can engage the surfaces of the bones of a joint in a single configuration. Such a close matching fit facilitates the surgical osteotomy.

Figures 12A, 12B, 12C, 12D, 12E, 12F, 12G:
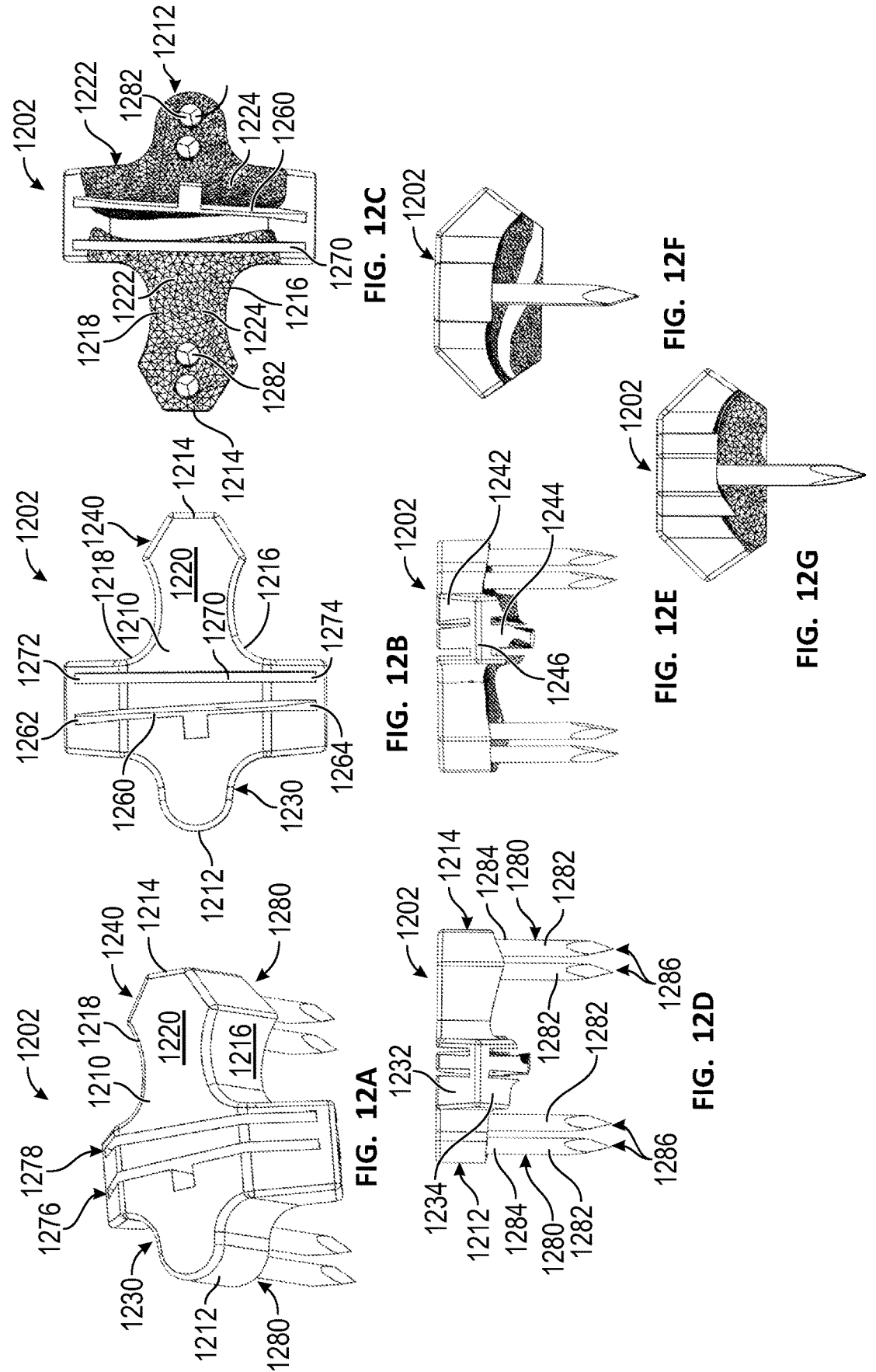
FIGS. 12A-12G are top perspective, top, bottom, front elevation, rear elevation, left, and right views respectively, of a resection guide according to one embodiment.
Figures 13A, 13B, 13C, 13D, 13E, 13F, 13G:
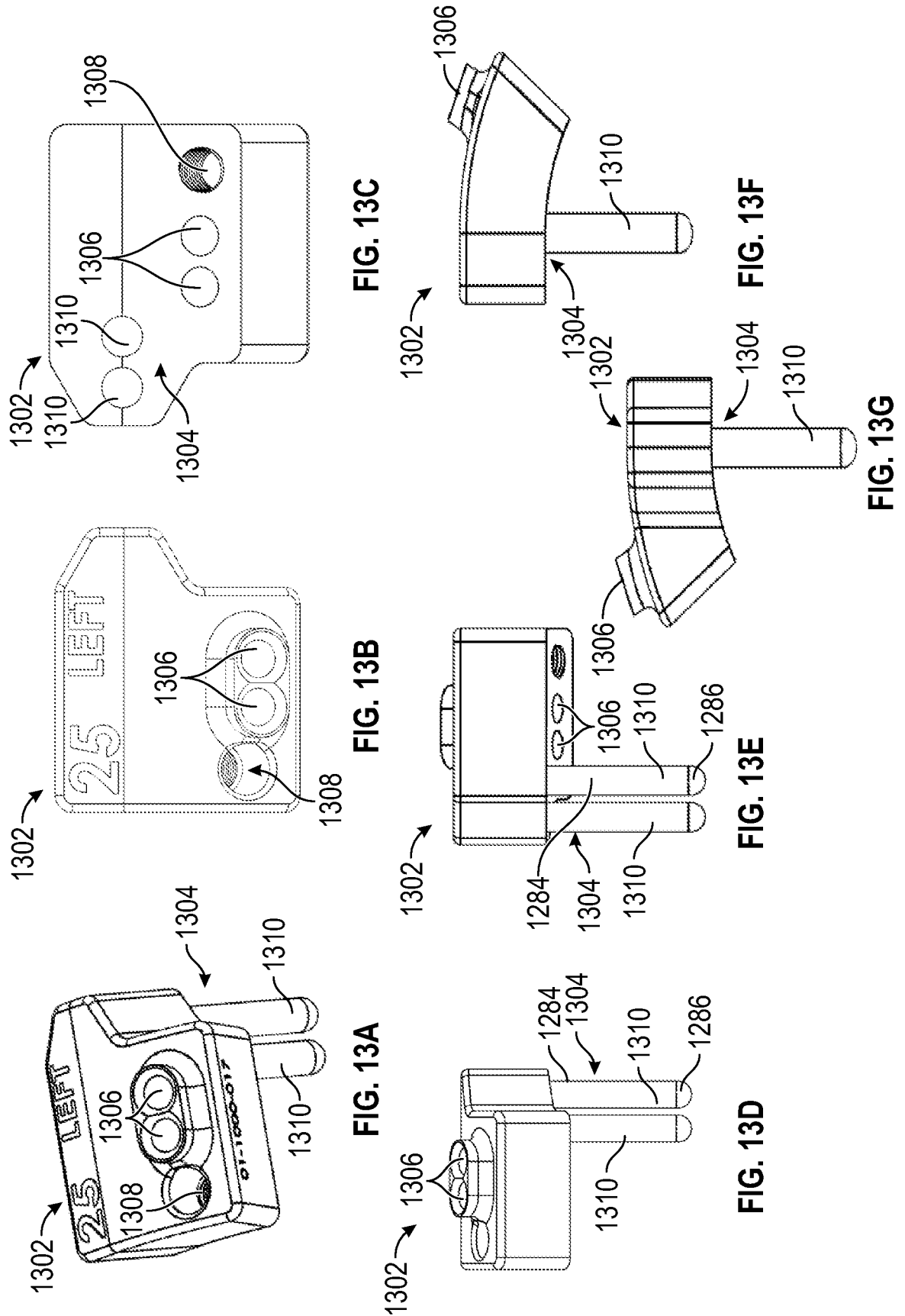
FIGS. 13A-13G are top perspective, top, bottom, front elevation, rear elevation, left, and right views respectively, of an alignment guide according to one embodiment.
Figures 14A, 14B, 14C, 14D, 14E, 14F, 14G:
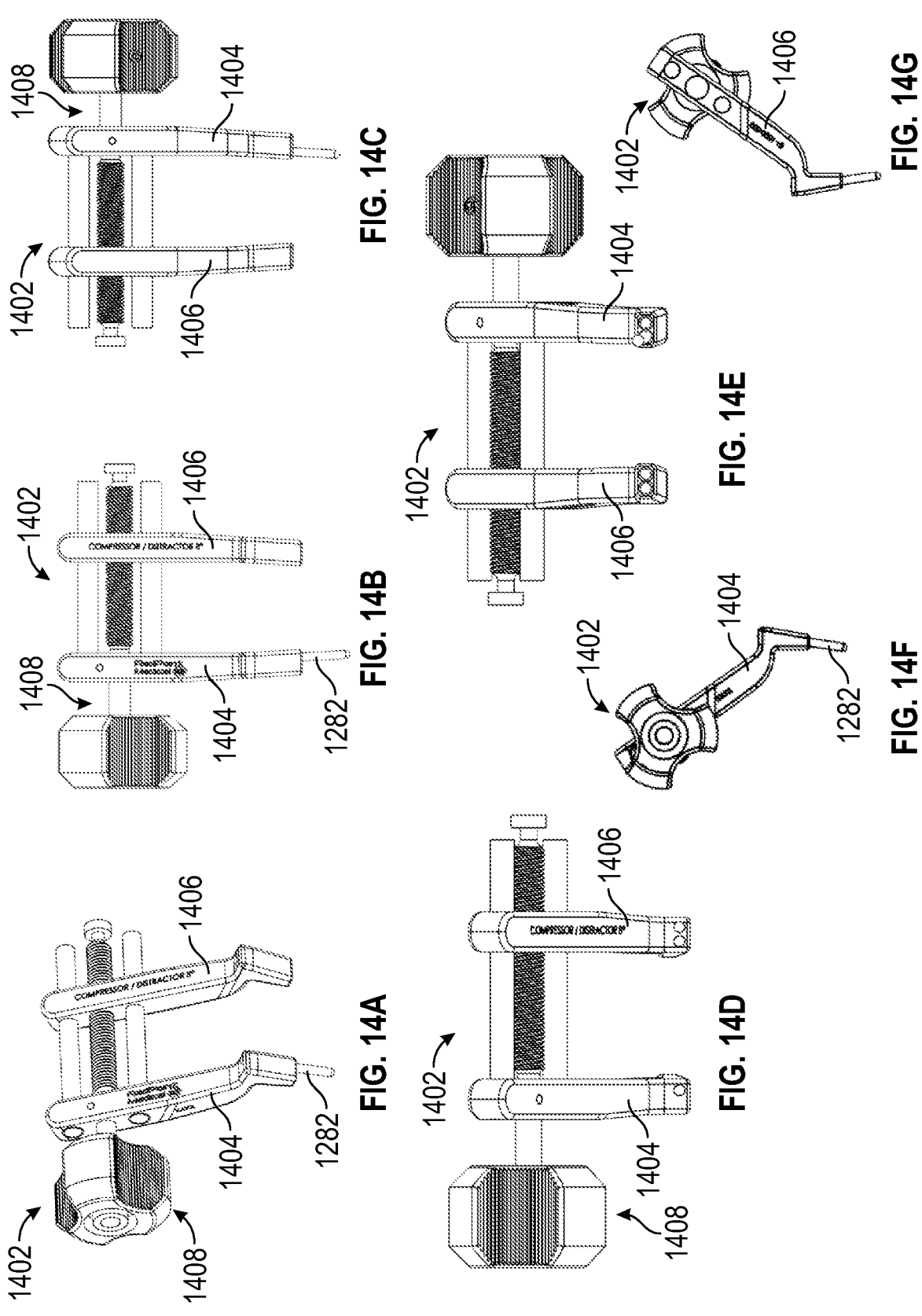
FIGS. 14A-14G are top perspective, top, bottom, front elevation, rear elevation, left, and right views respectively, of a compression guide according to one embodiment.
Figures 15A, 15B, 15C, 15D, 15E, 15F, 15G:
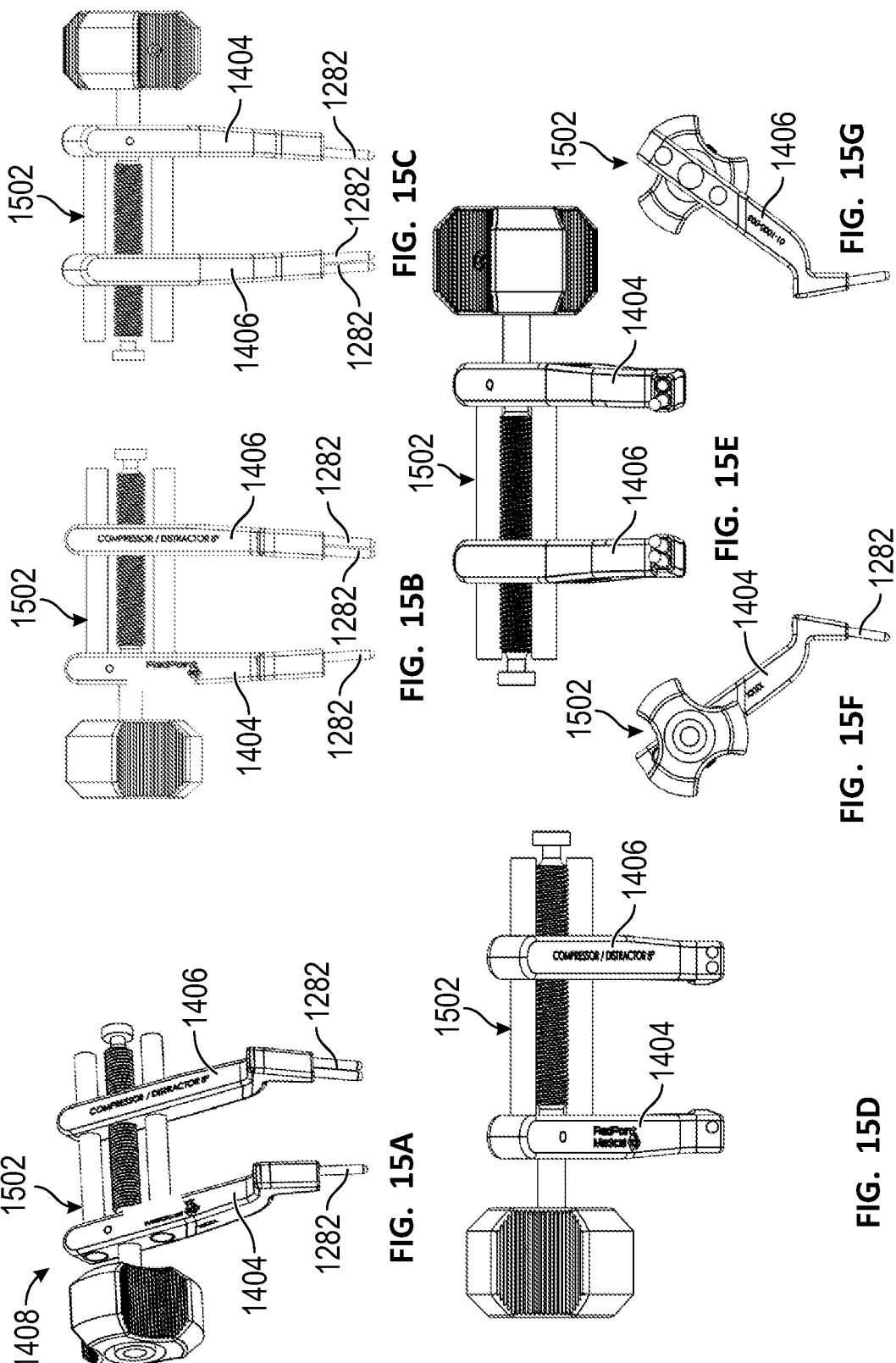
FIGS. 15A-15G are top perspective, top, bottom, front elevation, rear elevation, left, and right views respectively, of a compression guide according to one embodiment.

FIG. 12D illustrates the resection guide 1202 from a view facing the medial side 1216. FIG. 12E illustrates the resection guide 1202 from a view facing the lateral side 1218. In certain embodiments, the resection guide 1202 may include one or more features that facilitate use of the resection guide 1202 while avoiding certain soft tissue in the vicinity of a joint. For example, the medial side 1216 may include a medial superior surface 1232 and a medial inferior surface 1234 that meet at a medial edge 1236. Advantageously, the medial inferior surface 1234 may extend from inferior side 1222 to the medial edge 1236 at an angle such that the medial inferior surface 1234 does not impinge soft tissue near the joint (e.g., near a medial end of the joint). In certain embodiments, the angle may range between about 80 and 170 degrees. In another example, the lateral side 1218 may include a lateral superior surface 1242 and a lateral inferior surface 1244 that meet at a lateral edge 1246 (See FIG. 12E). Of course, the medial superior surface 1232 may extend from the superior side 1220 to the medial edge 1236 at an angle. The angle of the medial superior surface 1232 may enable use of the resection guide 1202 in tighter openings and thus minimize the size of incisions used for a procedure.

Advantageously, the lateral inferior surface 1244 may extend from inferior side 1222 to the lateral edge 1246 at an angle such that the lateral inferior surface 1244 does not impinge soft tissue near the joint (e.g., near a medial end of the joint). In certain embodiments, the angle may range between about 80 and 170 degrees. Of course, the lateral superior surface 1242 may extend from the superior side 1220 to the lateral edge 1246 at an angle. The angle of the lateral superior surface 1242 may enable use of the resection guide 1202 in tighter openings and thus minimize the size of incisions used for a procedure.

The body 1210 may further include one or more resection guide features that guide a cutter to resect the first cuneiform and the first metatarsal in the manner needed to make a desired correction. For example, the resection guide features may be used to guide a planar cutting blade, an arcuate cutting blade, a drill or mill, a burr, and/or the like. In one embodiment, the resection guide 1202 may include a first resection guide feature and a separate resection guide 1202' may include a second, different resection guide feature.

In the embodiment of FIGS. 12A through 12G, the resection guide features may guide a reciprocating planar blade, such as that of a surgical bone saw, that forms planar cuts in the first cuneiform and the first metatarsal, for example. Various manual or powered tools may be used to form the planar cuts. In one embodiment, a sagittal bone saw can be used. In one example, the resection guide features may take the form of a first slot 1260 and a second slot 1270. The first slot 1260 may include a lateral end 1262 and a medial end 1264. The second slot 1270 may include a lateral end 1272 and a medial end 1274.

In one embodiment, the first slot 1260 and the second slot 1270 extend from the superior side 1220 to the inferior side 1222. In certain embodiments, the first slot 1260 may extend from near the lateral side 1218 to near the medial side 1216. In other embodiments, one of, or both of, the first slot 1260 and the second slot 1270 may extend from one of the medial side 1216 or the lateral side 1218 of the body 1210. In certain embodiments, the first slot 1260 and second slot 1270 intersect. In other embodiments, the first slot 1260 and second slot 1270 do not intersect.

Thus, upon desired positioning of the resection guide 1202, the second slot 1270 may be positioned over at least a portion of the first cuneiform to facilitate resection of the first cuneiform, while the first slot 1260 may be positioned over at least a portion of the first metatarsal to facilitate resection of the first metatarsal. In one embodiment, the second slot 1270 is positioned near the distal end of the first cuneiform and the first slot 1260 is positioned near the proximal end of the first metatarsal. The first slot 1260 and second slot 1270 together, with the bone engagement surface 1224 overlying the first cuneiform and the first metatarsal, are positioned to guide resection of the first cuneiform and the first metatarsal during a surgical osteotomy for correcting a condition.

In alternative embodiments, a resection guide feature may be designed to guide a different type of cutter, such as a drill, mill, or side-cutting burr. In such embodiments, the resection guide feature may not be a slot, but may instead be a translatable or rotatable cutter retainer that guides translation and/or rotation of the cutter relative to the bone. In certain embodiments, two or more resection guide features may be replaced by a single resection guide feature sized to permit a surgeon to resect both a first cuneiform and a first metatarsal using a single resection guide 1202.

In one embodiment, a first resection guide feature is configured to define a first cut surface that can be formed by resecting a first bone. A second resection guide feature is configured to define a second cut surface that can be formed by resecting a second bone. In such an embodiment, one or the other or both of the first cut surface and the second cut surface can be oriented according to one or more angles relative to landmarks on the bones or other anatomical structures.

In the illustrated embodiment, the resection guide 1202 includes one or more resection guide features 1276, 1278. The resection guide feature 1276,1278 guides a surgeon in performing a resection by facilitating keeping a cutting tool in line with, and/or within the resection guide feature 1276,1278 (at a desired trajectory relative to one or more bones of the patient). In the illustrated embodiments, the resection guide feature 1276,1278 is shaped like a slot or a channel and includes a first end and a second end. In the illustrated embodiment, the first end and/or second end may be open ended or closed ended.

FIGS. 12A and 12D-12G illustrate that the resection guide 1202 can include a bone attachment feature 1280. The bone attachment feature 1280 serves to connect or couple the resection guide 1202 to one or more bones, at least temporarily (e.g., during a surgical procedure). The bone attachment feature 1280 secures the resection guide 1202 to the one or more bones.

In the illustrated embodiment, the bone attachment feature 1280 may be embodied using one or more prongs 1282. The prongs 1282 are configured to engage with our couple with one or more bones and/or bone fragments of a patient. The prongs 1282 can have a variety of shapes, sizes, diameters, lengths, and/or configurations as needed. Advantageously, a surgeon may request that a certain type or configuration of prongs 1282 be used for a particular surgical procedure. In one embodiment, the prongs 1282 are cylindrical and have a circular cross-section.

The prongs 1282 have a proximal end 1284 and distal end 1286. In one embodiment, the prongs 1282 may include a fastener, such as external or internal threads that engage with corresponding threads of a hole or post that extends from the body 1210. In the illustrated embodiment, the prongs 1282 may be formed as part of the body 1210 and may extend from the inferior side 1222. The distal end 1286 of one or more of the prongs 1282 may be blunt, rounded, tapered to come to a point, or the like.

In certain embodiments, one end or the other (e.g., proximal arm 1230 and/or distal arm 1240) of the resection guide 1202 may include a hole that can receive a fastener such as pin that can be used to provide added securement of the resection guide 1202 against one or more bones.

The resection guide 1202 can be used in a variety of procedures. In one embodiment, the resection guide 1202 can be positioned such that the prongs 1282 fit or seat within reference features (e.g. holes in one or more bones). The resection guide 1202 can be pressed towards the one or more bones such that prongs 1282 enter the reference features (e.g. holes in one or more bones).

Alternatively, or in addition, a surgeon can position a resection guide 1202 having prongs 1282 on one or more bones and tap the prongs 1282 into the bone(s) using a mallet. Even if there are reference features embodied as holes, a surgeon may tap the resection guide 1202 into the holes with a mallet to seat the resection guide 1202.

The relationship between the bone attachment feature 1280 and the reference feature(s) forms an interface between the reference features and the resection guide 1202. Those of skill in the art will appreciate that there are various permutations of configurations of one or more prongs 1282, and reference features. For example, the proximal arm 1230 may include one or more holes that slide over one or more posts or pins that extend from one or more bones and the distal arm 1240 may include prongs 1282 that fit into one or more holes in the one or more bones.

One challenge when doing resection of hard or soft tissue of a patient, is to manage, mitigate, and/or avoid introducing foreign objects or materials into the body of the patient. Where a cutting tool is used, there is a risk that the cutting tool may cut material from one or more instruments and that this cut material, debris, can be introduced to the body of the patient and may be difficult or impossible to remove. This challenge is overcome by making a resection guide 1202 out of materials that the cutting tool cannot cut or has a low risk of cutting. Thus, the resection guide 1202 may be made from metal. One example metal is titanium.

Advantageously, because of the reference features identified using the navigation guide 1002, the resection guide 1202 does not need to be as stiff as it might otherwise be. Since the resection guide 1202 is not used to determine and form the reference features, the resection guide 1202 can be focused on guiding a cutting tool. Consequently, the resection guide 1202 can be made of more lightweight metals, can be made from less metal material (e.g., include hollowed out portions or be configured as a shell) that serves the functions of the resection guide 1202 but uses less material. (e.g., less metal).

FIGS. 13A-13G are top perspective, top, bottom, front elevation, rear elevation, left, and right views respectively, of an alignment guide 1302 according to one embodiment. The alignment guide 1302 can be an alternative embodiment of the alignment guide 1032 for use with an osteotomy system. The alignment guide 1302 may have many structures, features, and functions, operations, and/or configuration similar or identical to those of embodiments described herein, such as alignment guide 1032, like parts are identified with the same reference numerals, except the first digit of the reference number is changed for this embodiment.

In certain embodiments, proximal reference features may be formed in a proximal bone or bone fragment and distal reference features may be deployed or formed or otherwise provided in a distal bone or bone fragment. The alignment guide 1302 is configured to engage with one or more proximal distal features, such as for example holes in one or more bones formed using the navigation guide 1102.

The alignment guide 1302 serves to facilitate aligning one bone or bone fragment with another bone or bone fragment. In one embodiment, this alignment may include rotation of one bone relative to another by a certain number of degrees. Rotation may be desired for a procedure such as a Lapidus correction procedure.

The alignment guide 1302 facilitates determining where to engage with a bone or bone fragment such that the bone fragment can be aligned to a desired position (including rotation) when the bone is reduced with another bone or bone fragment. The alignment guide 1302 includes a bone attachment feature 1304, one or more alignment features 1306 and may optionally include a handle or a fastener 1308 for connecting a handle.

In one embodiment, the bone attachment feature 1304 can be realized by one or more prongs 1310. The one or more prongs 1310 may be substantially similar to the prongs 1282 described herein. In the illustrated embodiment, the one or more prongs 1310 may have a rounded or blunt distal end 1286. The one or more prongs 1310 are configured to fit within reference features (e.g., holes) formed in bone of a patient.

The alignment features 1306 are positioned in the alignment guide 1302 relative to these reference features. The alignment features 1306 are positioned and angled based on the needs of a patient, patient-specific anatomical structures of the patient, and/or surgeon preferences. In certain embodiments, the alignment features 1306 are offset from the bone attachment feature 1304 by a certain distance that corresponds to a number of degrees of rotation of a first bone or bone fragment from an original position to a new positioned after rotating the first bone or bone fragment about its longitudinal axis. The first bone or bone fragment can be rotated a certain number of degrees about its longitudinal axis in either a clockwise or a counterclockwise direction. Typically, the first bone or bone fragment is rotated counterclockwise to address a condition such as a hallux valgus condition.

A surgeon may not know pre-operatively how much rotation is needed or that can be achieved given the condition and anatomy of the patient. Accordingly, the present disclosure may include a number of alignment guide 1302 each with a different number of degrees of correction built into the placement of the alignment features 1306 relative to the bone attachment feature 1304. Examples include a 25-degree alignment guide 1302, 30-degree alignment guide 1302, 35-degree alignment guide 1302, 40-degree alignment guide 1302, 10-degree alignment guide 1302, 15-degree alignment guide 1302, and the like.

Each alignment guide 1302 that provides a different number of degrees of rotation may include a marking that identifies the number of degrees (e.g., "25", "30", etc.). Alternatively, or in addition, certain alignment guides 1302 may be configured for use on a joint of a left foot versus a right foot. Similarly, such alignment guide 1302 may include an indicator of which foot the guide is to be used with (e.g., "Left", "Right"). Those of skill in the art will appreciate that the degrees for the alignment guide 1302 may range from about 2 degrees to about 100 degrees.

The alignment guide 1302 can be used for form alignment features 1306 in bone of a patient. The alignment features 1306 can be holes in the bone or protrusions or posts that are secured into the bone. Where the alignment features 1306 are holes, a surgeon may use the alignment guide 1302 to drill holes into the bone at the desired locations. Where the alignment features 1306 are pins or posts extending from the bone, a surgeon may use the alignment features 1306 to deploy pins into the bone at the desired locations. The alignment guide 1302 may be removed and deployed pins may remain in the locations indicated by the alignment features 1306.

In an alternative embodiment, the bone attachment feature 1304 can be realized by holes in the alignment guide 1302 that can slide over posts or pins extending from a bone that serve as reference features. Alternatively, or in addition, the alignment features 1306 can be realized by pins deployed through holes in the alignment guide 1302. In such an embodiment, the alignment guide 1302 may be referred to as a pin guide.

The fastener 1308 can be realized by a hole with internal threads configured to engage external threads of a handle that can be screwed into the hole.

As with the resection guide 1202, the alignment guide 1302 can include one or more bone attachment feature 1304. Alternatively, or in addition, the bone attachment feature 1304 can be a combination of holes that engage posts/pins or one or more prongs 1310 (reference features) that engage holes (reference features) of the bone.

Referring now to FIGS. 11A-13G, those of skill in the art will appreciate that one or more of the components, devices, and/or systems disclosed in the present disclosure can be used for minimally invasive surgery, minimally invasive surgical procedures, MIS.

For example, first, a surgeon may position and/or orient a navigation guide 1102 on a surface of skin of a patient. In such an embodiment, the inferior side 1122 of the navigation guide 1102 may include an engagement surface 1134 that is contoured to register to skin and/or one or more landmarks on a surface of an anatomical structure of a patient. As explained above, a surgeon may use the opening 1106 to visually check a location of the navigation guide 1102 relative to one or more anatomical references (e.g., using fluoroscopy to position position indicators 1108 relative to anatomical references). If the navigation guide 1102 is not yet in the desired position, a surgeon may reposition the navigation guide 1102 and/or recheck the position using fluoroscopy until the navigation guide 1102 is in the desired position.

Next, a surgeon may create a pierce incision through skin of the patient where the proximal holes 1126 and/or distal holes 1128 are located— using the proximal holes 1126 and/or distal holes 1128 as guides in making the incisions. Alternatively, or in addition, a surgeon may deploy a pin, K-wire, other fastener, or use a drill bit to drill through the skin and into one or more bone(s) below the skin surface.

Alternatively, or in addition, in one embodiment a surgeon may mark using a marker or pen on the skin where the proximal holes 1126 and/or distal holes 1128 contact the skin. Next, a surgeon may deploy a pin, K-wire, other fastener, or use a drill bit to drill through the skin and into one or more bone(s) below the skin surface. In this manner, minimal sized incisions have been made. And the reference features have been identified.

In one embodiment, where a surgeon deploys pins through the proximal holes 1126 and/or distal holes 1128, alternative embodiments of the resection guide 1202 and/or alignment guide 1302 can include one or more cannulated prongs 1282 and/or cannulated one or more prongs 1310. "Cannulated" herein means a structure that includes an opening that extends from one end of the structure to another. Typically, the opening is cylindrical and sized to accept a tool, fastener, or other instrument.

In an embodiment of a resection guide 1202 and/or alignment guide 1302 with one or more cannulated prongs 1282 and/or cannulated one or more prongs 1310, the cannulated prongs may be sized to slide over pins, K-wires, or other fasteners that extend from one or more bones of a patient. In this manner, the one or more cannulated prongs 1282 and/or cannulated one or more prongs 1310 may cooperate with the pins to secure an instrument in place while a surgeon uses the instrument for one or more of its purposes. In an embodiment with a resection guide 1202 and/or alignment guide 1302 with one or more cannulated prongs 1282 and/or cannulated one or more prongs 1310, the engagement surface of the resection guide 1202 and/or inferior surface of the alignment guide 1302 may not be patient-specific and may not be contoured.

In one embodiment, a surgeon using the resection guide 1202 for a MIS surgical procedure may position the resection guide 1202 on top of the skin, with the bone attachment features 1280 engaging reference features coupled to or formed in the bone(s). Next, a surgeon may make an incision through the skin of the patient contacting the first resection guide feature 1276 and/or the second resection guide feature 1278. Once these incisions are made, a surgeon may retract skin away from the newly formed incisions. Next a surgeon may resect underlying bone(s) by way of the first resection guide feature 1276 and/or second resection guide feature 1278.

In one embodiment, a single proximal reference feature and a single distal reference feature are used, the resection guide 1202 may include a single bone attachment feature 1280 near the proximal arm 1230 and a single bone attachment feature 1280 near the distal arm 1240. At this stage in an MIS surgical procedure, the patient may have only four minimally sized incisions (e.g., one for each single bone attachment feature 1280 and one for the first resection guide feature 1276 and one for the second resection guide feature 1278.

In such an MIS procedure, the alignment guide 1302 may include at least one bone attachment feature 1304 such as a single prong 1310 that engages a single reference feature of the bone(s). Alternatively, or in addition, the alignment guide 1302 may include a single bone attachment feature 1304 such as a single cannulated prong 1310 that slides over a pin or post of the single reference feature of the bone(s). The surgeon may use the alignment guide 1302 as described herein in relation to other embodiments.

Advantageously, the present disclosure supports MIS surgical procedure using one or more embodiments of the navigation guide 1102, resection guide 1202, and/or alignment guide 1302. Those of skill in the art will appreciate that the bone attachment features 1280 of the resection guide 1202 and/or bone attachment feature 1304 of the alignment guide 1302 can be one or more posts or prongs that engage with reference features of the bone. Alternatively, or in addition, the bone attachment features 1280 of the resection guide 1202 and/or bone attachment feature 1304 of the alignment guide 1302 can be one or more cannulated posts or prongs that engage with reference features of the bone.

Those of skill in the art will appreciate other mechanisms that can be used to form reference features in the bone(s) and/or couple the resection guide 1202 and/or alignment guide 1302 to the reference features such that a surgeon can perform a surgical procedure as an MIS surgical procedure.

FIGS. 14A-14G are top perspective, top, bottom, front elevation, rear elevation, left, and right views respectively, of compression guide 1402 according to one embodiment. The compression guide 1402 can be an alternative embodiment of the compression guide 1038 for use with an osteotomy system. The compression guide 1402 may have many structures, features, and functions, operations, and/or configuration similar or identical to those of embodiments described herein, such as compression guide 1038, like parts are identified with the same reference numerals, except the first digit of the reference number is changed for this embodiment.

In the illustrated embodiment, the compression guide 1402 is configured to serve both as a compression guide (e.g., active compression instrument) and a distraction guide compression guide (e.g., active distraction instrument, another example of a complementary component 930). Advantageously, the compression guide 1402 is configured to supply parallel compression and/or distraction between a proximal reference feature and either a distal reference feature or alignment guide 1302.

The compression guide 1402 includes a first leg 1404, a second leg 1406, and a motion mechanism 1408. The motion mechanism 1408 can be activated in one manner to bring the first leg 1404 and second leg 1406 towards each other and activated in another manner to separate the first leg 1404 from the second leg 1406. In the illustrated embodiment, the motion mechanism 1408 includes a handle connected to a rod that includes external threads that engage internal threads of the first leg 1404 and second leg 1406. The motion mechanism 1408 may also include one or more stabilization rods.

Advantageously, the compression guide 1402 includes one or more of holes, openings, prongs, or other mechanisms suitable to engage the reference feature(s) and/or alignment features of a first bone and second bone to form an interface between the compression guide 1402 and the bones and/or bone fragments. Advantageously, the compression guide 1402 is configured to engage with the reference features of one or more different embodiments of the present disclosure.

In the illustrated embodiment, the reference features may comprise a proximal hole in one bone or bone fragment and a distal pin or post in another bone or bone fragment on an opposite side of a resection. Accordingly, the first leg 1404 includes at least one prong 1282 and the second leg 1406 includes at least one hole 1410 configured to engage the distal pin or post. A surgeon can insert the prong 1282 of the first leg 1404 in a reference feature, such as a hole in a cuneiform bone, and slide the holes of the second leg 1406 over pins extending from another bone or bone fragment, the pins serving as reference features. Next, a surgeon can activate the motion mechanism 1408 to distract the two bone fragments away from each other. Alternatively, or in addition, the surgeon can also activate the motion mechanism 1408 to drive or compress the two bone fragments towards each other. Alternatively, or in addition, the motion mechanism 1408 may be configured to remain in a set position until actuated by a user. Consequently, a surgeon can compress two bone fragments and maintain the same compression while deploying temporary or permanent fixation hardware.

FIGS. 15A-15G are top perspective, top, bottom, front elevation, rear elevation, left, and right views respectively, of compression guide 1502 according to one embodiment. The compression guide 1502 can be an alternative embodiment of the compression guide 1404 for use with an osteotomy system. The compression guide 1502 may have many structures, features, and functions, operations, and/or configuration similar or identical to those of embodiments described herein, such as compression guide 1402, like parts are identified with the same reference numerals, except the first digit of the reference number is changed for this embodiment.

One difference between the compression guide 1402 and the compression guide 1502 is the interface between the compression guide 1502 and the reference features and/or alignment features 1306. In the compression guide 1402, the second leg 1406 includes one or more holes 1410. In the compression guide 1502, the second leg 1406 includes one or more prongs 1282. Those of skill in the art will appreciate that the number and configuration of holes 1410 and/or prongs 1282 can vary in different embodiments based on the type of reference feature(s) and/or alignment features used in the bone or bone fragments.

FIGS. 16A-16H illustrate different views of stages of a surgical procedure. The example surgical procedure illustrated is for a Lapidus correction and arthrodesis.

Figures 16A, 16B, 16C, 16D:
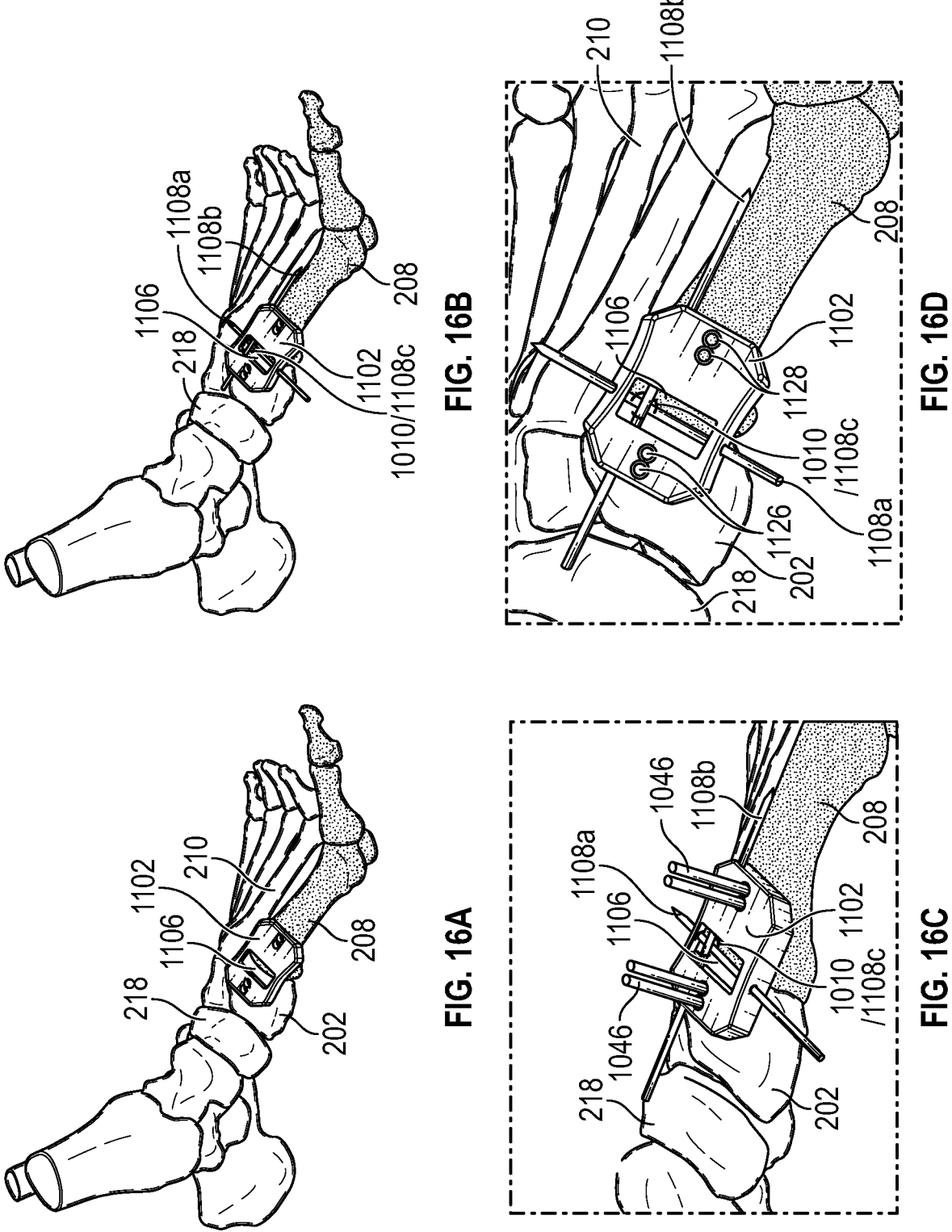

Referring to FIG. 16A, first, a surgeon positions a navigation guide 1102 approximately where desired. In one embodiment, the navigation guide 1102 may be initially positioned over a TMT between a medial cuneiform 202 and a first metatarsal 208. A surgeon may hold the navigation guide 1102 using their fingers, enlist the assistance of a surgical assistant, and/or use a handle connected to the navigation guide 1102.

Referring to FIG. 16B, next, a surgeon may deploy a first position indicator 1108a along a medial-lateral axis (e.g., an axis intended to be perpendicular to the proximal-distal axis) and a second position indicator 1108b along a proximal-distal axis (e.g., a first ray of the first metatarsal 208). The first position indicator 1108a and the second position indicator 1108b may be deployed in any sequence.

In one embodiment, the navigation guide 1102 is configured to position and orient the first position indicator 1108a such that the position indicator 1108a crosses a TMT joint medial-laterally and/or is perpendicular to the TMT joint. Said another way, the first position indicator 1108a is aligned with and parallel to an opening in the TMT joint between the medial cuneiform 202 and the first metatarsal 208. In one embodiment, the position indicator 1108 has a diameter small enough to be approximately the same distance as a gap between bones in the TMT joint (e.g., between 1-2 mm). With the first position indicator 1108a deployed and navigation guide 1102 in a planned or desired position, a surgeon can use fluoroscopy to see where the first position indicator 1108a crosses the TMT in relation to a gap between the bones of the TMT. In certain embodiments, a surgeon may desire to position the navigation guide 1102 such that the first position indicator 1108a is centered in a gap between bones of the TMT. In this manner, the first position indicator 1108a can assist a surgeon in positioning the navigation guide 1102 along a proximal-distal axis of the bones (e.g., medial cuneiform 202 and first metatarsal 208).

In one embodiment, the first position indicator 1108a extends across the opening 1106. In the illustrated embodiment, the first position indicator 1108*a* extends across the opening 1106 from a first side to a second side of the opening 1106 (e.g., from a medial side of opening 1106 to a lateral side of the opening 1106).

In one embodiment, the first position indicator 1108*a* is configured to align with an anatomical reference. In one example, the anatomical reference may be a space or gap between bones of a TMT joint. Alternatively, or in addition, the anatomical reference may be a distal most end of a medial cuneiform 202. Alternatively, or in addition, the anatomical reference may be a proximal most end of a first metatarsal 208. Advantageously, the present disclosure enables a surgeon to determine what anatomical reference they want to use with the first position indicator 1108*a* and/or how the position of the first position indicator 1108*a* is to relate to the anatomical reference.

With the first position indicator 1108*a* deployed, a user (e.g., surgeon) can move the navigation guide 1102 proximally and/or distally until the first position indicator 1108*a* aligns with a selected anatomical reference. Furthermore, a user can use the engagement of the bone engagement surface 1134 with one or more surfaces of one or more of the bones (e.g., medial cuneiform 202 and/or first metatarsal 208) to determine whether the navigation guide 1102 is in a desired position. If the first position indicator 1108*a* is not in the desired position in relation to the anatomical reference and/or the bone engagement surface 1134 "feels" out of place or not locked, engaged, or registered with one or more surfaces of the one or more bones, the surgeon may continue to adjust the position of the navigation guide 1102 proximally or distally until the bone engagement surface 1134 "locks" or registers in place and/or the first position indicator 1108*a* is in a desired position and/or relationship (e.g., aligned) with the anatomical reference.

In one embodiment, the surgeon may move the navigation guide 1102 distally and/or proximally until the bone engagement surface 1134 seats in the same position as planned in a preoperative plan. In this position, the bone engagement surface 1134 includes protrusions and recesses that mirrors those structures on the surface or surfaces of one or more bones in contact with the navigation guide 1102. This matching and/or seating is referred to as registration. Those of skill in the art will appreciate that a surgeon may deploy the position indicators 1108 or seat/register the bone engagement surface 1134 with the bones in any order. For example, the position indicators 1108 may be deployed and checked first and then the bone engagement surface 1134 registered. The bone engagement surface 1134 may be registered and then the position indicators 1108 deployed and check or any combination of these in any sequence.

Advantageously, the bone engagement surface 1134 is on the inferior side 1122 of the body 1104. The bone engagement surface 1134 is configured to engage with a bone of the patient when the body 1104 is in a desired position. In one embodiment, the desired position is a position for the body 1104 defined based at least in part on a bone model of a bone (e.g., medial cuneiform 202 and/or first metatarsal 208) of the patient. The bone model may be defined based at least in part on medical imaging of a patient.

Next, a surgeon may deploy a second position indicator 1108*b*. The second position indicator 1108*b* is configured to align with an anatomical reference (e.g., the navigation guide 1102 and/or second position indicator 1108*b* may be configured to be parallel with the anatomical reference). The anatomical reference may be the same anatomical reference used with the first position indicator 1108*a* or a different anatomical reference. In one example, the anatomical reference may be a longitudinal axis of the medial cuneiform 202. Alternatively, or in addition, the anatomical reference may be a longitudinal axis of the navicular 218. Alternatively, or in addition, the anatomical reference may be a longitudinal axis of the first metatarsal 208.

In one embodiment, the navigation guide 1102 is configured to position and orient the second position indicator 1108*b* such that the second position indicator 1108*b* is parallel to where a first metatarsal 208 will be once a planned surgical procedure is completed. The second position indicator 1108*b* may indicate a trajectory for a first bone or bone fragment in relation to a second bone or bone fragment after one or more steps for addressing a bone condition present in a patient. In one embodiment, the second position indicator 1108*b* is configured to indicate a final position of a first metatarsal 208 once the surgical procedure is completed. Thus, in certain embodiments, the surgeon may be looking to see that the first metatarsal 208 will be parallel to a second metatarsal 210. If the planned position for the first metatarsal 208 is not where the surgeon wants it to be, the surgeon may swap out the navigation guide 1102 for a different one with a different amount of adjustment.

A surgeon may use the second position indicator 1108*b* to visually see where the first metatarsal 208 will be once the surgical procedure is completed. In this manner, a surgeon can check to see where the anatomy will be following a surgical procedure to confirm that the changes planned are appropriate and/or desired given the condition of the patient before making any cuts into bone.

As with the first position indicator 1108*a*, the second position indicator 1108*b* may extend across the opening 1106. In the illustrated embodiment, the second position indicator 1108*b* traverses the first position indicator 1108*a* within the opening 1106. The second position indicator 1108*b* is configured to indicate a trajectory of a first bone or bone fragment (e.g., first metatarsal 208) in relation to a second bone or bone fragment (e.g., second metatarsal 210 and/or medial cuneiform 202) after one or more steps for addressing a bone condition present in a patient.

In another embodiment, the first position indicator 1108*a* and second position indicator 1108*b* may not traverse each other within the opening 1106. Instead, the first position indicator 1108*a* and second position indicator 1108*b* may extend through the opening 1106 parallel to each other. Alternatively, or in addition, the first position indicator 1108*a* and second position indicator 1108*b* may extend through the opening 1106 with a different relationship to each other that a surgeon can use to validate positions, orientations, trajectories, and the like before taking steps in a surgical procedure that cannot be reversed.

In one embodiment, the navigation guide 1102 includes a plurality of holes 1124 to permit the first position indicator 1108*a* to extend across the opening 1106. The plurality of holes 1124 may be referred to as position indicator holes. The holes 1124 are configured to accept the position indicators 1108. In certain embodiments, the navigation guide 1102 may include only a predetermined number and configuration of holes 1124 positioned to ensure the position indicators 1108 deployed will be in positions planned prior to the surgical procedure. Alternatively, or in addition, the navigation guide 1102 may include two or more sets of position indicator holes 1124. One set may enable deployment of one or the other or both of the position indicators 1108 in a first configuration and/or orientation according to a first plan and another set may enable deployment of one or the other or both of the position indicators 1108 in a first configuration and/or orientation according to a second or alternative plan.

In the illustrated embodiment, the navigation guide 1102 includes a plurality of position indicator holes. A first set of position indicator holes 1124 may be configured to accept the first position indicator 1108*a* and a second set of position indicator holes 1124 may be configured to accept the second position indicator 1108*b*. In one embodiment, the plurality of position indicator holes 1124 are configured such that a first position indicator 1108*a* deployed through a first set of position indicator holes 1124 and a second position indicator 1108*b* deployed through a second set of position indicator holes form a third position indicator within the opening 1106 (e.g., window). This third position indicator 1108*c* provides an additional aid to a surgeon during a surgical procedure. In the illustrated embodiment, the third position indicator 1108*c* is a crosshair 1010. Advantageously, the second position indicator 1108*b* may have a diameter similar to that of the first position indicator 1108*a*.

In one embodiment, the first position indicator 1108*a* crosses over the second position indicator 1108*b* within the opening 1106 (also referred to as a window). Where the two position indicators 1108 intersect may form a crosshair 1010/1108*c*. The surgeon may check to see if the crosshair 1010/1108*c* is in a desired position relative to the bones of the TMT joint. The navigation guide 1102 may be customized to a particular patient and/or surgeon requests. Thus, the surgeon can have confidence that if the crosshairs 1010/1108*c* are not where the surgeon expects them to be based on a preoperative plan, the surgeon can reposition the navigation guide 1102 and check again using fluoroscopy until the crosshair 1010/1108*c* is in the desired position. Advantageously, in one embodiment the position indicators 1108 are visible on fluoroscopy and the body 1104 of the navigation guide 1102 is transparent under fluoroscopy.

Once the surgeon has positioned the navigation guide 1102 in a desired position, the surgeon is assured that reference features formed on or in the bone(s) will guide remaining steps of a surgical procedure. Note in certain embodiments, the navigation guide 1102 can include a bone engagement surface that enables the navigation guide 1102 to register to one or more bones and/or one or more joints of a patient. Alternatively, or in addition, the navigation guide 1102 may include a skin engagement surface that enables the navigation guide 1102 to register to skin or other soft tissue and/or one or more joints of a patient. In still other embodiments, the navigation guide 1102 may include a nonpatient-specific surface and the surgeon may instead position the navigation guide 1102 using the crosshair.

Those of skill in the art will appreciate that the navigation guide 1102 may use other structures besides position indicator holes 1124 to engage and retain the position indicators 1108. Alternatively, or in addition, those of skill in the art will appreciate that a variety of configurations of holes 1124 can be used. For example, in one embodiment, the holes 1124 may be on a distal side of the body 1104 but not on the proximal side or on a lateral side but not a medial. Alternatively, or in addition, certain holes 1124 may extend through the body 1104 while others extend part way into the body. For example, in one embodiment, one or more of the holes 1124 are blind holes. For example, a holes 1124 in a side wall of the window 1106, opening 1106 may extend into the side wall without connecting to the opposite surface. Blind holes may be useful for a navigation guide 1102 with tight and limited space for position indicators 1108.

In one embodiment, a surgeon may use fluoroscopy to check the position of the position indicators 1108 in relation to anatomical references. In such an embodiment, the body 1104 of the navigation guide 1102 may be radiolucent and the position indicator 1108 may be radiopaque. In this manner, the position indicators 1108 may show up readily on fluoroscopy while the body 1104 may not. In yet another embodiment, the navigation guide 1102 may include a window that is not a hole or opening, but instead is a type of material of the body 1104 that is radiolucent. In this manner, the window can be a solid material that permits passage of radio waves such that position indicators 1108, including a crosshair 1010/1108*c* can be seen using fluoroscopy.

Referring to FIG. 16C, with the navigation guide 1102 in a desired position a surgeon or other user may keep the navigation guide 1102 in place, for example by holding the navigation guide 1102 in place. Depending on the kinds of reference features the surgeon desires to use, the surgeon may then either drill holes in the bone using the proximal holes 1126 and/or distal holes 1128 to guide the drilling of the holes and a drill bit 1602 or deploy fasteners such as pins using the proximal holes 1126 and/or distal holes 1128. Alternatively, or in addition, a surgeon may deploy pins and then remove them to form holes that can serve as reference features.

FIG. 16D is a close-up view showing the navigation guide 1102, opening 1106, position indicators 1108*a,b*. The holes (reference features) in the bones are not shown in FIG. 12D. It should be noted that navigation guide 1102 can be configured to be positioned on a medial side of the foot or a dorsal side of the foot. Because the navigation guide 1102 can be patient-specific a surgeon may determine which side of the foot and/or TMT the navigation guide 1102 should be positioned.

Next, the surgeon may remove the navigation guide 1102. If the reference features are holes in the bones the pins or other fasteners in the navigation guide 1102 may be removed. If the reference features are pins or posts in the bones the navigation guide 1102 can be removed while leaving the pins or other fasteners in the bones. Of course, a combination of pins and/or holes can serve as reference features.

Referring to FIG. 16E (the two bones of the joint are shown transparent for clarity), suppose the reference features include proximal holes in a first bone and distal holes in a second bone. Next, a surgeon may deploy a resection guide 1202 that includes prongs 1282 that correspond to reference features (e.g., holes) in the bones. The surgeon may seat the prongs 1282 of the resection guide 1202 into the reference features.

Next, a surgeon may make one or more resections of one or more bones, depending on the design and configuration of the resection guide 1202. The illustrated resection guide 1202 has a first resection guide feature 1276 and a second resection guide feature 1278.

FIG. 16F illustrates a configuration of the bones after the osteotomy, including one or more reference features 1602.

FIG. 16G illustrates two alternative compression guides, compression guide 1402 and compression guide 1502. The surgeon can use the compression guide 1502 where the bones have reference features embodied as holes. Of course, the first leg 1404 can have one or two prongs 1282. The surgeon can use the compression guide 1402 where the bones have reference features embodied as pins or posts. Of course, the first leg 1404 can have one or two prongs 1282.

FIG. 16H illustrates the medial cuneiform 202 and the first metatarsal 208 after the osteotomies. The compression guide is not shown, and fixation hardware is not shown.

Figure 17:
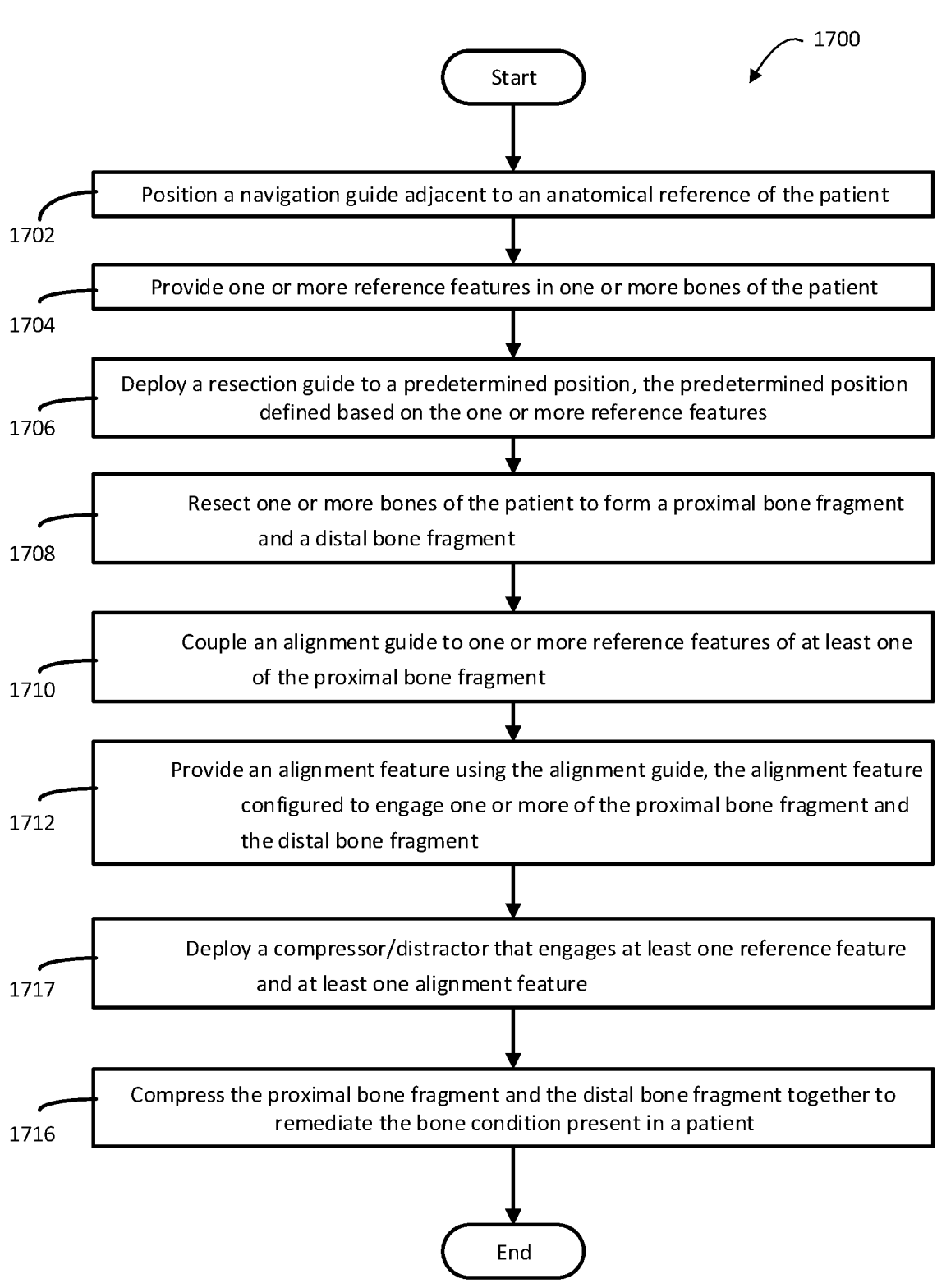
FIG. 17 illustrates a method for resecting and/or providing fixation for one or more bones, according to one embodiment.

FIG. 17 illustrates a method for remediating a bone condition present in a patient, according to one embodiment. FIG. 17 is a flowchart of an example process 1700. In some implementations, one or more process blocks of FIG. 17 may be performed by a system or a device.

As shown in FIG. 17, process 1700 may include positioning a navigation guide adjacent to an anatomical reference of the patient, the navigation guide having: a body having a proximal end that includes a proximal side and a distal end that includes a distal side, a medial side, a lateral side, a superior side, and an inferior side; a window that extends from the superior side to the inferior side, the window having a proximal edge, a distal edge, a medial edge, and a lateral edge; a first position indicator that extends across the window between the proximal edge and the distal edge; a second position indicator that extends across the window between the medial edge and the lateral edge (block 1702). For example, a user may position a navigation guide over an anatomical reference of the patient. The anatomical reference may be a TMT joint of a patient. Alternatively, or in addition, the anatomical reference may be a proximal end of a first metatarsal 208.

As also shown in FIG. 17, process 1700 may include providing one or more reference features in one or more bones of the patient (block 1704). For example, a system or a device may provide one or more reference features in one or more bones of the patient, as described above. The reference features may include holes in bones, K-wires or pins deployed in bones, a structure such as a navigation guide secured to the one or more bones, or the like.

As further shown in FIG. 17, process 1700 may include deploying a resection guide to a predetermined position, the predetermined position determined based on the one or more reference features, the resection guide having: a proximal end that includes a proximal side; a distal end that includes a distal side; a medial side, a lateral side, a superior side, and an inferior side; a bone attachment feature configured to engage one or more bones and secure the resection guide to the one or more bones; one or more resection guide features configured to guide a cutting tool in resecting tissue of the patient (block 1706). For example, a user may deploy a resection guide to a predetermined position, the predetermined position determined based on the one or more reference features. In one embodiment, the resection guide includes one or more resection guide features.

In one embodiment, deployment of the resection guide may include sliding the resection guide over pins (one example implementation of reference features) deployed in bones of a patient. In certain embodiments, the predetermined position can be determined by a structure of a navigation guide. For example, the navigation guide may include one or more bone attachment features 1280 configured to engage with one or more reference features (e.g., holes in the one or more bones, formed using reference feature guides, such as holes or openings in a navigation guide). Alternatively, or in addition, the resection guide may include one or more prongs 1282 that engage holes in bone to position the resection guide.

In another embodiment, the process 1700 may include deployment of the resection guide to a predetermined position may include coupling a resection guide to the navigation guide such that the resection guide takes a predetermined position. In one embodiment, the predetermined position is determined based on the one or more reference features. In such an embodiment, the navigation guide may serve as a platform and/or support for deployment of a resection guide. The navigation guide may be anchored to the one or more bones by pins deployed into reference feature guides, such that the pins serve as the reference features for the navigation guide and the resection guide and/or the pins serve as the reference features for the resection guide directly. Such an embodiment is described in more detail in relation to FIGS. 18 and 19.

The resection guide and the navigation guide may be coupled by way of a permanent or temporary engagement interface, coupler, fastener, snap mechanism, snap-fit interface, or the like. Those of skill in the art will appreciate that the engagement interface can be any of a number of different mechanisms and/or mechanical interfaces including but not limited to a friction fit, a snap-fit, a keyed interface, a hook and loop, a clip, a snap, a screw, or the like.

As also shown in FIG. 17, process 1700 may include resecting one or more bones of the patient by activating a cutting tool within at least one of the resection guide features of the resection guide to form a proximal bone fragment and a distal bone fragment (block 1708). For example, a user may resect one or more bones of the patient by activating a cutting tool within at least one of the resection guide features of the resection guide to form a proximal bone fragment and a distal bone fragment, as described above. In one example embodiment, the proximal fragment may be a proximal end of a bone and the distal fragment may be a distal end of the same bone.

In another example embodiment, a first bone and second bone may form a joint. The first bone may be proximal to the second bone in the joint. In this example embodiment, the proximal fragment may include a distal end of the first bone and the distal fragment may include a proximal end of the second bone. In this example embodiment, resecting 1708 may include two resections one near a distal end of the first bone and one near a proximal end of the second bone. In such an embodiment, the distal end of the first bone that is resected may be removed and the proximal end of the second bone resected may be removed such that the resected first bone and resected second bone can be fused as part of a surgical procedure.

As further shown in FIG. 17, process 1700 may include coupling an alignment guide (or a pin guide) to the one or more reference features of one or more of the proximal bone fragment and the distal bone fragment (block 1710). For example, a user may couple an alignment guide (or a pin guide) to the one or more reference features of one or more of the proximal bone fragment and the distal bone fragment, as described above. In one embodiment, the alignment guide (aka pin guide) may be coupled to one or more reference features implemented as pins or k-wires deployed into one or more bones by sliding the alignment guide over proximal ends of the pins or k-wires. In another embodiment, the alignment guide (aka pin guide) may be coupled to one or more reference features implemented as holes in one or more bones by prongs, spikes, rods, or another protrusion from the alignment guide the holes in one or more bones.

As also shown in FIG. 17, process 1700 may include providing an alignment feature using the alignment guide, the alignment feature configured to engage one or more of the proximal bone fragment and the distal bone fragment (block 1712). For example, a system or a device may provide an alignment feature using the alignment guide, the alignment feature configured to engage one or more of the proximal bone fragment and the distal bone fragment, as described above. In one embodiment, the alignment feature may comprise pins or K-wires deployed using holes in alignment guide. The holes of the alignment guide may be strategically positioned such that pins deployed in one or more bone fragments can be re-positioned, rotated and/or aligned when two bone fragments are reduced and/or fused.

As further shown in FIG. 17, process 1700 may include deploying a compressor/distractor that engages at least one reference feature and at least one alignment feature (block 1714). For example, a user may deploy a compressor/distractor that engages at least one reference feature and at least one alignment feature, as described above. The reference feature may be a hole, or a pin provided using a navigation guide and the alignment feature may be one or more pins or K-wires deployed in one or more bones using the alignment guide.

As also shown in FIG. 17, process 1700 may include compressing the proximal bone fragment and the distal bone fragment together to remediate the bone condition (block 1716). For example, a system or a device may compress the proximal bone fragment and the distal bone fragment together to remediate the bone condition, as described above.

Process 1700 may include additional implementations, such as any single implementation or any combination of implementations described below and/or in connection with one or more other processes described elsewhere herein. A first implementation process 1700 may include fixating the proximal bone fragment to the distal bone fragment.

Although FIG. 17 shows example blocks/steps of process 1700, in some implementations, process 1700 may include additional blocks, fewer blocks, different blocks, or differently arranged blocks than those depicted in FIG. 17. Additionally, or alternatively, two or more of the blocks of process 1700 may be performed in parallel.

Figure 18:
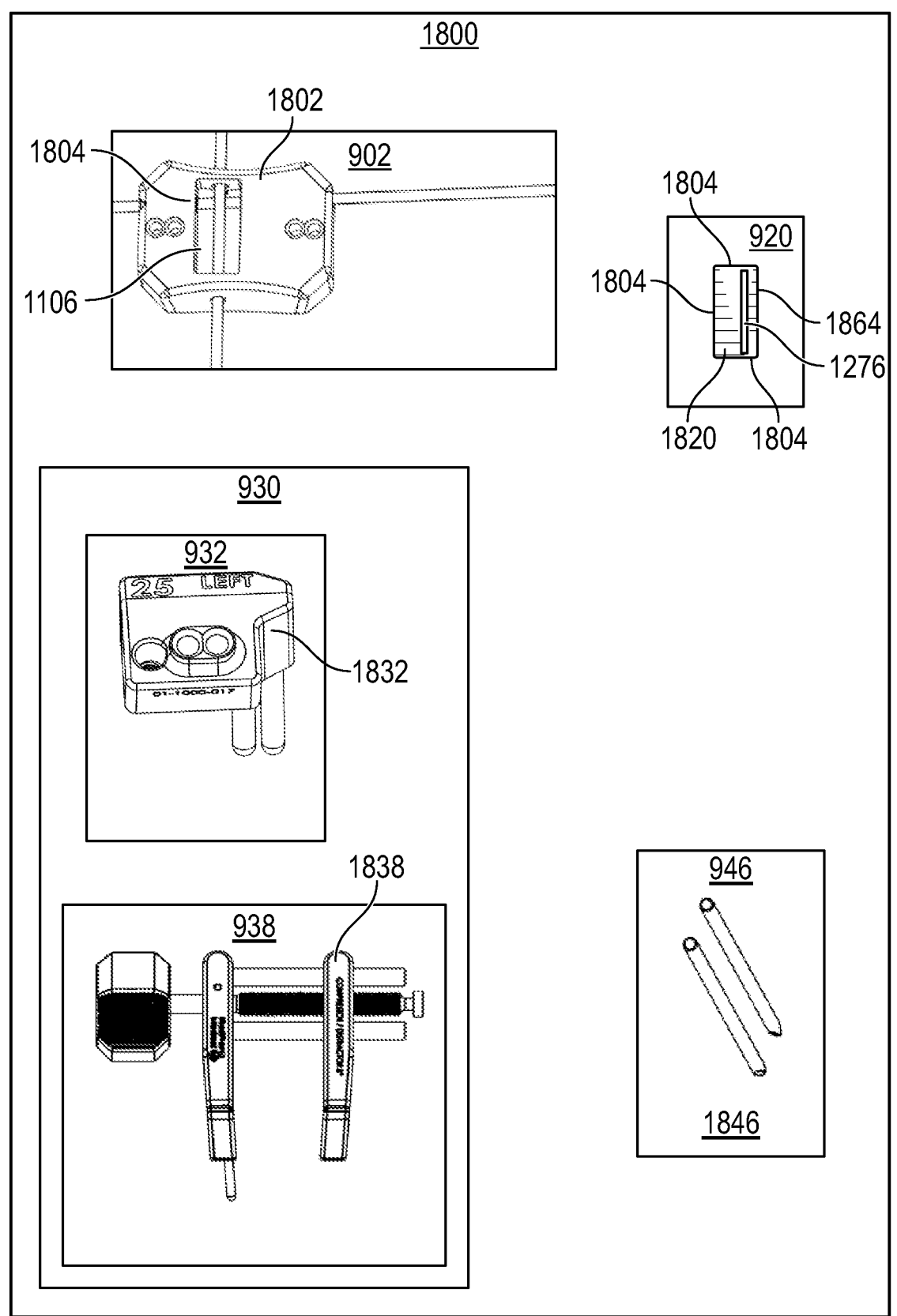
FIG. 18 illustrates an exemplary system for a surgical procedure, according to one embodiment.

FIG. 18 illustrates an exemplary osteotomy system 1800 for a surgical procedure, according to one embodiment. The osteotomy system 1800 is similar to the osteotomy system 1000 with the exception that an alternative embodiment of a resection guide is used in place of the resection guide 1020. In one embodiment of the osteotomy system 1800, the resection guide may be embodied as a resection guide insert 1820 or resection guide adapter 1820, also referred to as a drop-in resection guide 1820.

In the osteotomy system 1800 the navigation guide 902 can serve as a platform or framework for using any of a plurality of differently configured instrumentation, including for example, resection guides 1820. In the osteotomy system 1800 the navigation guide 1802 can be configured to include an engagement interface 1804, a coupler, or other engagement mechanism that engages with the resection guide insert 1820 and retains the resection guide insert 1820 while one or more osteotomies are performed using the resection guide insert 1820. In one embodiment, the engagement interface 1804 engages with a resection guide insert 1820 temporarily. Alternatively, or in addition, the engagement interface 1804 engages with a resection guide insert 1820 permanently.

In one example, the opening 1106 of the navigation guide 1802 can be configured to include all or part of an engagement interface 1804 that is configured to engage with one or more different resection guide inserts 1820. Alternatively, or in addition, the engagement interface 1804 may be configured to engage with one or more instruments that a surgeon may use for a surgical procedure.

In certain embodiments, the resection guide insert 1820 may include a window in place of an opening 1106. Alternatively, or in addition, the opening 1106 may serve as a window. Advantageously, the window (e.g., opening 1106)

is configured to accept a resection guide insert 1820. The resection guide insert 1820 is configured to guide a cutting tool to form one or more osteotomies in at least one bone. For example, in one embodiment, the resection guide insert 1820 may include at least one resection guide feature 1276. The resection feature may be implemented as a slot that enables and guides a cutting tool to cut bone positioned on one side of the navigation guide 1802.

Those of skill in the art will appreciate a variety of different mechanical implementations that can be used to realize the engagement interface 1804. In one embodiment, the engagement interface 1804 includes a key and a keyhole. In another embodiment, the engagement interface 1804 includes a pin and a hole. In another embodiment, the engagement interface 1804 can include a latch and a catch. In another embodiment, the engagement interface 1804 can include a snap-fit mechanism. In another embodiment, the engagement interface 1804 can include a friction fit interface between one or more edges of the opening 1106 and the resection guide insert 1820.

The resection guide insert 1820 can include a single resection guide feature 1806 or a plurality of resection guide features 1804. Said another way, the engagement interface 1804 can include a single cut channel, two cut channels, or three or more cut channels. The cut channels can be patient-specific and can be oriented in the resection guide insert 1820 to result in a desired osteotomy and/or correction upon completion of a surgical procedure. In one embodiment, the resection guide insert 1820 may lock in place relative to the engagement interface 1804. Alternatively, or in addition, the resection guide insert 1820 can be unlocked in relation to the engagement interface 1804 and/or navigation guide 1802 such that one resection guide insert 1820 can be removed and a different resection guide insert 1820 used instead or in addition.

In certain embodiments, the resection guide insert 1820 can serve as a kind of insert or adapter that can be used together with the navigation guide 1802 to perform a variety of different surgical procedures.

When the navigation guide 1102 securely engages with a resection guide 1202 the surgeon may hear an audible snap or click, that may come from the engagement interface 1804. Alternatively, or in addition, when the navigation guide 1102 securely engages with a resection guide 1202 the surgeon may feel a tactile movement that indicates by feel that the navigation guide 1102 and resection guide 1202 are securely engaged. The tactile movement may come from the engagement interface 1804.

In one embodiment, the navigation guide 1102 may engage the resection guide 1202 permanently. In another embodiment, the resection guide 1202 may engage with the navigation guide 1102 such that the resection guide 1202 can be removed, as needed.

FIGS. 19A-19D illustrates examples of a few, of a variety of different types and configurations of resection guides 1820 that can be used with the navigation guide 1102 and/or engagement interfaces 1804. Resection guide insert 1820*a* illustrates an example of a resection guide insert 1820 that includes a single resection guide feature 1276. The single resection guide feature 1276 can be used for resection of one bone or for resection of one cut in a wedge to be removed from a bone. In one embodiment, the first resection guide feature 1276 can be used to resection a first metatarsal 208. Resection guide insert 1820*b* illustrates an example of a resection guide insert 1820 that includes a single resection guide feature 1276. The bone to be resected by the resection guide insert 1820*b* may be different from a bone that can be resected using the resection guide insert 1820*a*. The single resection guide feature 1276 can be used for resection of one bone or for resection of one cut in a wedge to be removed from a bone. In one embodiment, the first resection guide feature 1276 can be used to resection a medial cuneiform 202. In certain embodiments, the resection guide insert 1820*a* can be used to resect one cut for a wedge and the resection guide insert 1820*b* can be used to resect another cut to complete the wedge initially cut with the resection guide insert 1820*a*.

Resection guide insert 1820*c* illustrates an example of a resection guide insert 1820 that includes a first resection guide feature 1276 and a second resection guide feature 1278. The first resection guide feature 1276 and second resection guide feature 1278 can be used to resect two different bones or to resect parts of a single bone or to resect parts of a wedge or other shape to be removed from one or more bones.

Resection guide insert 1820*c* illustrates an example of a resection guide insert 1820 that includes a first resection guide feature 1276, a second resection guide feature 1278, and a third resection guide feature 1279. The first resection guide feature 1276, second resection guide feature 1278, third resection guide feature 1279 can be used to resected two different bones, three different bones, or to resect parts of a single bone or parts of multiple bones, or to resect parts of a wedge or other shape to be removed from one or more bones. In one embodiment, the third resection guide feature 1279 can be used to create an opening in a wedge to facilitate removal.

In certain embodiments, the resection guide insert 1820 is patient-specific and may be fabricated based on anatomic data 412, medical imaging, and/or one or more bone models 404. In one embodiment, the position, orientation, size, and/or trajectory of each resection guide feature 1276 of a resection guide insert 1820 may be patient-specific, may be based on preferences or instructions from a user (e.g., surgeon), or may be set, determined, and/or defined based on industry practice.

In another embodiment, the resection guide insert 1820 is patient-matched for a particular patient based on certain attributes and/or characteristics of the patient, including but not limited to size of the foot, size of the deformity, angles for certain landmarks, angles for a deformity, type of deformity, size of the bone, and the like. In such an embodiment, the osteotomy system 1800 may include a plurality of resection guide inserts 1820 each with different characteristics such that a surgeon may initially start with a recommended resection guide insert 1820 and then switch to another resection guide insert 1820 based on their own preference, professional judgement, or the like.

Referring to FIG. 17 and FIG. 19A, in certain embodiments, the method 1700 may include use of a resection guide insert 1820 rather than a resection guide. For example, in one embodiment, the resection guide comprises a resection guide insert. In such an embodiment, the step of 1706 may include coupling a resection guide insert to the navigation guide. The navigation guide may be coupled to one or more reference features (e.g., pin, K-wires, holes, etc.). In this manner, the reference features facilitate placement and orientation of the navigation guide and the navigation guide serves to engage and retain a resection guide insert 1820 for one or more osteotomies.

FIG. 19B illustrates one example engagement interface 1804 in which the resection guide insert 1820*e* includes a lip 1810 that engages with an edge (e.g., a proximal edge 1150, a distal edge 1152, a medial edge 1154, and a lateral edge 1156) of an opening 1106 of a navigation guide 1802.

FIG. 19C illustrates one example engagement interface 1804 in which the resection guide insert 1820*f* includes teeth 1812 that slip into openings 1814 in a wall of the opening 1106 of a navigation guide 1802 and can lock in place. Those of skill in the art will appreciate that the engagement interface 1804 can have a variety of implementations. FIG. 19C illustrates one example of a snap-fit interface between the resection guide insert 1820 and the navigation guide 1802. Of course, a variety of other snap-fit interfaces can be used with the resection guide insert 1820 and/or navigation guide 1802.

FIG. 19D illustrates one example engagement interface 1804 in which the resection guide insert 1820*g* includes a key structure 1816 that slides into a corresponding opening 1818 in a side wall of an opening 1106 of a navigation guide 1802. In this manner, the resection guide insert 1820 can lock in place and still be readily removed. Those of skill in the art will appreciate that the engagement interface 1804 may be configured such that different resection guide inserts 1820 are interchangeable with each other. In certain embodiments, one resection guide insert 1820*g* can be used to resect a first bone (e.g., medial cuneiform 202) and the resection guide insert 1820*g* can then be exchanged with a resection guide insert 1820 (e.g., resection guide insert 1820*a*) for use in resecting a second bone (e.g., first metatarsal 208). In this manner, a surgeon has great flexibility in which resection guide insert 1820 to use for the surgical procedure.

Alternatively, or in addition, the navigation guide 1802 may be configured to accept two or more resection guide inserts 1820. Or the navigation guide 1802 may be configured to accept a single resection guide insert 1820 in a plurality of locations/positions within the navigation guide 1802. In the illustrated embodiment, the navigation guide 1802 may include a first opening 1830 and a second opening 1840. The first opening 1830 may accept a first resection guide insert 1820 such as resection guide insert 1820*g* for resecting a proximal bone (e.g., a medial cuneiform 202). The second opening 1840 may accept a second resection guide insert 1820 such as resection guide insert 1820*h* for resecting a distal bone (e.g., a first metatarsal 208). In this manner, a single navigation guide 1802 can be used to facilitate resection of two bones of a joint of a patient. Alternatively, or in addition, the first opening 1830 and second opening 1840 may retain the same or different resection guide inserts 1820 for resecting a single bone.

In certain embodiments, other components of an osteotomy system 900, such as the complementary components 930 can be used with or adapted or designed to be used with the navigation guide 1102 as well.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements recited in means-plus-function format are intended to be construed in accordance with 35 U.S.C. § 112 Para. 6. It will be apparent to those having skill in the art that changes may be made to the details of the above-described embodiments without departing from the underlying principles set forth herein.

While specific embodiments and applications of the present disclosure have been illustrated and described, it is to be understood that the scope of this disclosure is not limited to the precise configuration and components disclosed herein. Various modifications, changes, and variations which will be apparent to those skilled in the art may be made in the arrangement, operation, and details of the methods and systems of the present disclosure set forth herein without departing from it spirit and scope.

The invention claimed is:

1. A method for remediating a bone condition present in a patient, the method comprising:

positioning a navigation guide comprising a body having proximal, distal, medial, lateral, inferior, and superior sides and an opening that extends from the superior side to the inferior side of the body, wherein positioning the navigation guide comprises making an anatomical reference of the patient visible through the opening of the navigation guide;

deploying at least one position indicator into the opening by passing the at least one position indicator through at least one of the proximal, distal, medial, and lateral sides of the body;

indicating a position of the navigation guide by comparing the at least one position indicator to the anatomical reference viewed through the opening;

providing one or more reference features relative to a bone or a first bone fragment of the patient using the navigation guide;

deploying a resection instrument relative to the one or more reference features, the resection instrument configured to address the bone condition by forming at least one second bone fragment in the bone or the first bone fragment; and deploying a compression guide that engages at least two of the one or more reference features to compress the at least one second bone fragment and one of the bone and the first bone fragment to remediate the bone condition.

2. The method of claim 1, wherein positioning the navigation guide comprises engaging a bone engagement surface of the navigation guide with a bone of the patient.

3. The method of claim 2, wherein the bone engagement surface is positioned based at least in part on a bone model defined from medical imaging data.

4. The method of claim 1, further comprising deploying a resection guide insert within the opening, the resection guide insert configured to guide a cutting tool to form one or more osteotomies in at least one bone.

5. The method of claim 1, wherein indicating the position of the navigation guide comprises deploying the at least one position indicator through a first set of holes and a second position indicator through a second set of holes and wherein the at least one position indicator and the second position indicator form a crosshair within the opening.

6. The method of claim 5, wherein at least one of the holes is a blind hole.

7. The method of claim 1, wherein the navigation guide body comprises a radiolucent material.

8. The method of claim 1, wherein providing the one or more reference features comprises advancing a reference feature through a hole extending from a bone-facing side of the navigation guide.

9. The method of claim 1, wherein providing the one or more reference features comprises forming a reference feature through a hole extending from a bone-facing side of the navigation guide.

10. The method of claim 1, further comprising aligning a proximal bone fragment and a distal bone fragment using an alignment guide prior to compressing the at least one bone fragment.

11. The method of claim 1, further comprising indicating a trajectory of a first bone fragment relative to a second bone fragment using a second position indicator.

12. The method of claim 11, wherein the second position indicator intersects the at least one position indicator within the opening.

13. The method of claim 1, wherein deploying a resection instrument comprises coupling a resection guide insert to the navigation guide.

* * * * *